(12) United States Patent
Liu

(10) Patent No.: US 8,889,625 B2
(45) Date of Patent: Nov. 18, 2014

(54) CARDIOPROTECTIVE ROLE OF HEPATIC CELLS AND HEPATOCYTE SECRETORY FACTORS IN MYOCARDIAL ISCHEMIA

(75) Inventor: Shu Q. Liu, Glencoe, IL (US)

(73) Assignee: Northwestern University, Evanston, IL (US)

( * ) Notice: Subject to any disclaimer, the term of this patent is extended or adjusted under 35 U.S.C. 154(b) by 250 days.

(21) Appl. No.: 12/833,534

(22) Filed: Jul. 9, 2010

(65) Prior Publication Data

US 2011/0008281 A1 Jan. 13, 2011

Related U.S. Application Data

(60) Provisional application No. 61/224,691, filed on Jul. 10, 2009.

(51) Int. Cl.
| | | |
|---|---|---|
| A61K 38/17 | (2006.01) | |
| A61K 38/18 | (2006.01) | |
| A61K 35/407 | (2006.01) | |
| A61K 38/20 | (2006.01) | |

(52) U.S. Cl.
CPC ........... *A61K 38/1709* (2013.01); *A61K 35/407* (2013.01); *A61K 38/1825* (2013.01); *A61K 38/204* (2013.01)
USPC ............................ 514/16.4; 514/76; 514/21.2

(58) Field of Classification Search
None
See application file for complete search history.

(56) References Cited

U.S. PATENT DOCUMENTS

| | | | |
|---|---|---|---|
| 6,716,626 B1* | 4/2004 | Itoh et al. ...................... | 435/325 |
| 7,655,627 B2 | 2/2010 | Frye et al. | |
| 2006/0063204 A1 | 3/2006 | Valkirs et al. | |
| 2007/0190127 A1* | 8/2007 | Zhou ............................ | 424/450 |
| 2008/0176790 A1* | 7/2008 | DeFrees ....................... | 514/12 |
| 2008/0241208 A1 | 10/2008 | Shanley et al. | |
| 2009/0305986 A1* | 12/2009 | Belouski et al. ............... | 514/12 |
| 2010/0184644 A1* | 7/2010 | Thim et al. .................... | 514/8 |

FOREIGN PATENT DOCUMENTS

| | | |
|---|---|---|
| WO | 0136640 | 5/2001 |
| WO | 03099300 | 12/2003 |
| WO | 2010065439 | 6/2010 |

OTHER PUBLICATIONS

Lee et al., "Intronic regulation of matrix metalloproteinase-2 revealed by in vivo transcriptional analysis in ischemia," Proc. Natl. Acad. Sci. USA, 2005, 102, 16345-16350.
Leor et al., "Ex vivo activated human macrophages improve healing, remodeling, and function of infarcted heart," Circulation, 2006, 114,suppl I , I-94-I-100.
Li, Y., et al., "Postinfarction treatment with an adenoviral vector expressing hepatocyte growth factor relieves chronic left ventricular remodeling and dysfunction in mice," Circulation, 2003, 107, 2499-2506.
Liu et al., "Evidence for a role of basic fibroblast growth factor in rat embryonic growth and differentiation," Endocrinology, 1988, 123(4):2027-31.
Liu, et al., "Negative regulation of monocyte adhesion to arterial elastic laminae by signal-regulatory protein alpha and SH2 domain-containing protein tyrosine phosphatase-1," J. Biol. Chem. 2005, 280, 39294-39301.
Liu, et al., "Formation of smooth muscle σ actin filaments in CD34-positive bone marrow cells in elastic lamina-dominant matrix of arteries," Matrix Biology, 2008, 27, 282-294.
Lunde, et al., "Intracoronary injection of mononuclear bone marrow cells in acute myocardial infarction," N. Engl. J. Med. 2006, 355, 1199-1209.
Maeda et al., "Pathology of experimental radiation pancarditis. I. Observation on radiation-induced heart injuries following a single dose of x-ray irradiation to rabbit heart with special reference to its pathogenesis," Acta Pathol Jpn, 1980, 30(1):59-78.
Malin, et al., "Production of dissociated sensory neuron cultures and considerations for their use in studying neuronal function and plasticity," Nature Protocols, 2007, 2, 152-160.
Martins, et al., "Rodent models of partial hepatectomies," Liver Int, 2008, 28, 3-11.
Matsuoka, et al., "Neural crest origins of the neck and shoulder," Nature, 2005, 436, 347-355.
Michalopoulos et al., "Liver regeneration," Science, 1997, 276, 60-66.
Moore, et al., "Role of tensile stress and strain in the induction of cell death in experimental vein grafts," J. Biomech. 2001,34, 289-297.
Morimoto, et al., "Bone marrow-derived CXCR4+ cells mobilized by macrophage colony-stimulating factor participate in the reduction of infarct area and improvement of cardiac remodeling after myocardial infarction in mice," Am J Pathol. 2007, 171, 755-766.
Moser et al., "BMPER, a novel endothelial cell precursor-derived protein, antagonizes bone morphogenetic protein signaling and endothelial cell differentiation," Mol Cell Biol. 2003, 23(16):5664-79.
Murphy, G. "Matrix metalloproteinases and their inhibitors," Acta Orthop Scand Suppl, 1995,266, 55-60.
Murry, et al., "Haematopoietic stem cells do not transdifferentiate into cardiac myocytes in myocardial infarcts," Nature, 2004, 428, 664-668.
Nakamura, et al., "Myocardial protection from ischemia/reperfusion injury by endogenous and exogenous HGF," J Clin Invest, 2000, 106, 1511-1519.
Nishimoto et al., "Interleukin 6: from bench to bedside," Nat Clin Pract Rheumatol, 2006, 2, 619-626.
Nygren, et al., "Bone marrow-derived hematopoietic cells generate cardiomyocytes at a low frequency through cell fusion, but not transdifferentiation.," Nat. Med. 2004, 10, 494-501.
Orlic, et al., "Mobilized bone marrow cells repair the infarcted heart, improving function and survival," Proc Natl Acad Sci U S A , 2001, 98, 10344-10349.
Osypiw, et al., "Subpopulations of rat hepatocytes separated by Percoll density-gradient centrifugation show characteristics consistent with different acinar locations," Biochem. J. 1994, 304, 617-624.
Passier, et al., "Stem-cell-based therapy and lessons from the heart," Nature, 2008, 453, 322-329.

(Continued)

*Primary Examiner* — Marianne P Allen
(74) *Attorney, Agent, or Firm* — Casimir Jones S.C.

(57) ABSTRACT

The present invention provides methods, compositions, and systems for treating a subject at risk for, with, or suspected of having, myocardial ischemia using hepatocyte secretory factors (e.g., AGP2, BMPER, FGF21, NRG4, and/or TFF3) or using factors that promote liver cell migration to ischemic myocardial tissue (e.g., IL-6 and/or MMP-2).

13 Claims, 46 Drawing Sheets

(56) References Cited

OTHER PUBLICATIONS

Postic, et al., "Dual Roles for Glucokinase in Glucose Homeostasis as Determined by Liver and Pancreatic Cell-specific Gene Knock-outs Using Cre Recombinase," J Biol Chem, 1999, 274, 305-315.

Rehman, et al., 2003, "Peripheral blood "endothelial progenitor cells" are derived from monocyte/macrophages and secrete angiogenic growth factors," Circulation, 2007, 107, 1164-1169.

Rota, et al., "Bone marrow cells adopt the cardiomyogenic fate in vivo," Proc Natl Acad Sci USA , 2007, 104, 17783-17788.

Rota, et al., "Local activation or implantation of cardiac progenitor cells rescues scarred infarcted myocardium improving cardiac function," Circ Res. 2008, 103, 107-116.

Sands et al., "The trefoil peptide family," Annu Rev Physiol. 1996, 58:253-73.

Schindl, et al., "The value of residual liver volume as a predictor of hepatic dysfunction and infection after major liver resection.," Gut, 2005, 54, 289-296.

Schlüter, et al., "Adult ventricular cardiomyocytes: isolation and culture" Methods Mol Biol., 2005, 290, 305-314.

Segers et al., "Stem-cell therapy for cardiac disease" Nature, 2008, 451, 937-942.

Seglen, P.O. "Hepatocyte suspensions and cultures as tools in experimental carcinogenesis," J. Toxicol. Environ. Health , 1979, 5(2-3), 551-560.

Sehgal, et al., "Human chromosome 7 carries the beta-2 interferon gene," Proc Nat Acad Sci USA, 1986, 83, 5219-5222.

Shibata, et al., "Adiponectin protects against the development of systolic dysfunction following myocardial infarction,"J. Mol. Cell Cardiol. 2007, 42, 1065-1074.

Skinner, et al., "Transcriptional activation and transformation by FosB protein require phosphorylation of the carboxyl-terminal activation domain," Mol Cell Biol, 1997, 17, 2372-2380.

Srinivas, et al., "Cre reporter strains produced by targeted insertion of EYFP and ECFP into the ROSA26 locus," BMC Dev Biol. 2001;1:4. Epub Mar. 27, 2001.

Stadtfeld et al., "Assessing the role of hematopoietic plasticity for endothelial and hepatocyte development by non-invasive lineage tracing" Development, 2005, 132, 203-213.

Stern et al, "Tracing the lineage of tracing cell lineages," Nat Cell Biol. 2001, 3, E216-218.

Sutton, et al., "Quantitation of left ventricular volumes and ejection fraction in post-infarction patients from biplane and single plane two-dimensional echocardiograms. A perspective longitudinal study of 371 patients," European Heart Journal, 1998, 19, 808-816.

Taga et al., "Gp130 and the interleukin-6 family of cytokines," Annu Rev Immunol. 1997, 15, 797-819.

Taniyama, et al., "Potential contribution of a novel antifibrotic factor, hepatocyte growth factor, to prevention of myocardial fibrosis by angiotensin II blockade in cardiomyopathic hamsters," Circulation, 2000, 102, 246-252.

Taub, R. "Liver regeneration: from myth to mechanism.," Nat Rev Mol Cell Biol, 2004, 5, 836-847.

Urbanek, et al., "Cardiac stem cells possess growth factor-receptor systems that after activation regenerate the infarcted myocardium, improving ventricular function and long-term survival," Circ. Res. 2005, 97, 663-673.

Van Molle et al., "Activation of caspases in lethal experimental hepatitis and prevention by acute phase proteins," J Immunol. 1999, 163(10):5235-41.

Van Molle et al., "Alpha 1-acid glycoprotein and alpha 1-antitrypsin inhibit TNF-induced but not anti-Fas-induced apoptosis of hepatocytes in mice," J Immunol. 1997, 159(7):3555-64.

Vremec, et al., "The surface phenotype of dendritic cells purified from mouse thymus and spleen: investigation of the CD8 expression by a subpopulation of dendritic cells," J Exp Med. 1992, 176, 47-58.

Wong et al., "Trefoil peptides," Gut. Jun. 1999;44(6):890-5.

Zou, et al., "Leukemia inhibitory factor enhances survival of cardiomyocytes and induces regeneration of myocardium after myocardial infarction," Circulation, 2003, 108, 748-753.

Alison, et al., "Wound healing in the liver with particular reference to stem cells," Philos Trans R Soc Lond B Biol Sci. 1998, 353, 877-894.

Almeida-Porada, et al., "Formation of human hepatocytes by human hematopoietic stem cells in sheep," Blood, 2004, 104, 2582-2590.

Angel et al., "The role of Jun, Fos, and AP-1 complex in cell proliferation and transformation," Biochim. Biophys. Acta. 1991,1072, 129-157.

Appenheimer, et al., "Conservation of IL-6 trans-signaling mechanisms controlling L-selectin adhesion by fever-range thermal stress," European Journal of Immunology, 2007, 37, 2856-2867.

Arita et al., "Increased islet viability by addition of beraprost sodium to collagenase solution," Pancreas, 2001, 23, 62-67.

Badman et al., "Hepatic fibroblast growth factor 21 is regulated by PPARalpha and is a key mediator of hepatic lipid metabolism in ketotic states," Cell Metab. 2007, 5(6):426-37.

Badorff, et al., "Transdifferentiation of blood-derived human adult endothelial progenitor cells into functionally active cardiomyocytes," Circulation, 2003, 107, 1024-1032.

Balsam, et al., "Haematopoietic stem cells adopt mature haematopoietic fates in ischaemic myocardium," Nature, 2004, 428, 668-673.

Beltrami et al., "Adult cardiac stem cells are multipotent and support myocardial regeneration," Cell, 2003, 114, 763-776.

Bergman, et al., "A functional activating protein 1 AP-1 site regulates matrix metalloproteinase 2 MMP-2 transcription by cardiac cells through interactions with JunB-Fra1 and JunB-FosB heterodimers," Biochem. J. 2003, 369, 485-496.

Biasucci, et al., "Elevated levels of interleukin-6 in unstable angina," Circulation, 1996, 94, 874-877.

Brunner, et al., "Erythropoietin administration after myocardial infarction in mice attenuates ischemic cardiomyopathy associated with enhanced homing of bone marrow-derived progenitor cells via the CXCR-4/SDF-1 axis," FASEB J. 2009, 23, 351-361.

Cai, et al., "Suppression of hepatocyte growth factor production impairs the ability of adipose-derived stem cells to promote ischemic tissue revascularization.," Stem Cells, 2007, 25: 3234-3243.

Carrasco et al., "Trefoil Factor Family Peptide 3 Prevents the Development and Promotes Healing of Ischemia-Reperfusion Injury in Weanling Rats," J Pediatric Surg., 2004, 39:1693-1700.

Chen, et al., "Central role of IL-6 receptor signal-transducing chain gp130 in activation of L-selectin adhesion by fever-range thermal stress," Immunity , 2004, 20, 59-70.

Cleutjens, et al., "Collagen remodeling after myocardial infarction in the rat heart," Am J Path, 1995, 147, 325-338.

Cressman, et al., "Liver failure and defective hepatocyte regeneration in interleukin-6-deficient mice," Science, 1996, 274, 1379-1383.

Dill, et al., "Intracoronary administration of bone marrow-derived progenitor cells improves left ventricular function in patients at risk for adverse remodeling after acute ST-segment elevation myocardial infarction: results of the Reinfusion of Enriched Progenitor cells and Infarct Remodeling in Acute Myocardial Infarction study REPAIR-AMI cardiac magnetic resonance imaging substudy," Am Heart J, 2009, 157, 541-547.

Dostálová et al., "Fibroblast growth factor 21: a novel metabolic regulator with potential therapeutic properties in obesity/type 2 diabetes mellitus," Physiol Res. 2009, 58(1):1-7.

Eerola, et al., "The Influence of Percutaneous Closure of Patent Ductus Arteriosus on Left Ventricular Size and Function—A Prospective Study Using Two- and Three-Dimensional Echocardiography and Measurements of Serum Natriuretic Peptides," J. Am. Coll. Cardiol. 2006, 47, 1060-1066.

Fausto et al., "The role of hepatocytes and oval cells in liver regeneration and repopulation," Mech Dev. 2003, 120, 117-130.

Fazel, et al., "Activation of c-kit is necessary for mobilization of reparative bone marrow progenitor cells in response to cardiac injury," FASEB J. 2008, 22, 930-940.

Fisman, et al., "Interleukin-6 and the risk of future cardiovascular events in patients with angina pectoris and/or healed myocardial infarction.," Am J Cardiol. 2006, 98, 14-18.

Forbes, et al., "Hepatic stem cells," J Pathol. 2002, 197, 510-518.

Fournier et al., "Alpha-1-acid glycoprotein," Biochim Biophys Acta. 2000,1482(1-2):157-71.

(56) References Cited

OTHER PUBLICATIONS

Fukumoto et al., "Actions and mode of actions of FGF19 subfamily members," Endocr J. 2008, 55(1):23-31.
Greene et al., "Partial hepatectomy in the mouse: technique and perioperative management," J Invest Surg, 2003, 16, 99-102.
Guerre-Millo et al., "Peroxisome proliferator-activated receptor alpha activators improve insulin sensitivity and reduce adiposity," J Biol Chem. 2000, 275(22):16638-16642.
Gyöngyösi, et al., "Combined delivery approach of bone marrow mononuclear stem cells early and late after myocardial infarction: the MYSTAR prospective, randomized study," Nat Clin Pract Cardiovasc Med, 2009, 6, 70-81.
Harari et al., "Neuregulin-4: a novel growth factor that acts through the ErbB-4 receptor tyrosine kinase," Oncogene. 1999, (17):2681-9.
Hayes et al., "Characterization of the cell membrane-associated products of the Neuregulin 4 gene," Oncogene. 2008, 27(5):715-20.
Heinke et al., "BMPER is an endothelial cell regulator and controls bone morphogenetic protein-4-dependent angiogenesis," Circ Res. 2008, 103(8):804-12.
Hirano, et al., "Complementary DNA for a novel human interleukin BSF-2 that induces B lymphocytes to produce immunoglobulin," Nature, 1986, 324, 73-76.
Hofmann, et al. "Matrix metalloproteinases in human melanoma," J Invest Dermatol. 2000, 115, 337-344.
Hotta et al., "Fibroblast growth factor 21 regulates lipolysis in white adipose tissue but is not required for ketogenesis and triglyceride clearance in liver," Endocrinology. 2009, 150(10):4625-33.
Huotari et al., "ErbB signaling regulates lineage determination of developing pancreatic islet cells in embryonic organ culture," Endocrinology. 2002, 143(11):4437-46.
Ii, M. et al., "Endothelial progenitor cells are rapidly recruited to myocardium and mediate protective effect of ischemic preconditioning via "imported" nitric oxide synthase activity," Circulation, 2005, 111, 1114-1120.
Ikeya et al., "Essential pro-Bmp roles of crossveinless 2 in mouse organogenesis," Development. 2006, 133 (22):4463-73.
Inagaki et al., "Endocrine regulation of the fasting response by PPARalpha-mediated induction of fibroblast growth factor 21," Cell Metab. 2007, 5(6):415-25.
Iwakura, et al., "Estradiol enhances recovery after myocardial infarction by augmenting incorporation of bone marrow-derived endothelial progenitor cells into sites of ischemia-induced neovascularization via endothelial nitric oxide synthase-mediated activation of matrix metalloproteinase-9," Circulation, 2006, 113, 1605-1614.
Johns, et al., "Isolation of renin-rich rat kidney cells," Hypertension, 1987, 10, 488-496.
Jurasz, et al., "Matrix Metalloproteinase 2 in Tumor Cell-induced Platelet Aggregation: Regulation by Nitric Oxide," Cancer Research, 2001, 61, 376-382.
Kharitonenkov et al., "FGF-21 as a novel metabolic regulator," J Clin Invest. 2005, 115(6):1627-35.
Kopf, et al., "Impaired immune and acute-phase responses in interleukin-6-deficient mice," Nature, 1994, 368, 339-342.
Kossakowska, et al., "Interleukin-6 regulation of matrix metalloproteinase MMP-2 and MMP-9 and tissue inhibitor of metalloproteinase TIMP-1 expression in malignant non-Hodgkin's lymphomas," Blood, 1999, 94, 2080-2089.
Kotton et al., "A novel stem-cell population in adult liver with potent hematopoietic-reconstitution activity" Blood, 2005, 106,1574-1580.
Kovalovich et al., "Interleukin-6 protects against Fas-mediated death by establishing a critical level of anti-apoptotic hepatic proteins FLIP, Bcl-2, and Bcl-xL," J Biol. Chem. 2001, 276, 26605-26613.
Kucia et al., "Cells expressing early cardiac markers reside in the bone marrow and are mobilized into the peripheral blood after myocardial infarction," Circ. Res. 2004, 95, 1191-1199.
Lagasse et al., "Purified hematopoietic stem cells can differentiate into hepatocytes in vivo," Nat Med. 2000, 6, 1229-1234.
Laugwitz et al., "Postnatal isl1+cardioblasts enter fully differentiated cardiomyocyte lineages," Nature, 2005, 433, 647-653.

\* cited by examiner

FIGURE 21

A.  Amino Acid Sequence of Human AGP2 (SEQ ID NO:11)

```
  1 malswvltvl sllplleaqi plcanlvpvp itnatldrit gkwfyiasaf rneeynksvq
 61 eiqatffyft pnktedtifl reyqtrqnqc fynssylnvq rengtvsrye ggrehvahll
121 flrdtktlmf gsylddeknw glsfyadkpe ttkeqlgefy ealdclcipr sdvmytdwkk
181 dkceplekqh ekerkqeege s
```

B.  Nucleic Acid Sequence of Human AGP2 (SEQ ID NO:12)

```
  1 atggcgctgt cctgggttct tacagtcctg agcctcctac ctctgctgga agcccagatc
 61 ccattgtgtg ccaacctagt accggtgccc atcaccaacg ccaccctgga ccggatcact
121 ggcaagtggt tttatatcgc atcggccttt cgaaacgagg agtacaataa gtcggttcag
181 gagatccaag caaccttctt ttactttacc cccaacaaga cagaggacac gatctttctc
241 agagagtacc agacccgcca gaaccagtgc ttctataact ccagttacct gaatgtccag
301 cgggagaatg ggaccgtctc cagatacgag ggaggccgag aacatgttgc tcacctgctg
361 ttccttaggg acaccaagac cttgatgttt ggttcctacc tggacgatga agaaaactgg
421 gggctgtctt tctatgctga caagccagag acgaccaagg agcaactggg agagttctac
481 gaagctctcg actgcttgtg cattcccagg tcagatgtca tgtacaccga ctggaaaaag
541 gataagtgtg agccactgga gaagcagcac gagaaggaga ggaaacagga ggaggggaa
601 tcctag
```

FIGURE 22

A. Amino Acid Sequence of Human BMPER (SEQ ID NO:13)

MLWFSGVGALAERYCRRSPGITCCVLLLLNCSGVFMSLASSFLTGSVAKCENEGEVLQIPFITDNPCIMCVLNKEVTCKREKCPVL
SRDCALAIKQRGACCEQCKGCTYEGNTYNSSFKWQSPAEPCVLRQCQEGVVTESGVRCVVHCKNPLEHLGMCCPTCPGCVFEGVQYQ
EGEEFQPEGSKCTKCSCTGGRTQCVREVCPILSCPQHLSHIPPGQCCPKCLGQRKVFDLPFGSCLFRSDVYDNGSSPLYDNCTACTC
RDSTVVCKRKCSHPGGCDQGQEGCCEECLLRVPPEDIKVCKFGNKIFQDGEMWSSINCTICACVKGRTECRNKQCIPISSCPQGKIL
NRKGCCPICTEKPGVCTVFGDPHYNTFDGRTPNFQGTCQYVLTKDCSSPASPFQVLVKNDARPTRSFSWTKSVELVLGESRVSLQQH
LTVRWNGSRIALPCRAPHFHIDLDGYLLKVTTKAGLEISWDGDSFVEVMAAPHLKGKLCGLCGNYNGHKRDDLIGGDGNFKFDVDDF
AESWRVESNEFCNRPQRKPVPELCQGTVKVKLRAHRECQKLKSWEFQTCHSTVDYATFYRSCVTDMCECPVHKNCYCESFLAYTRAC
QREGIKVHWEPQQNCAATQCKHGAVYDTCGPGCIKTCDNWNEIGPCNKPCVAGCHCPANLVLHKGRCIKPVLCPQR

B. Nucleic Acid Sequence of Human BMPER (SEQ ID NO:14)

```
   1 atgctctggt tctccggcgt cggggctctg gctgagcgtt actgccgccg ctcgcctggg
  61 attacgtgct gcgtcttgct gctactcaat tgctcggggg tccccatgtc tctggcttcc
 121 tccttcttga caggttctgt tgcaaaatgt gaaaatgaag gtgaagtcct ccagattcca
 181 tttatcacag acaacccttg cataatgtgt gtctgcttga acaaggaagt gacatgtaag
 241 agagagaagt gccccgtgct gtcccgagac tgtgccctgg ccatcaagca gaggggagcc
 301 tgttgtgaac agtgcaaagg ttgcacctat gaaggaaata cctataacag ctccttcaaa
 361 tggcagagcc cggctgagcc ttgtgttcta cgccagtgcc aggagggcgt tgtcacagag
 421 tctggggtgc gctgtgttgt tcattgtaaa aaccctttgg agcatctggg aatgtgctgc
 481 cccacatgtc caggctgtgt gtttgagggt gtgcagtcct aagaaggcga ggaatttcag
 541 ccagaaggaa gcaaatgtac caagtgttcc tgcactggag gcaggacaca atgtgtgaga
 601 gaagtctgtc ccattctctc ctgtcccag cacttagtc acataccccc aggacagtgc
 661 tgccccaaat gtttgggtca gaggaaagtg ttgacctc cttggggag ctgcctcttt
 721 cgaagtgatg tttatgacaa tggatcctca tttctgtacg ataactgcac agcttgtacc
 781 tgcagggact ctactgtgt tgcaagagg aagtgctcc accctggtgg ctgtgaccaa
 841 ggccaggagg gctgttgtga agagtgcctc ctacgagtgc cccagaaga catcaaagta
 901 tgcaaatttg gcaacaagat tttccaggat ggagagatgt ggtcctctat caattgtacc
 961 atctgtgctt gtgtgaaagg caggacggag tgtcgcaata gcagtgcat tccatcagt
1021 agctgcccac agggcaaaat tctcaacaga aaggatgct gtcctatttg cactgaaaag
1081 cccggcgttt gcacggtgtt tggagatccc cactacaaca cttttgacgg tcggacattt
1141 aactttcagg ggacgtgtca gtacgttttg acaaaagact gctcctcccc tgcctcgccc
1201 ttccagggtgc tggtgaagaa cgacgcccgc cggacacgct ccttctcgtg gaccaagtcg
1261 gtggagctgg tgctgggcga gagcagggtc agcctgcagc agcacctcac cgtgcgctgg
1321 aacgctcgc gcatcgcgct ccctgccgc gcgccacact tccacatcga cctggatggc
1381 tacctcttga aagtgaccac caaagcaggt ttggaaatat cttgggatgg agacagtttt
1441 gtagaagtca tggctgcgc gcatctcaag ggcaagctct gtggtctttg tggcaactac
1501 aatggacata aacgtgatga cttaattggt ggagatgaa acttcaagtt tgatgtggat
1561 gactttgctg aatcttggag ggtggagtcc aatgagttct gcaacagacc tcagagaaag
1621 ccagtgcctg aactgtgtca agggacagtc aaggtaaagc tccgggccca tcgagaatgc
1681 caaaagctca aatcctggga gttcagacc tgccactcga ctgtggacta cgccactttc
1741 taccgtgcct gtgtgacaga catgtgtgaa tgtccagtgc ataaaaactg ttattgcgag
1801 tcatttttgg catataccc ggcctgccag agagagggca tcaaagtcca ctgggagcct
1861 cagcagaatt gtgcagccac ccagtgtaag catggtgctg tgtacgatac ctgtggtccg
1921 ggatgtatca agacgtgtga caattggaat gaaattggtc catgcaacaa gccgtgcgtt
1981 gctgggtgcc actgtccagc aaacttggtc cttcacaagg gaaggtgcat caagccagtc
2041 ctttgtcccc agcggtga
```

FIGURE 23

A. Amino Acid Sequence of Human FGF21 (SEQ ID NO:15)

MDSDETGFEHSGLWVSVLAGLLLGACQAHPIPDSSPLLQFGGQVRQRYLYTDDAQQTEAHLEIREDGTVGGAADQSPESLLQLKALK
PGVIQILGVKTSRFLCQRPDGALYGSLHFDPEACSFRELLLEDGYNVYQSEAHGLPLHLPGNKSPHRDPAPRGPARFLPLPGLPPAL
PEPPGILAPQPPDVGSSDPLSMVGPSQGRSPSYAS

B. Nucleic Acid Sequence of Human FGF21 (SEQ ID NO:16)

```
  1 ctgtcagctg aggatccagc cgaaagagga gccaggcact caggccacct gagtctactc
 61 acctggacaa ctggaatctg gcaccaattc taaaccactc agcttctccg agctcacacc
121 ccggagatca cctgaggacc cgagccattg atggactcgg acgagaccgg gttcgagcac
181 tcaggactgt gggtttctgt gctggctggt cttctgctgg gagcctgcca ggcacacccc
241 atccctgact ccagtcctct cctgcaattc gggggccaag tccggcagcg gtacctctac
301 acagatgatg cccagcagac agaagcccac ctggagatca gggaggatgg gacggtgggg
361 ggcgctgctg accagagccc cgaaagtctc ctgcagctga agccttgaa gccgggagtt
421 attcaaatct gggagtcaa gacatccagg ttcctgtgcc agcggccaga tggggccctg
481 tatggatcgc tccactttga ccctgaggcc tgcagcttcc gggagctgct tcttgaggac
541 ggatacaatg tttaccagtc cgaagcccac ggcctcccgc tgcacctgcc agggaacaag
601 tccccacacc gggaccctgc acccgagga ccagctcgct tcctgccact accaggcctg
661 cccccgcac tccggagcc accggaatc ctggccccc agccccga tgtgggctcc
721 tcggaccctc tgagcatggt gggaccttcc cagggccgaa gcccagcta cgcttcctga
781 agccagaggc tgtttactat gacatctcct ctttatttat taggttattt atcttattta
841 tttttttatt tttcttactt gagataataa agagttccag aggagaaaaa aaaaaaaaaa
901 aaaaaaaaaa aaaaaaaaaa aaaaaaaaaa aaaaaaaaaa
```

FIGURE 24

A. Amino Acid Sequence of Human NRG4 (SEQ ID NO:17)

MPTDHEEPCGPSHKSFCLNGGLCYVIPTIPSPFCRCVENYTGARCEEVFLPGSSIQTKSNLFEAFVALAVLVTLIIGAFYFLCRKGH
FQRASSVQYDINLVETSSTSAHHSHEQH

B. Nucleic Acid Sequence of Human NRG4 (SEQ ID NO:18)

```
  1 atgccaacag atcacgaaga gccctgtggt cccagtcaca agtcgttttg cctgaatggg
 61 gggctttgtt atgtgatacc tactattccc agcccatttt gtaggtgcgt tgaaaactat
121 acaggagctc gttgtgaaga ggtttttctc ccaggctcca gcatccaaac taaaagtaac
181 ctgtttgaag cttttgtggc attggcggtc ctagtaacac ttatcattgg agccttctac
241 ttcctttgca ggaaaggcca ctttcagaga gccagttcag tccagtatga tatcaacctg
301 gtagagacga gcagtaccag tgcccaccac agtcatgaac aacactga
```

C. Amino Acid Sequence of Human NRG4 isoform B2 (SEQ ID NO:19)

MPTDHEEPCGPSHKSFCLNGGLCYVIPTIPSPFCG

D. Nucleic Acid Sequence of Human NRG4 isoform B2 (SEQ ID NO:20)

```
  1 atgccaacag atcacgaaga gccctgtggt cccagtcaca agtcgttttg cctgaatggg
 61 gggctttgtt atgtgatacc tactattccc agcccatttt gtggttaatg aggaactgat
121 taatgaggga accaatag
```

E. Amino Acid Sequence of Human NRG4 isoform B3 (SEQ ID NO:21)

MPTDHEEPCGLSHKSFCLNGGLCYVIPTIPSPFCSLHENENDNNEDLYDDLLPLNE

F. Nucleic Acid Sequence of Human NRG4 isoform B3 (SEQ ID NO:22)

```
  1 atgccaacag atcacgaaga gccctgtggt ctcagtcaca agtcgttttg cctgaatggg
 61 gggctttgtt atgtgatacc tactattccc agcccatttt gtagtctaca cgaaaatgaa
121 aacgacaaca atgaagacct ttatgatgat ctacttccac ttaatgaata gtaa
```

G. Amino Acid Sequence of Human NRG4 isoform A2 (SEQ ID NO:23)

MPTDHEEPCGPSHKSFCLNGGLCYVIPTIPSPFCRCVENYTGARCEEVFLPGSSIQTKSNLFEAFVALAVLVTLIIGAFYFLCRCGN
TCM

H. Nucleic Acid Sequence of Human NRG4 isoform A2 (SEQ ID NO:24)

```
  1 atgccaacag atcacgaaga gccctgtggt cccagtcaca agtcgttttg cctgaatggg
 61 gggctttgtt atgtgatacc tactattccc agcccatttt gtaggtgcgt tgaaaactat
121 acaggagctc gttgtgaaga ggtttttctc ccaggctcca gcatccaaac taaaagtaac
181 ctgtttgaag cttttgtggc attggcggtc ctagtaacac ttatcattgg agccttctac
241 ttcctttgca ggtgtggtaa cacatgcatg tag
```

FIGURE 25

A.  Amino Acid Sequence of Human TFF3 (SEQ ID NO:25)

MLGLVLALLSSSSAEEYVGLSANQCAVPAKDRVDCGYPHVTPKECNNRGCCFDSRIPGVPWCFKPLQEAECTF

B.  Nucleic Acid Sequence of Human TFF3 (SEQ ID NO:26)

```
  1 atgctgggc tggtcctggc cttgctgtcc tccagctctg ctgaggagta cgtgggcctg
 61 tctgcaaacc agtgtgccgt gccagccaag gacagggtgg actgcggcta ccccatgtc
121 accccaagg agtgcaacaa ccggggctgc tgctttgact ccaggatccc tggagtgcct
181 tggtgtttca gcccctgca ggaagcagaa tgcaccttct ga
```

FIGURE 26

Amino Acid Sequence of Alternate Version of Human FGF21 (SEQ ID NO:27)

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

US 8,889,625 B2

CARDIOPROTECTIVE ROLE OF HEPATIC CELLS AND HEPATOCYTE SECRETORY FACTORS IN MYOCARDIAL ISCHEMIA

The present application claims priority to U.S. Provisional Application Ser. No. 61/224,691, filed Jul. 10, 2009, which is herein incorporated by reference in its entirety.

This invention was made with government support under grant no. BES-0401781 awarded by the National Science Foundation. The government has certain rights in the invention.

FIELD OF THE INVENTION

The present invention relates to methods, compositions, and systems for treating a subject at risk for, with, or suspected of having, myocardial ischemia using hepatocyte secretory factors (e.g., AGP2, BMPER, FGF21, NRG4, and/or TFF3) or using factors that promote liver cell migration to ischemic myocardial tissue (e.g., IL-6 and/or MMP-2).

BACKGROUND

Myocardial ischemia is a disorder often induced by coronary arterial stenosis or occlusion, resulting in myocardial infarction and dysfunction, a major cause of human death. There are various technologies developed for the treatment of myocardial ischemia, including coronary arterial reconstruction, angioplasty, and stenting as well as cell-based therapies such as transplantation of embryonic and adult stem cells (bone marrow and cardiac resident stem cells) and induction of bone marrow cell mobilization. The first three technologies (coronary arterial reconstruction, angioplasty, and stenting) have been well established and commonly used for the treatment of human myocardial ischemia. However, treatment based on these technologies often induces coronary arterial injury, resulting in restenosis of coronary arteries and reoccurrence of myocardial ischemia within 1 to 5 years.

SUMMARY OF THE INVENTION

The present invention provides methods, compositions, and systems for treating a subject at risk for, with, or suspected of having, myocardial ischemia using hepatocyte secretory factors (e.g., AGP2, BMPER, FGF21, NRG4, and/or TFF3) or using factors that promote liver cell migration to ischemic myocardial tissue (e.g., IL-6 and/or MMP-2).

In some embodiments, the present invention provides methods of treating a subject at risk for, having, or suspected of having myocardial ischemia comprising: administering a composition to a subject at risk for, having, or suspected of having, myocardial ischemia, where the composition comprises at least one isolated hepatocyte secretory factor. The secretory factor can be a factor whose serum concentration is increased in response to myocardial ischemia. In certain embodiments, the administration reduces myocardial injury in the subject. In further embodiments, the at least one isolated hepatocyte secretory factor is selected from the group consisting of: α-1-acid glycoprotein 2 (AGP2) or a biologically active fragment or variant thereof, bone morphogenetic protein binding endothelial regulator (BMPER) or a biologically active fragment or variant thereof, fibroblast growth factor 21 (FGF21) or a biologically active fragment or variant thereof, neuregulin 4 (NRG4) or a biologically active fragment or variant thereof, and trefoil factor 3 (TFF3) or a biologically active fragment or variant thereof.

In certain embodiments, the at least one isolated hepatocyte secretory factor is administered at a dosage of 5 ug/kg-75 ug/kg (e.g., 5 µg/kg ... 10 µg/kg ... 15 µg/kg ... 20 µg/kg ... 25 µg/kg ... 30 µg/kg ... 35 µg/kg ... 40 µg/kg ... 45 µg/kg ... 50 µg/kg ... 55 µg/kg ... 60 µg/kg ... 65 µg/kg ... 75 µg/kg). In some embodiments, the at least one isolated hepatocyte secretory factor is administered at a dosage of 15 µg/kg-50 µg/kg. In certain embodiments, the at least one isolated hepatocyte secretory factor is administered at a dosage of about 1.0 to 15.0 mgs (e.g., 1.0 mg ... 3.0 mg ... 5.0 mg ... 7.5 mg ... 10.0 mg ... or 15.0 mg or more). In certain embodiments, the at least one isolated hepatocyte secretory factor is administered at a dosage of 15 µg/kg-50 µg/kg. In additional embodiments, the at least one isolated hepatocyte secretory factor comprises two, three, four, or five isolated hepatocyte secretory factors selected from the group consisting of: α-1-acid glycoprotein 2 (AGP2) or biologically active fragment or variant thereof, bone morphogenetic protein binding endothelial regulatory (BMPER) or biologically active fragment or variant thereof, fibroblast growth factor 21 (FGF21) or biologically active fragment or variant thereof, neuregulin 4 (NRG4) or a biologically active fragment or variant thereof, and trefoil factor 3 (TFF3) or a biologically active fragment or variant thereof.

In other embodiments, the at least one isolated hepatocyte secretory factor comprises bone morphogenetic protein binding endothelial regulatory (BMPER) or a biologically active fragment or variant thereof. In further embodiments, BMPER is administered at a dosage of 15 µg/kg-35 µg/kg (e.g., about 25 ug/kg; or at a total dose of about 2.0-3.0 mg).

In certain embodiments, the at least one isolated hepatocyte secretory factor comprises isolated hepatocyte secretory factors: α-1-acid glycoprotein 2 (AGP2) or a biologically active fragment or variant thereof, bone morphogenetic protein binding endothelial regulatory (BMPER) or a biologically active fragment or variant thereof, fibroblast growth factor 21 (FGF21) or a biologically active fragment or variant thereof, neuregulin 4 (NRG4), and trefoil factor 3 (TFF3) or a biologically active fragment or variant thereof. In additional embodiments, the isolated hepatocyte secretory factors are administered in about the relative ratio of 1:1:1.38:1.23:1.55 for AGP2:BMPER:FGF21: NRG4:TFF3.

In some embodiments, the subject is a human and the at least one isolated hepatocyte secretory factor is a human hepatocyte secretory factor or active fragment or variant thereof. The at least one isolated hepatocyte secretory factor can be administered intravenously, orally, or by intra-cardiac administration.

In certain embodiments, a composition is provided comprising: a) a first component comprising a first isolated hepatocyte secretory factor that is selected from the group consisting of: α-1-acid glycoprotein 2 (AGP2) or a biologically active fragment or variant thereof, bone morphogenetic protein binding endothelial regulatory (BMPER) or a biologically active fragment or variant thereof, fibroblast growth factor 21 (FGF21) or a biologically active fragment or variant thereof, neuregulin 4 (NRG4) or a biologically active fragment or variant thereof, and trefoil factor 3 (TFF3) or a biologically active fragment or variant thereof; and b) a second component selected from the group consisting of: i) a second isolated hepatocyte secretory factor, different from the first isolated hepatoctyle secretory factor, selected from the list in part a); ii) at least one cardiac drug that is not a hepatocyte secretory factor; iii) a binder composition configured for forming a pill; and iv) a physiologically tolerable buffer.

In some embodiments, the at least one isolated hepatocyte secretory factor is present in the composition in an amount from about 1.0 mg to 15.0 mg (e.g., 1.0 mg . . . 3.0 mg . . . 5.0 mg . . . 8.0 mg . . . 12 mg . . . 15 mg). In further embodiments, the first component comprise BMPER or a biologically active fragment or variant thereof.

In some embodiments, the present invention provides compositions or systems comprising: at least one isolated hepatocyte secretory factor present in the composition in an amount from about 1.0 mg to 15.0 mg, wherein the at least one isolated hepatocyte secretory factor is selected from the group consisting of: i) α-1-acid glycoprotein 2 (AGP2) or a biologically active fragment or variant thereof; ii) bone morphogenetic protein binding endothelial regulatory (BMPER) or a biologically active fragment or variant thereof; iii) fibroblast growth factor 21 (FGF21) or a biologically active fragment or variant thereof; iv) neuregulin 4 (NRG4) or a biologically active fragment or variant thereof; and v) trefoil factor 3 (TFF3) or a biologically active fragment or variant thereof. In particular embodiments, the at least one isolated hepatocyte secretory factor is BMPER or a biologically active fragment or variant thereof.

In some embodiments, the present invention provides methods of treating a subject at risk for, having, or suspected of having, myocardial ischemia comprising administering to the subject a reagent that increases liver cell migration to myocardial tissue above a level present in the absence of the reagent.

In certain embodiments, the present invention provides methods of treating a subject at risk or, having, or suspected of having, myocardial ischemia comprising: a) providing; i) a subject comprising a heart, wherein the heart has, is at risk for, or is suspected of having, ischemic myocardial tissue, and ii) a composition comprising a reagent including, but not limited to, hepatocyte growth factor, a biologically active fragment of the hepatocyte growth factor, a nucleic acid construct encoding hepatocyte growth factor or biologically active fragment, or a hepatocyte growth factor mimetic; and b) administering the composition to the subject.

In certain embodiments, the reagent comprises the hepatocyte growth factor (e.g., human hepatocyte growth factor, such as, for example, the protein encoded by accession numbers NM_000601, NM_001010931, NM_001010932, NM_001010933 or NM_001010934). In certain embodiments, the reagent is a nucleic acid construct encoding human hepatocyte growth factor (e.g., as shown in accession number NM_000601) or a biologically active fragment thereof. In other embodiments, the reagent comprises the biologically active fragment of the hepatocyte growth factor (e.g., a portion of hepatocyte growth factor that is determined to help reduce ischemia in cardiac tissue). In further embodiments, the reagent comprises the hepatocyte growth factor mimetic (e.g., a small molecule found to have the same or similar impact on ischemic myocardial tissue as hepatocyte growth factor).

In further embodiments, the present invention provides methods of treating a subject at risk for, having, or suspected of having, myocardial ischemia comprising administering to the subject a composition comprising a plurality of liver cells. In particular embodiments, the liver cells are initially obtained from the subject. In other embodiments, the liver cells over-express hepatocyte secretory factors (i.e., express higher levels of hepatocyte secretory factors than normally expressed by such cells in patients without myocardial ischemia). In further embodiments, the liver cells comprise hepatocytes (e.g., human hepatocytes). In some embodiments, the liver cells comprise biliary epithelial cells (e.g., human biliary epithelial cells).

In certain embodiments, the subject is someone without ischemic myocardial tissue injury, but is at risk for such injury (e.g., the composition is administered prophylacticly to prevent anticipated ischemic injury).

In additional embodiments, the present invention provides compositions comprising: a) a first reagent that increases liver cell migration to ischemic myocardial tissue in a subject above the level that would be present in the absence of the first reagent; and b) a second reagent configured to increase the concentration of the first reagent at the ischemic myocardial tissue above the level that would be present at the ischemic myocardial tissue in the absence of the second reagent. In certain embodiments, the second reagent comprises unilamellar liposomes (see, e.g., U.S. Pat. No. 5,593,688, herein incorporated by reference). In other embodiments, at least a portion of the first reagent is located inside of at least a portion of the second reagent.

In other embodiments, the present invention provides systems comprising: a) a first reagent that increases liver cell migration to ischemic myocardial tissue in a subject above the level that would be present in the absence of the first reagent; and b) at least one cardiac medical device or at least one cardiac drug. In further embodiments, the cardiac medical device comprises a defibrillator.

In additional embodiments, the present invention provides systems comprising: a) a first reagent that increases liver cell migration to ischemic myocardial tissue in a subject above the level that would be present in the absence of the first reagent; and b) a syringe or syringe vial, wherein the first reagent is located inside the syringe or the syringe vial.

In further embodiments, the present invention provides compositions comprising: a) a first reagent including, but not limited to, hepatocyte growth factor, a biologically active fragment of the hepatocyte growth factor, or a hepatocyte growth factor mimetic; and b) a second reagent configured to increase the concentration of the first reagent at the ischemic myocardial tissue above the level that would be present at the ischemic myocardial tissue in the absence of the second reagent. In further embodiments, the second reagent comprises unilamellar liposomes. In other embodiments, at least a portion of the first reagent is located inside of at least a portion of the second reagent.

In further embodiments, the present invention provides systems comprising: a) a first reagent selected from the group consisting of: hepatocyte growth factor, a biologically active fragment of the hepatocyte growth factor, or a hepatocyte growth factor mimetic; and b) at least one cardiac medical device or at least one cardiac drug. In other embodiments, the cardiac medical device comprises a defibrillator.

In other embodiments, the present invention provides systems comprising: a) a first reagent selected from the group consisting of: hepatocyte growth factor, a biologically active fragment of the hepatocyte growth factor, or a hepatocyte growth factor mimetic; and b) a syringe or syringe vial, wherein the first reagent is located inside the syringe or the syringe vial.

In some embodiments, the present invention provides composition comprising: a) a plurality of isolated liver cells, wherein the liver cells over-express hepatocyte secretory factor; and b) a physiologically tolerable buffer or saline solution.

In additional embodiments, the present invention provides systems comprising: a) a composition comprising a plurality of isolated liver cells (e.g., wherein the liver cells over-express hepatocyte secretory factor); and b) at least one cardiac medical device or at least one cardiac drug. In further embodiments, the cardiac medical device comprises a defibrillator.

In further embodiments, the present invention provides systems comprising: a) a composition comprising a plurality of isolated liver cells, wherein the liver cells over-express hepatocyte secretory factors; and b) a syringe or syringe vial, wherein the first reagent is located inside the syringe or the syringe vial. In further embodiments, the composition further comprises a physiologically tolerable buffer.

In some embodiments, the first reagent comprises IL-6 (e.g., human IL-6, such as that encoded by accession number NM_000600). In further embodiments, the first reagent comprises a biologically active fragment of an IL-6 protein (e.g., a fragment of IL-6 that is able to promote liver cell migration to myocardial tissue). In further embodiments, the first reagent comprises a IL-6 mimetic (e.g., a small molecule that promotes liver cell migration to myocardial tissue). In other embodiments, the first reagent comprises a nucleic acid construct configured to express IL-6 or a biologically active fragment thereof.

In certain embodiments, the first reagent comprises MMP-2 (e.g., human MMP-2, such as that represented by accession number NM_001127891). In some embodiments, the first reagent comprises a biologically active fragment of an MMP-2 protein (e.g., a fragment of MMP-2 that is able to promote liver cell migration to myocardial tissue). In further embodiments, the first reagent comprises an MMP-2 mimetic (e.g., a small molecule that promotes liver cell migration to myocardial tissue). In further embodiments, the first reagent comprises a nucleic acid construct configured to express MMP-2 or a biologically active fragment thereof (e.g., wherein the nucleic acid construct comprises at least a portion of the nucleic acid sequence shown in accession number NM_001127891).

In particular embodiments, the subject is a mammal. In other embodiments, the subject is a human. In some embodiments, the subject is diagnosed as having myocardial ischemia. In further embodiments, the administering comprises intravenous administration. In further embodiments, the administering comprises intra-liver administration. In some embodiments, the administering comprises intra-heart administration. In particular embodiments, the liver cells comprise hepatocytes. In additional embodiments, the liver cells comprise biliary epithelial cells.

In other embodiments, the first reagent comprises one or more cellular factors isolated from liver cells, such as cellular factors found to be up-regulated or over-expressed in liver cells of ischemic subjects (e.g., hepatoctye secretory factors). In certain embodiments, a micro-array is performed to determine which cellular factors are over-expressed or up-regulated in such liver cells, with such identified factors serving as the first reagent in the methods, compositions, and systems of the present invention.

In some embodiments, the administering results in increased mechanical performance of the heart (e.g., as measured by echocardiography and dp/dt). In further embodiments, the administering results in the subject being diagnosed as having a reduction in myocardial infarction. In other embodiments, the administering results in at least 5% increase in liver cell migration to the ischemic myocardial tissue (e.g., at least 5% . . . 10% . . . 50% . . . 100% . . . 150% . . . 200% . . . 1000% or more).

DESCRIPTION OF THE FIGURES

FIG. 21 shows (A) the amino acid sequence of human AGP2 (SEQ ID NO:11), and (B) the nucleic acid sequence of human AGP2 (SEQ ID NO:12).

FIG. 22 shows (A) the amino acid sequence of human BMPER (SEQ ID NO:13), and (B) the nucleic acid sequence of human BMPER (SEQ ID NO:14).

FIG. 23 shows (A) the amino acid sequence of human FGF21 (SEQ ID NO:15), and (B) the nucleic acid sequence of human FGF21 (SEQ ID NO:16).

FIG. 24 shows (A) the amino acid sequence of human NRG4 (SEQ ID NO:17), (B) the nucleic acid sequence of human NRG4 (SEQ ID NO:18), (C) the amino acid sequence of human NRG4 isoform B2 (SEQ ID NO:19), (D) the nucleic acid sequence of human NRG4 isoform B2 (SEQ ID NO:20), (E) the amino acid sequence of human NRG4 isoform B3 (SEQ ID NO:21), (F) the nucleic acid sequence of human NRG4 isoform B3 (SEQ ID NO:22), (G) the amino acid sequence of human NRG4 isoform A2 (SEQ ID NO:23), and (H) the nucleic acid sequence of human NRG4 isoform A2 (SEQ ID NO:24).

FIG. 25 shows (A) the amino acid sequence of human TFF3 (SEQ ID NO:25), and (B) the nucleic acid sequence of human TFF3 (SEQ ID NO:26).

FIG. 26 shows the amino acid sequence of an alternate version of human FGF21 (SEQ ID NO:27), as described in U.S. Pat. Pub. 20090305986, which is herein incorporated by reference.

DETAILED DESCRIPTION

Figure 1:
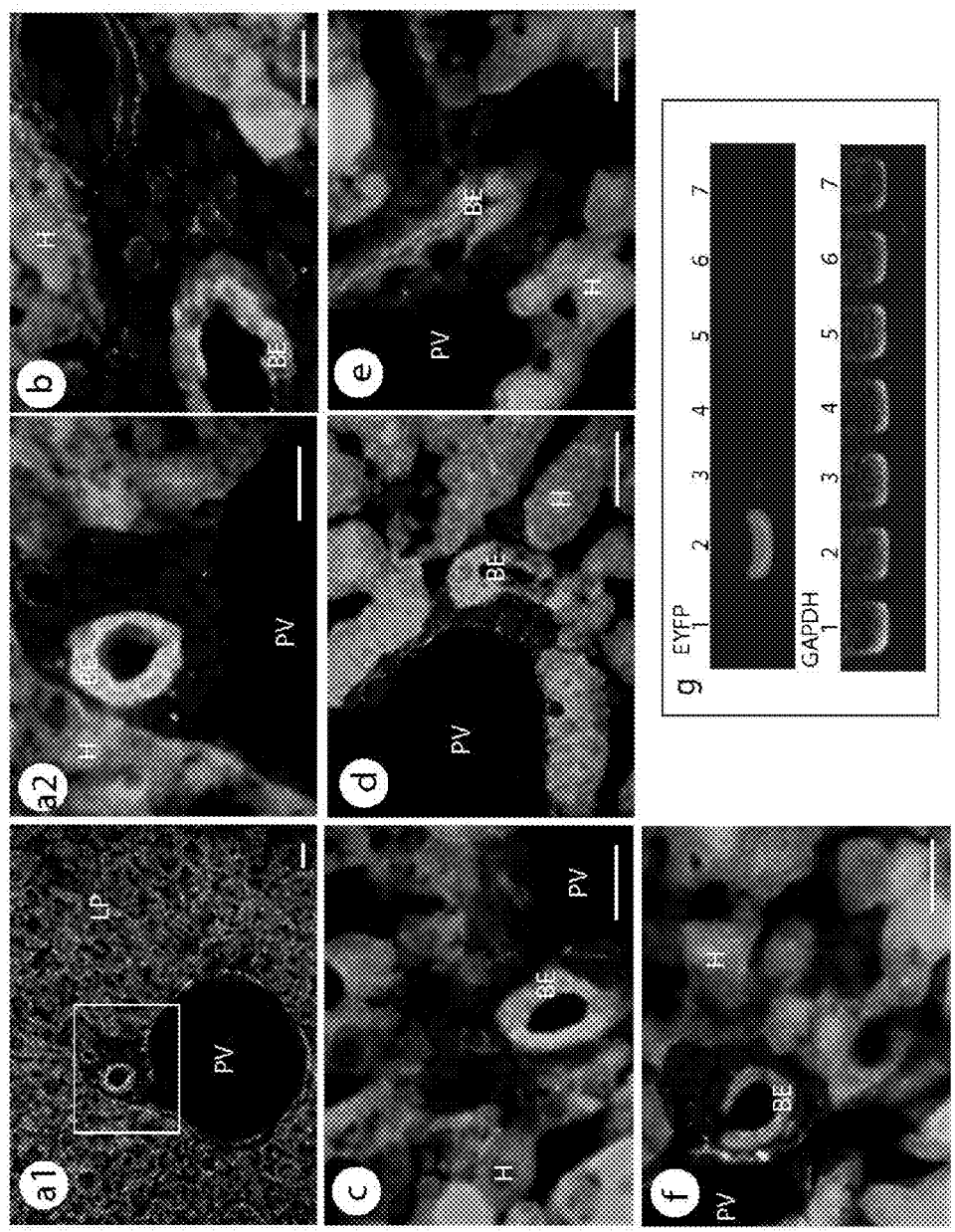
FIG. 1. Characterization of the Cre-EYFP mouse model. (a-d) Fluorescence micrographs showing the expression of EYFP in hepatocytes (H) and biliary epithelial cells (BE), the expression of CK19 in biliary epithelial cells (panel a), and the expression of CD45 (red, panel b), CD11b (red, panel c), and Sca-1 (red, panel d) in periductular cells of the liver of sham control Cre-EYFP mice. Panel a2 is a magnified image of the area (white rectangle) selected from a1. (e, f) Fluorescence micrographs showing the lack of c-Kit (panel e) and CD34 (panel f) expression in the liver of sham Cre-EYFP mice. For panels a-f, EYFP+ hepatocytes (H) and biliary epithelial cells (BE) are shown, LP is liver parenchyma, PV is portal venule, and the scale bars are 10 um. (g) RT-PCR analysis of the relative level of EYFP mRNA in hepatic cells derived from the liver of wild-type mice (lane 1) and Cre-EYFP mice (lane 2); CD45+ cells derived from the liver (lane 3), circulating blood (lane 4), bone marrow (lane 5), and ischemic lesion of myocardium (lane 6) of Cre-EYFP mice; and Sca-1+ cells derived from the liver of Cre-EYFP mice (lane 7). (h) One-dimensional cytometry analysis of EYFP+ cells derived from the liver and selected organs of Cre-EYFP mice as well as the liver of C57BL/6J mice. A standard level of fluorescence intensity (the left side of the red rectangle) was established from the hepatic cells of Cre-EYFP mice as described in the method section and used for assessing the population of EYFP-positive cells from other organs. The fraction shown in each panel represents the mean and standard deviation of the EYFP-positive cell population from 6 tests for each organ. (i) Two-dimensional cytometry analyses demonstrating the lack of CD45, CD11b, Sca-1, or c-Kit expression in EYFP+ cells derived from the liver of sham Cre-EYFP mice.
Figure 1:
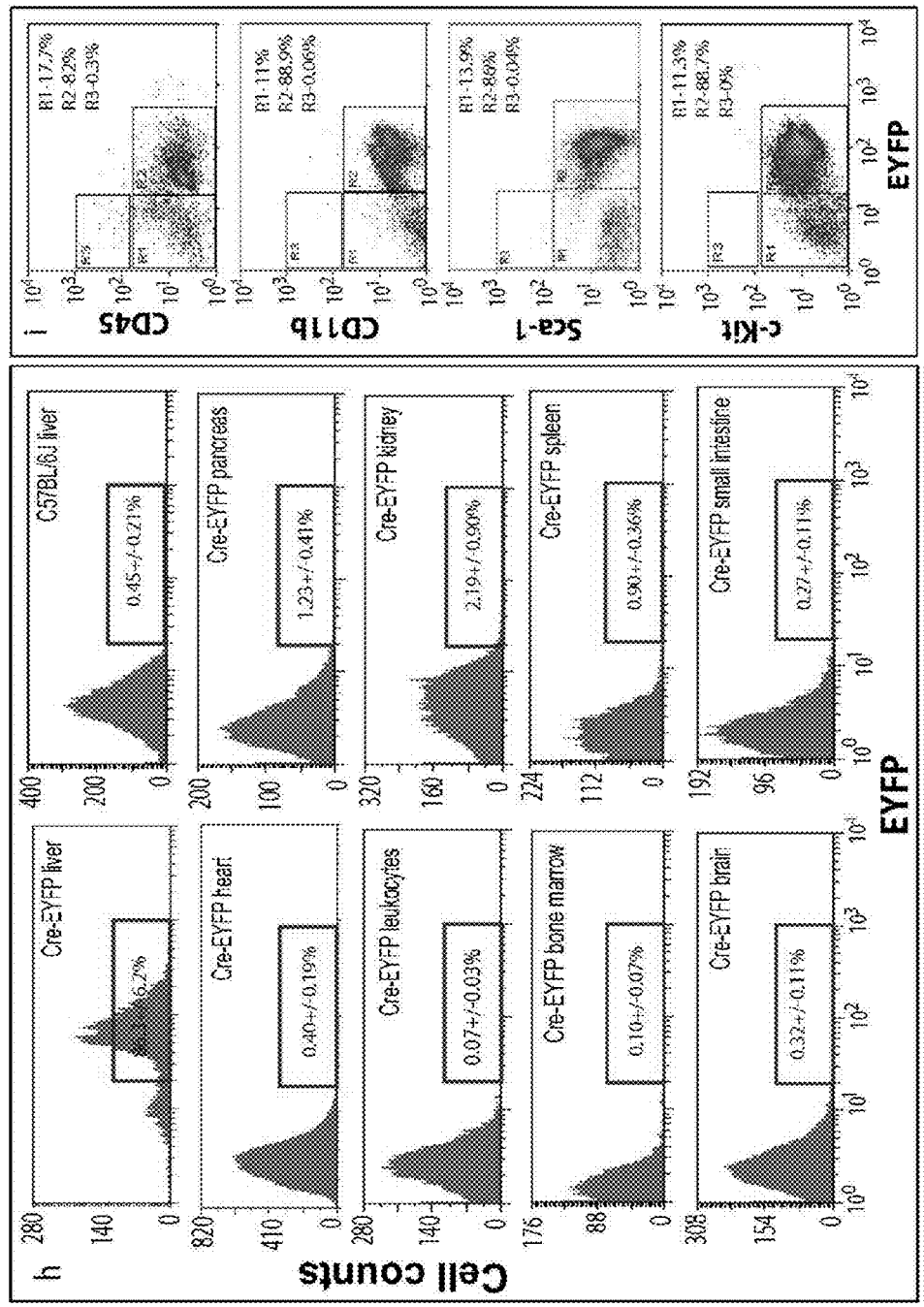

The present invention provides methods, compositions, and systems for treating a subject at risk for, with, or suspected of having, myocardial ischemia using hepatocyte secretory factors (e.g., AGP2, BMPER, FGF21, NRG4, and/or TFF3) or using factors that promote liver cell migration to ischemic myocardial tissue (e.g., IL-6 and/or MMP-2). The present invention also provides methods, compositions, and systems that promote ischemic myocardial tissue repair using hepatocyte growth factor (e.g., administering hepatocyte growth factor, or liver cells over-expressing hepatocyte growth factor, to a subject suspected of having, or at risk for, myocardial ischemia).

Myocardial ischemia induces cardiomyocyte injury and death, resulting in impairment of myocardial function. While the present invention is not limited to a any particular mechanism and an understanding of the mechanisms is not necessary to understand or practice the present invention, it is believed that adult cardiomyocytes possess a limited capacity of self-protection and regeneration, mechanisms involving non-myocardial cells may be activated to support the survival and performance of cardiomyocytes. Work conducted during the development of embodiments of the present invention demonstrated that hepatic cells, including hepatocytes and biliary epithelial cells, could be mobilized to the ischemic lesion of myocardium, contributing to cardioprotection against myocardial injury in an experimental model. The ischemic myocardium exhibited upregulation of interleukin (IL)-6, which induced hepatic cell expression of hepatocyte growth factor (HGF), a factor supporting myocardial survival and preventing myocardial death. IL-6 also stimulated leukocyte retention in the liver parenchyma and leukocyte upregulation of matrix metalloproteinase (MMP)-2, which mediated hepatic cell mobilization to the circulatory system. Mobilized hepatic cells could engraft to the ischemic myocardium and support myocardial survival and performance. While the present invention is not limited to any mechanism and an understanding of the mechanism is not necessary to practice the present invention, the increased survival and performance mediated by liver cells may be via expression of HGF by such liver cells.

While the present invention is not limited to any particular mechanism and an understanding of such mechanism is not necessary to practice the present invention, it is believed that hepatic cell-mediated cardioprotection is based on natural mobilization of hepatic cells in response to myocardial ischemia. It is believed that this is a process developed in mammalian systems for the protection of the heart against ischemic injury. As shown in the Examples below, when hepatic cell mobilization is suppressed by genetic knockout of interleukin-6 (IL-6, a cytokine mediating hepatic cell mobilization) in a mouse model, the degree of myocardial infarction is significantly increased, resulting in a higher rate of left ventricular rupture, compared to that in wild-type mice with a normal level of hepatic cell mobilization.

In certain embodiments, the present invention provides therapies based on mobilizing liver cells to a ischemic myocardial tissue. Exemplary therapies include, but are not limited to, enhancement of hepatic cell mobilization by administration (e.g., venous administration) of IL-6 (or molecule with similar activity) and administration (e.g., liver administration) of matrix metalloproteinase-2 (a proteinase directly mediating hepatic cell mobilization), and modulation of the cardioprotective function of hepatic cells and transplantation of hepatic cells to the venous system of patients with myocardial ischemia.

The Liver as an Organ for Cardioprotection

The liver has long been considered an organ that is responsible for metabolism, detoxification, bile secretion, and production of serum proteins. As a vital organ for controlling homeostasis, the liver has evolved with a unique self-protective function complete mass regeneration in response to chemical-induced liver injury and partial hepatectomy. Liver regeneration does not completely depend on differentiation of stem and progenitor cells, but involves proliferation of mature hepatic cells. The liver contains a large reserve of hepatocytes and biliary epithelial cells, which are quiescent under physiological conditions. In response to liver injury, more than 90% of these cells can be activated to enter the cell division cycle and proliferate, resulting in rapid liver regeneration. In contrast to the liver, the adult heart lacks the function of complete regeneration in myocardial injury.

Work conducted during development of embodiments of the present invention has shown that the liver is able to assist the heart in cardioprotection by mobilizing hepatic cells. Mobilized hepatic cells support the survival and performance of ischemic myocardium. As described in the Examples below, when hepatic cell mobilization was impaired, as found in the mouse model of interleukin-6 deficiency, myocardial injury, malfunction, and rupture were significantly intensified compared to control mice with a normal level of hepatic cell mobilization. The mobilization of hepatic cells represents a cardio-hepatic collaborative effort for cardioprotection in myocardial ischemia. Thus, the liver has evolved as an organ responsible not only for metabolism, detoxification, bile secretion, and protein production, but also for cardioprotection.

Hepatic Cell Mobilization

While the present invention is not limited to any particular mechanism and an understanding of the mechanism is not necessary to practice the present invention, it is believed that the induction of hepatic cell mobilization proceeds as follows. Myocardial ischemia induces IL-6 upregulation in the ischemic lesion, resulting in an increase in the serum level of IL-6. IL-6 can stimulate leukocyte adhesion to the hepatic vasculature and also induce leukocyte upregulation of MMP-2, a proteinase responsible for degradation of type IV and V collagen, gelatin, and elastin. MMP-2 in turn mediates hepatic cell mobilization. When myocardial injury is healed, IL-6 expression decreases in association with a reduction in leukocyte adhesion to the hepatic vasculature and leukocyte expression of MMP-2. As a result, hepatic cell mobilization reduces accordingly.

Hepatic Cell-Mediated Cardioprotection

While the present invention is not limited to any particular mechanism and an understanding of the mechanism is not necessary to practice the present invention, it is believed that hepatic cells can be mobilized to assist the heart in cardioprotection in ischemic injury as follows. It is believed that hepatocyte growth factor (HGF) mediates the cardioprotective effect of hepatic cells in myocardial ischemia. HGF is a growth factor that promotes cardiomyocyte survival (Nakamura et al., 2000), alleviates myocardial fibrosis (Li et al., 2003; Taniyama et al., 2000), and mobilizes resident stem cells to ischemic myocardium (Urbanek et al., 2005). As shown in the Examples below, this growth factor was upregulated in hepatic cells in response to IL-6 stimulation in myocardial ischemia, a process associated with hepatic cell mobilization. Given the fact that HGF expression was significantly enhanced in the ischemic lesion of myocardium following hepatic cell transplantation, it is believed that hepatic cell engraftment to the ischemic myocardium may contribute to HGF upregulation. This contribution was supported by observations in the Examples. First, HGF was not significantly upregulated in mice with impaired hepatic cell mobilization in IL-6$^{-/-}$ mice. Second, while transplantation of HGFexpressing hepatocytes derived from mice with myocardial ischemia to IL-6$^{-/-}$ mice induced significant HGF upregulation in the ischemic lesion of myocardium, transplantation of hepatocytes with significantly reduced HGF expression by HGF-siRNA transfection to IL-6$^{-/-}$ mice did not induce significant HGF upregulation. These observations support the contribution of hepatic cells to HGF upregulation in the ischemic lesion of myocardium. To demonstrate the role of HGF in mediating the cardioprotective effect of hepatic cells, HGF or anti-HGF antibody was administered to mice with myocardial ischemia. Administration of HGF significantly enhanced the survival and mechanical performance of ischemic myocardium. In contrast, administration of anti-HGF antibody, following transplantation of hepatocytes derived from mice with myocardial ischemia, significantly suppressed the cardioprotective effects of hepatic cells. These observations support the cardioprotective role of HGF in myocardial ischemia.

Hepatocyte Secretory Factors for Protection Against Myocardial Ischemia

In certain embodiments, the present invention provides systems, methods, and compositions for treating patients at risk for, having, or suspected of having, myocardial ischemia, with a composition comprises at least one isolated hepatocyte secretory factor whose serum concentration is increased in response to myocardial ischemia. In certain embodiments, the hepatocyte secretoary factor is selected from the group consisting of: α-1-acid glycoprotein 2 (AGP2) or a biologically active fragment or variant thereof, bone morphogenetic protein binding endothelial regulatory (BMPER) or a biologically active fragment or variant thereof, fibroblast growth factor 21 (FGF21) or a biologically active fragment or variant thereof, neuregulin 4 (NRG4) or a biologically active fragment or variant thereof, and trefoil factor 3 (TFF3) or a biologically active fragment or variant thereof.

Among the hepatocyte-upregulated secretory proteins, AGP2 is an acute-phase plasma protein upregulated in response to inflammatory mediators, such as IL-6 and TNF α (Fournier and Najet 2000), and is known to stimulate fibroblast proliferation, promote wound healing (Maeda et al., 1980; Liu et al., 1988), and inhibit TNF α-mediated apoptosis (Van Molle et al., 1997; Van Molle 1999). BMPER is a protein primarily expressed in endothelial cells and has been known to regulate mesoderm specification, endothelial cell differentiation, angiogenesis, and development of osteoblasts and chondrocytes via mediating the activity of bone morphogenetic protein (BMP) 4 (Moser et al., 2003; Heinke et al., 2008; Ikeya et al., 2006). FGF21 is one of the 23 members of the FGF family (Fukumoto et al., 2000) and has been reported to stimulate insulin-independent glucose metabolism (Dostalova et al., 2009; Kharitonenkov et al., 2005), stimulate insulin expression and secretion from the pancreatic cells, induce lipolysis in adipocytes (Badman et al., 2007; Inagaki et al., 2007; Hotta et al., 2009), and reduce plasma LDL (Kharitonenkov et al., 2005; Guerre-Millo et al., 2000; Chou et al., 2002). NRG4 is a protein shed from the cell membrane (Hayes et al., 2008) and has been known to induce proliferation of ErbB4 expressing cells, neurite formation (Hayes et al., 2008; Harari et al., 1999), and lineage determination of pancreatic islet cells (Huotari et al., 2002). TFF3 is expressed primarily in mucus-secreting goblet cells of the gastrointestinal tract (Sands and Podolsky 1996) and has been shown to regulate the integrity of mucosae and promote mucosal healing in intestinal injury (Sands and Podolsky 1996; Wong et al., 1999).

The hepatocyte secretory factors may be administered in combinations of two of more factors (e.g., as a single combination or sequentially administered). Exemplary combinations of factors, which can consist of or comprise these combinations, are shown in Table 1 below:

TABLE 1

| | | | | |
|---|---|---|---|---|
| Combination 1 | AGP2 | BMPER | | |
| Combination 2 | AGP2 | FGF21 | | |
| Combination 3 | AGP2 | NRG4 | | |
| Combination 4 | AGP2 | TFF3 | | |
| Combination 5 | BMPER | FGF21 | | |
| Combination 6 | BMPER | NRG4 | | |
| Combination 7 | BMPER | TFF3 | | |
| Combination 8 | FGF21 | NRG4 | | |
| Combination 9 | FGF21 | TFF3 | | |
| Combination 10 | AGP2 | BMPER | FGF21 | |
| Combination 11 | AGP2 | FGF21 | NRG4 | |
| Combination 12 | AGP2 | NRG4 | TFF3 | |
| Combination 13 | BMPER | FGF21 | NRG4 | |
| Combination 14 | BMPER | NRG4 | TFF3 | |
| Combination 15 | FGF21 | NRG4 | TFF3 | |
| Combination 16 | AGP2 | BMPER | FGF21 | NRG4 |
| Combination 17 | AGP2 | FGF21 | NRG4 | TFF3 |
| Combination 18 | AGP2 | NRG4 | TFF3 | BMPER |
| Combination 19 | BMPER | FGF21 | NRG4 | TFF3 |
| Combination 20 | AGP2 | BMPER | FGF21 | NRG4 | TFF3 |

Variants of Hepatocyte Secretory Factors

In certain embodiments, the present invention provides variants of a hepatocyte secretory factor, such as AGP2 (e.g., SED NOs: 11 and 12), BMPER (e.g., SEQ ID NOs: 13 and 14), FGF21 (e.g., SEQ ID NOs: 15, 16, and 27), NRG4 (e.g., SEQ ID NOs: 17-24), and TFF3 (e.g., SEQ ID NOs: 25 and 26). In some embodiments, the present invention provides one or more portions of SEQ ID NOs:11-27. In some embodiments, the present invention provides one or more biologically active portions of the peptide sequences in SEQ ID NOs:11-27 (e.g., a peptide that is useful in treating or preventing ischemic injury). In some embodiments, the present invention provides a mutant version of SEQ ID NOs:11-27. In some embodiments, the present invention provides one or more conserved portions of SEQ ID NOs: 11-27. The present invention also contemplates sequences that are substantially the same as SEQ ID NOs:11-27 or exhibit substantially the same, or similar, activity. For example, one or two amino acids may be changed (or one or two codons changed in the nucleic acid) such that a sequence differing by one or two bases from SEQ ID NOs:11-27 is generated. In some embodiments, multiple amino acids in these sequences are changed (or codons in nucleic acids coding these sequences) while maintaining similar secondary structure, tertiary structure, and/or activity. Changes to the amino acid sequence may be generated by changing the nucleic acid sequence encoding the amino acid sequence. Nucleic acid encoding a variant of a given portion of these sequences may be prepared by methods known in the art. These methods include, but are not limited to, preparation by site-directed (or oligonucleotide-mediated) mutagenesis, PCR mutagenesis, and cassette mutagenesis of an earlier prepared nucleic acid encoding AGP2, BMPER, FGF21, NRG4, and TFF3. Site-directed mutagenesis is a preferred method for preparing substitution variants. This technique is well known in the art (see, e.g., Carter et al. Nucleic Acids Res. 13: 4431-4443 (1985) and Kunkel et. al., Proc. Natl. Acad. Sci. USA 82: 488 (1987), both of which are hereby incorporated by reference).

Briefly, in carrying out site directed mutagenesis of DNA, the starting DNA is, for example, altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA. Polypeptides containing such mutated regions can be screened in assays known in the art to determine if such polypeptides are suitable for use in embodiments of the present invention. For example, one can screen such mutants and variants using the methods described in Example 3, by substituting the candidate variants hepatocyte secretory factor for those described in Example 3 and determining if ischemic injury is reduced or prevented.

PCR mutagenesis is also suitable for making amino acid sequence variants of SEQ ID NOs: 11-27 (see, e.g., Vallette et. al., Nuc. Acids Res. 17: 723-733 (1989), hereby incorporated by reference). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. Polypeptides containing such mutated regions can be screened in assays known in the art to determine if such polypeptides are suitable for use in embodiments of the present invention. For example, one can screen such mutants and variants using the methods described in Example 3, by substituting the candidate variants hepatocyte secretory factor for those described in Example 3 and determining if ischemic injury is reduced or prevented.

Another method for preparing variants, cassette mutagenesis, is based on the technique described by Wells et al., Gene 34: 315-323 (1985), hereby incorporated by reference. The starting material is the plasmid (or other vector) comprising the nucleic acid encoding the hepatocyte secretory factor to be mutated. The codon(s) in the starting DNA to be mutated are identified. There should be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence. Polypeptides containing such mutated regions can be screened in assays known in the art to determine if such polypeptides are suitable for use in embodiments of the present invention. For example, one can screen such mutants and variants using the methods described in Example 3, by substituting the candidate variants hepatocyte secretory factor for those described in Example 3 and determining if ischemic injury is reduced or prevented.

Alternatively, or additionally, the desired amino acid sequence encoding a polypeptide variant can be determined, and a nucleic acid sequence encoding such amino acid sequence variant can be generated synthetically. Conservative modifications in the amino acid sequences of hepatocyte secretory factors, or in the nucleic acids encoding such factors, may also be made (e.g., conservative modification in SEQ ID NO:11-27).

Naturally occurring residues are divided into classes based on common side-chain properties:
  (1) hydrophobic: norleucine, met, ala, val, leu, ile;
  (2) neutral hydrophilic: cys, ser, thr;
  (3) acidic: asp, glu;
  (4) basic: asn, gln, his, lys, arg;
  (5) residues that influence chain orientation: gly, pro; and
  (6) aromatic: trp, tyr, phe.
Conservative substitutions will entail exchanging a member of one of these classes for another member of the same class.

In some embodiments, the present invention provides protein or polypeptide, or nucleic acid sequences corresponding to all or a portion of SEQ ID NOs:11-27 or Accession numbers: P19652; M21540; NP_597725; NM 133468; ABI75345; NM_019113; NP_612640; NM_138573; AAH17859; and BG017859, the sequences of which are herein incorporated by reference. In some embodiments, protein or polypeptide corresponding to all or a portion of SEQ ID NOs:11-27 is administered to a subject. In some embodiments, up to 1% of the amino acids or nucleic acids in the wild-type sequence of SEQ ID NOs:11-27 are mutated (e.g. deletions, insertion, point mutations, etc.). In some embodiments, greater than 1% of the amino acids or nucleic acids in the wild-type sequence of SEQ ID NOs:11-27 (e.g. 5 amino acids . . . 10 amino acids . . . 20 amino acids . . . 50 amino acids . . . 100 amino acids, etc.) are mutated (e.g. deletions, insertion, point mutations, etc.). In some embodiments, the present invention provides proteins and/or polypeptides, or nucleic acids comprising deletion of significant portions of SEQ ID NOs:11-27 (e.g. 10 amino acids . . . 20 amino acids . . . 50 amino acids . . . 100 amino acids . . . 200 amino acids, etc.). In some embodiments, the present invention provides nucleic acids coding proteins and/or polypeptides comprising deletion of significant portions of SEQ ID NOs:11-27 (e.g. 10 amino acids . . . 20 amino acids . . . 50 amino acids . . . 100 amino acids . . . 200 amino acids, etc.). In some embodiments, the present invention provides proteins or polypeptides or nucleic acids comprising SEQ ID NOs:11-27 with an N-terminal deletion of up to 100 amino acids. In some embodiments, the present invention provides proteins or polypeptides comprising SEQ ID NOs:11-27 with a C-terminal deletion of up to 100 amino acids.

In some embodiments, the present invention employs variants of FGF21, such as those described in Pat. Pub. 20090305986 and U.S. Pat. No. 7,655,627 (both of which are herein incorporated by reference), which describe variants of the human FGF21 sequences shown in SEQ ID NO:27 (FIG. 26).

In certain embodiments, the present invention employs an isolated polypeptide comprising an amino acid sequence of SEQ ID NO:27, further comprising the substitution of any amino acid for: the alanine residue at position 45, the leucine residue at position 86, the leucine residue at position 98, the alanine residue at position 111, the alanine residue at position 129, the glycine residue at position 170, the proline residue at position 171 or the serine residue at position 172, and combinations thereof.

In further embodiments, the present invention employs an isolated polypeptide comprising an amino acid sequence of SEQ ID NO: 27 having: (a) at least one amino acid substitution that is: (i) a glutamine, isoleucine, or lysine residue at position 19; (ii) a histidine, leucine, or phenylalanine residue at position 20; (iii) an isoleucine, phenylalanine, tyrosine, or valine residue at position 21; (iv) an isoleucine, phenylalanine, or valine residue at position 22; (v) an alanine or arginine residue at position 150; (vi) an alanine or valine residue at position 151; (vii) a histidine, leucine, phenylalanine, or valine residue at position 152; (viii) an alanine, asparagine, aspartic acid, cysteine, glutamic acid, glutamine, proline, or serine residue at position 170; (ix) an alanine, arginine, asparagine, aspartic acid, cysteine, glutamic acid, glutamine, glycine, histidine, lysine, serine, threonine, tryptophan, or tyrosine residue at position 171; (x) a leucine or threonine residue at position 172; or (xi) an arginine or glutamic acid residue at position 173; and (b) at least one amino acid substitution that is: (i) an arginine, glutamic acid, or lysine residue at position 26; (ii) an arginine, glutamic acid, glutamine, lysine, or threonine residue at position 45; (iii) a threonine residue at position 52; (iv) a cysteine, glutamic acid, glycine, or serine residue at position 58; (v) an alanine, arginine, glutamic acid, or lysine residue at position 60; (vi) an alanine, arginine, cysteine, or histidine residue at position 78; (vii) a cysteine or threonine residue at position 86; (viii) an alanine, arginine, glutamic acid, lysine, or serine residue at position 88; (ix) an arginine, cysteine, glutamic acid, glutamine, lysine, or threonine residue at position 98; (x) an arginine, aspartic acid, cysteine, or glutamic acid residue at position 99; (xi) a lysine or threonine residue at position 111; (xii) an arginine, asparagine, aspartic acid, glutamic acid, glutamine, histidine, or lysine residue at position 129; or (xiii) an arginine, glutamic acid, histidine, lysine, or tyrosine residue at position 134; and combinations thereof.

In certain embodiments, the present invention employs an isolated polypeptide comprising an amino acid sequence of SEQ ID NO: 27 having at least one amino acid substitution that is: (a) a glutamine, lysine or isoleucine residue at position 19; (b) a histidine, leucine, or phenylalanine residue at position 20; (c) an isoleucine, phenylalanine, tyrosine, or valine residue at position 21; (d) an isoleucine, phenylalanine, or valine residue at position 22; (e) an alanine or arginine residue at position 150; (f) an alanine or valine residue at position 151; (g) a histidine, leucine, phenylalanine, or valine residue at position 152; (h) an alanine, aspartic acid, cysteine, or proline residue at position 170; (i) an alanine, arginine, asparagine, aspartic acid, cysteine, glutamic acid, glutamine, glycine, histidine, lysine, serine, threonine, tryptophan, or tyrosine residue at position 171; (j) a leucine residue at position 172; or (k) an arginine or glutamic acid residue at position 173; and combinations thereof.

In other embodiments, the present invention employs an isolated polypeptide comprising an amino acid sequence of SEQ ID NO: 27 having at least one amino acid substitution that is: (a) an arginine, glutamic acid, or lysine residue at position 26; (b) an arginine, glutamic acid, glutamine, lysine, or threonine residue at position 45; (c) a threonine residue at position 52; (d) a glutamic acid, glycine, or serine residue at position 58; (e) an alanine, arginine, glutamic acid, or lysine residue at position 60; (f) an alanine, arginine, or histidine residue at position 78; (g) an alanine residue at position 88; (h) an arginine, glutamic acid, glutamine, lysine, or threonine residue at position 98; (i) an arginine, aspartic acid, cysteine, or glutamic acid residue at position 99; (j) a lysine or threonine residue at position 111; (k) an arginine, asparagine, aspartic acid, glutamic acid, glutamine, histidine, or lysine residue at position 129; or (l) an arginine, glutamic acid, histidine, lysine, or tyrosine residue at position 134; and combinations thereof.

In particular embodiments, the present employs variants of human FGF-21, or a biologically active peptide thereof, comprising the substitution of any amino acid except Asn or Gln for Asn 121, wherein the numbering of the amino acids is based on SEQ ID NO:27.

In further embodiments, the present invention employs variants of human FGF-21, or a biologically active peptide thereof, comprising the substitution of any amino acid except Asn or Gln for Asn 121, in combination with the substitution of a cysteine for two or more of the following: arginine 19, tyrosine 20, leucine 21, tyrosine 22, threonine 23, aspartate 24, aspartate 25, alanine 26, glutamine 27, glutamine 28, alanine 31, leucine 33, isoleucine 35, leucine 37, valine 41, glycine 42, glycine 43, glutamate 50, glutamine 54, leucine 58, valine 62, leucine 66, glycine 67, lysine 69, arginine 72, phenylalanine 73, glutamine 76, arginine 77, aspartate 79, glycine 80, alanine 81, leucine 82, glycine 84, serine 85, proline 90, alanine 92, serine 94, phenylalanine 95, leucine 100, aspartate 102, tyrosine 104, tyrosine 107, serine 109, glutamate 110, proline 115, histidine 117, leucine 118, proline 119, asparagine 121, lysine 122, serine 123, proline 124, histidine 125, arginine 126, aspartate 127, alanine 129, proline 130, glycine 132, alanine 134, arginine 135, leucine 137, proline 138, or leucine 139, wherein the numbering of amino acids is based on SEQ ID NO:27.

In additional embodiments, the present invention employs variants of human FGF-21, or a biologically active peptide thereof, comprising the substitution of any amino acid except Asn or Gln for Asn 121 in combination with the substitution of a charged and/or polar but uncharged amino acid for one or more of the amino acids at positions: glycine 42, glutamine 54, arginine 77, alanine 81, leucine 86, phenylalanine 88, lysine 122, histidine 125, arginine 126, proline 130, arginine 131, leucine 139, alanine 145, leucine 146, isoleucine 152; alanine 154; glutamine 156, glycine 161, serine 163, glycine 170, or serine 172, wherein the numbering of amino acids is based on SEQ ID NO:27.

In further embodiments, the present invention employs variants of human FGF-21, or a biologically active peptide thereof, comprising the substitution of any amino acid except Asn or Gln for Asn 121 in combination with the substitution of any amino acid except Ser or Thr for Ser 167, wherein the numbering of amino acids is based on SEQ ID NO:27.

In additional embodiments, the present invention employs variants of human FGF-21, or a biologically active peptide thereof, selected from the group consisting of Leu118Cys-Ala134Cys-Asn121Ala-Ser167Ala, Leu118Cys-Ala134Cys-Asn121Val-Ser167Ala, Leu118Cys-Ala134Cys-Asn121Ser-Ser167Ala, Leu118Cys-Ala134Cys-Asn121Asp-Ser167Ala, and Leu118Cys-Ala134Cys-Asn121Glu-Ser167Ala wherein the numbering of amino acids is based on SEQ ID NO:27. Additional variants of human FGF21 are described in WO2010065439, which is herein incorporated by reference.

In particular embodiments, the present invention employs variants of BMPER using any or all of amino acid changes described above. In certain embodiments, the N-terminal 10 ... 20 ... 30 ... or 50 amino acids (e.g., 10, 20, 30, 40, or 50 amino acids) are deleted from the human BMPER sequence shown in SEQ ID NO:13. In further embodiments, the C-terminal 10 ... 20 ... 30 ... or 50 amino acids (e.g., 10, 20, 30, 40, or 50 amino acids) are deleted from the human BMPER sequence shown in SEQ ID NO:13. In further embodiments, the human BMPER sequence shown in SEQ ID NO:13 has both N and C terminal deletions.

EXAMPLES

The following Examples are presented in order to provide certain exemplary embodiments of the present invention and are not intended to limit the scope thereof.

Example 1

Cardioprotective Role of Hepatic Cells in Myocardial Ischemia

Experimental Procedures
Transgenic Mouse Models

The Cre/loxP transgenic mouse models have been widely used for identifying and tracking specific cell types[63,64]. In this Example, Cre-EYFP and Cre-EYFP-IL6$^{-/-}$ mouse models were used for identifying hepatic cells in the circulatory system and ischemic lesion of myocardium. The Cre-EYFP model was established by crossing an Alb-Cre$^{+/+}$ mouse strain [B6.Cg-Tg(Alb-cre)21Mgn/J, C57BL/6J background, Jackson Laboratory] with a conditional EYFP$^{+/+}$ mouse strain [B6.129X1-Gt(ROSA)26Sor$^{tm1(EYFP)Cos}$/J, C57BL/6J background, Jackson Laboratory] expressing the EYFP gene controlled by a loxP-flanked stop sequence, which blocks EYFP expression. When the albumin gene promoter-driven Cre recombinase gene is expressed in the liver, the stop sequence of the EYFP gene between the loxP sites is deleted by the Cre recombinase, resulting in liver-specific EYFP expression. The expression of the Cre recombinase and EYFP was confirmed by RT-PCR.

Figure 3:
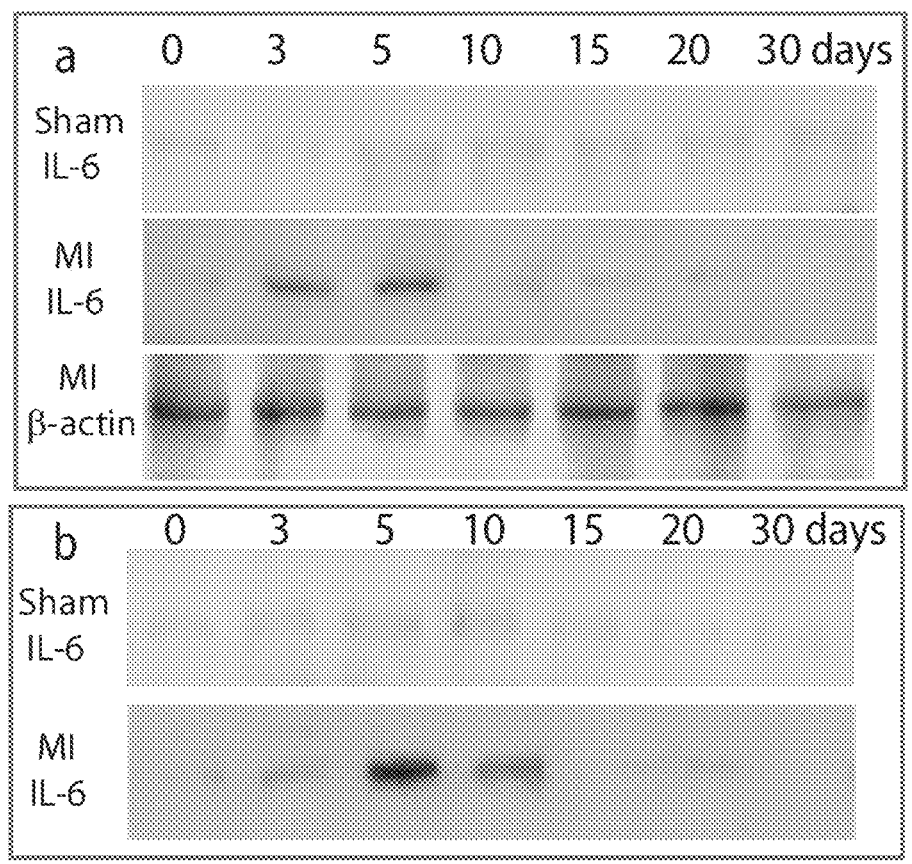
FIG. 3. Role of IL-6 in mediating hepatic cell mobilization in experimental myocardial ischemia. (a) Relative expression of IL-6 in sham control and ischemic myocardium at day 0, 3, 5, 10, 15, 20, and 30. MI: myocardial ischemia. (b) Relative serum levels of IL-6 in mice with sham operation and myocardial ischemia at day 0, 3, 5, 10, 15, 20, and 30. Specimens at zero time were prepared from mice without surgical operation. (c) Cytometry analysis of blood-borne EYFP+ cells derived from sham-operated Cre-EYFP mice with and without IL-6 administration. A standard level of fluorescence intensity (the left side of the rectangle) was established from the EYFP+hepatic cells of Cre-EYFP mice as described in the method section and used for assessing the population of blood-borne EYFP+ cells. The fraction shown in each panel represents the mean and standard deviation of the EYFP+ cell population from 6 tests. The inserts in selected panels show the portion of EYFP+ cells with a magnified scale. MI: myocardial ischemia. Note that the standard level and notations also apply to panel E of this figure. (d) RT-PCR analysis of the relative level of IL-6, Cre recombinase, and EYFP mRNA in the liver of selected mouse strains. C-E-IL-6-/-: Cre-EYFP-IL-6-/- mice. Cond E: Conditional EYFP mice (without crossing with the Alb-Cre strain). (e) Cytometry analysis of EYFP+ cells derived from the liver, circulating blood, and ischemic myocardium of Cre-EYFP-IL6-/- mice with various modulations at day 5. LT: Leukocyte transplantation. HT: Hepatic cell transplantation. (f) Fluorescence micrograph showing the lack of EYFP+ cells in the ischemic myocardium of a Cre-EYFP-IL6-/- mouse at day 5. (g) Fluorescence micrograph showing EYFP+ cells recruited to the ischemic myocardium of a Cre-EYFP-IL6-/- mouse with IL-6 administration for 5 days. For panel f and g, the scale bars are 10 um.
Figure 3:
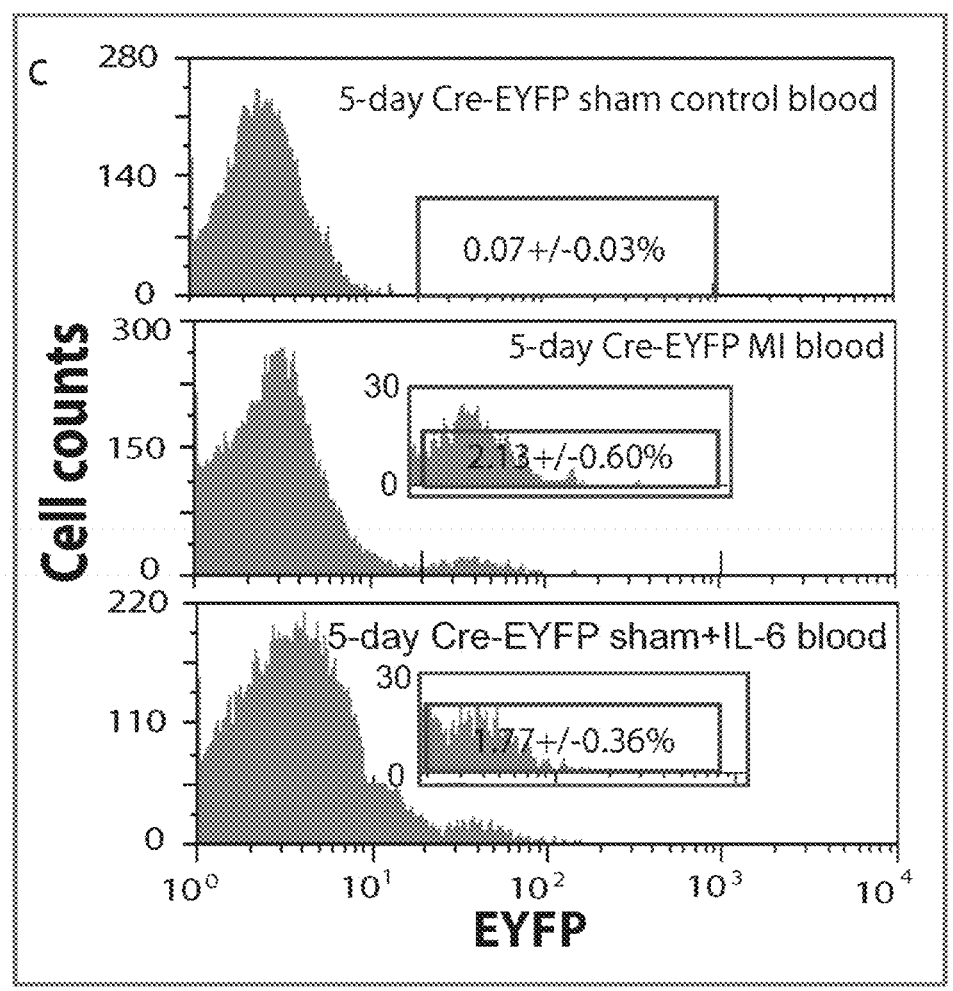
Figure 3:
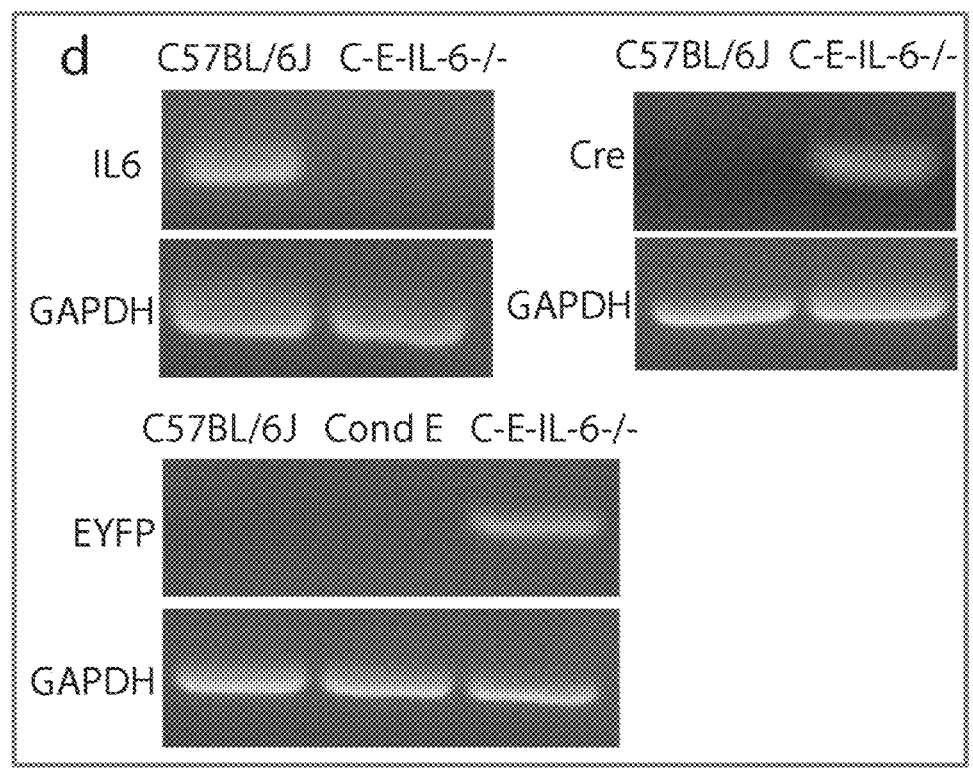
Figure 3:
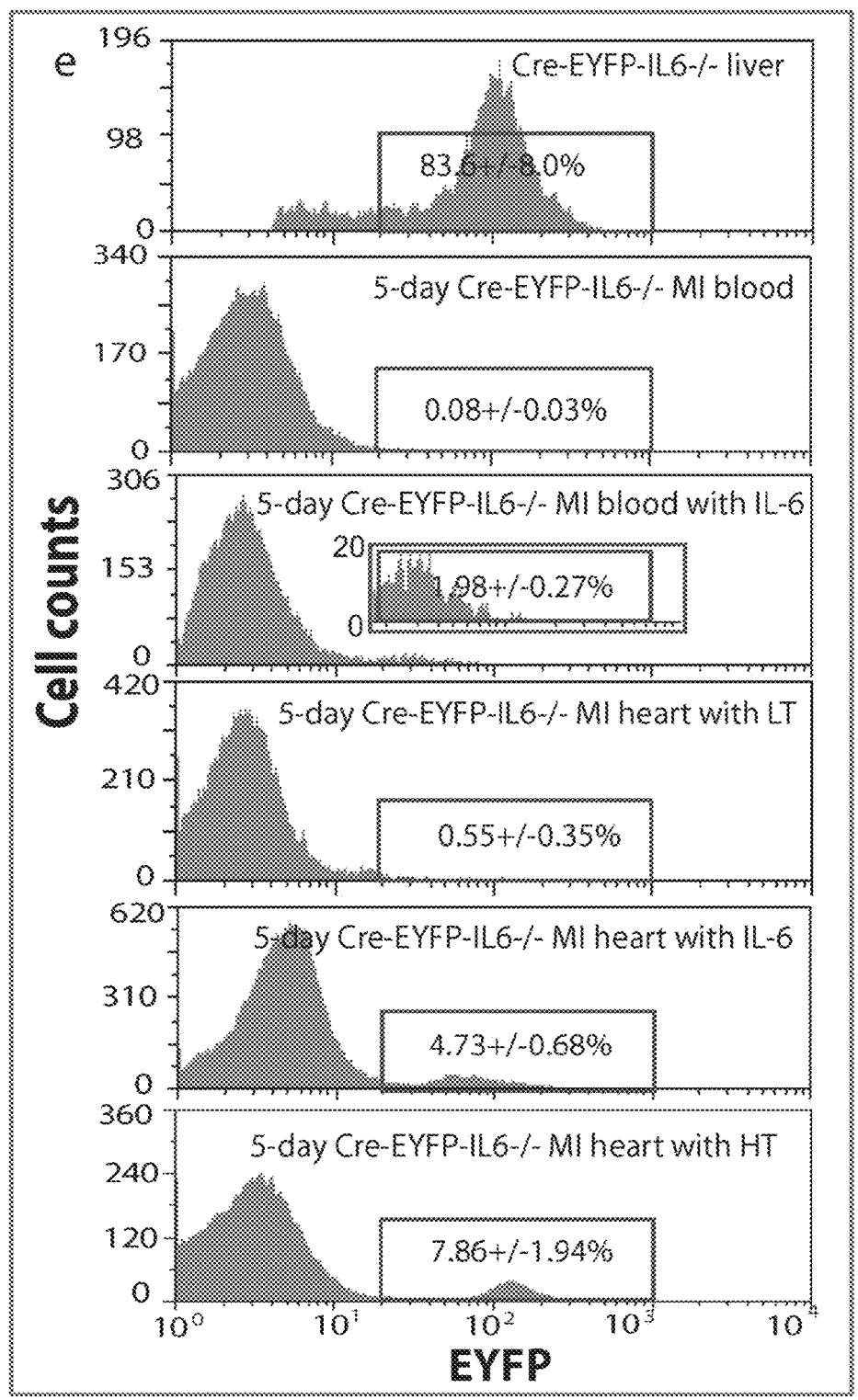
Figure 3:
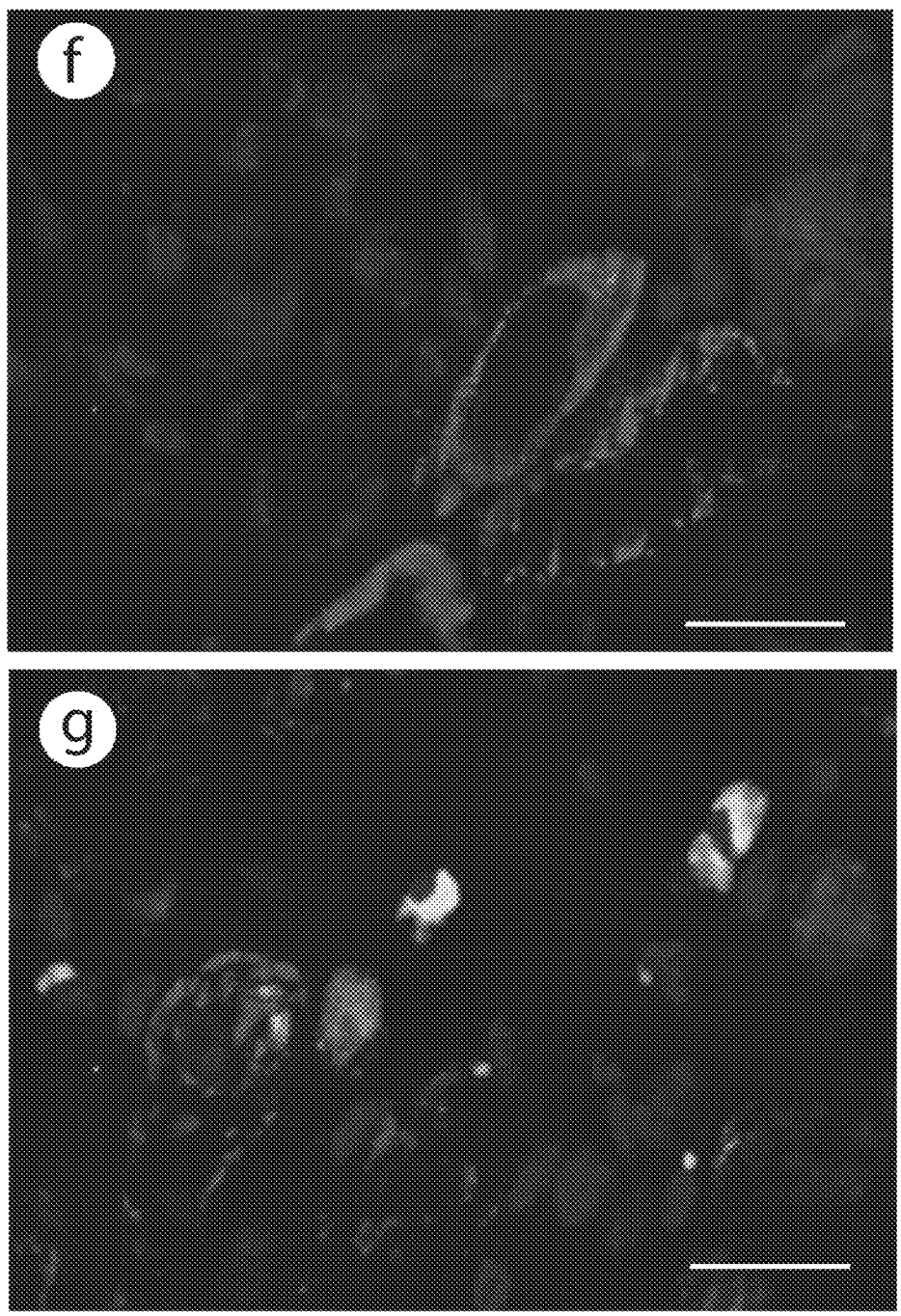

The Cre-EYFP-IL-6$^{-/-}$ model was established and used for identifying EYFP-positive hepatic cells in IL-6$^{-/-}$ mice. An IL-6$^{-/-}$ mouse strain (B6.129S2-116$^{tm1Kopf}$/J, C57BL/6J background, Jackson Laboratory) was crossed with either the Alb-Cre$^{+/-}$ or the EYFP$^{+/+}$ strain. The resulting Cre$^{+/-}$-IL-6$^{+/-}$ or EYFP$^{+/-}$-IL-6$^{+/-}$ strain was further bred for selecting a Cre-IL-6$^{-/-}$ or EYFP-IL-6$^{-/-}$ strain (note that the Cre or EYFP transgene was either homozygous or heterozygous). The Cre-IL-6$^{-/-}$ strain was crossed with the EYFP-IL-6$^{-/-}$ strain for selecting a Cre-EYFP-IL-6$^{-/-}$ strain (note that the Cre or EYFP gene was heterozygous). The expression of the Cre and EYFP transgenes and the deficiency of the IL-6 gene were confirmed by RT-PCR (FIG. 3d).

Coronary Arterial Ligation and Reperfusion

Myocardial ischemia was induced in the mouse by ligating the left anterior descending coronary artery. Mice were anesthetized by intraperitoneal injection of sodium pentobarbital (60 mg/kg) and ventilated via the trachea by using a rodent respirator. Intercostal thoracotomy was carried out and the left anterior descending coronary artery was ligated above the first major bifurcation for 30 min[65] followed by reperfusion. Sham controls were established by using identical procedures with the exception that the coronary artery was not ligated. Observation was conducted at day 3, 5, 10, 15, 20, and 30 following coronary ligation. All experimental procedures were approved by the Institutional Animal Care and Use Committee.

Partial Hepatectomy

Partial hepatectomy was introduced to Cre-EYFP mice with myocardial ischemia. Immediately following coronary arterial ligation and reperfusion, the upper abdominal cavity was opened, and the median and left lateral lobes of the liver were ligated and removed at the common pedicle, resulting in a ~60% removal of the liver mass. The abdominal cavity was closed and the mouse was allowed to recover. Mice with identical surgical procedures except for liver ligation and removal were used as controls. This model has been shown not to induce significant impairment of the liver functions, such as metabolism and detoxification.

RT-PCR

RT-PCR analysis was carried out on hepatic cells and leukocytes derived from the liver. To isolate leukocytes, the liver was perfused via the portal vein with 10% FBS DMEM for 10 min to remove circulating blood cells and treated with collagenase IV as described[68]. Leukocytes were isolated by incubating total liver cells with rat-anti-mouse CD45 antibody (R&D Systems, MAB114), followed by incubation with magnetic beads conjugated with goat-anti-rat antibody and magnetic separation. The isolated leukocytes were verified by immunofluorescence microscopy. The remaining liver cells were considered an independent group for testing. Total RNA was extracted from each cell population by using a total RNA purification kit (Invitrogen). First strand cDNA was synthesized by using the Superscript II Reverse Transcriptase kit (Invitrogen). The synthesized cDNA was amplified by PCR. The primers for the Alb-Cre transgene were 5'-ACCTGAA-GATGTTCGCGATTATCT-3' (SEQ ID NO:1) and 5'-AC-CGTCAGTACGTGAGATATCTT-3' (SEQ ID NO:2) (amplifying a 370-bp fragment)[30]. The primers for the EYFP transgene were 5'-GTCAGTGGAGAGGGTGAAGG-3' (SEQ ID NO:3) and 5'-TACATAACCTTCGGGCATGG-3' (SEQ ID NO:4) (amplifying a 200-bp fragment). The primers for IL-6 were 5'-TTCCATCCAGTTGCCTTCTTGG-3' (SEQ ID NO:5) and 5'-TTCTCATTTCCACGATTTC-CCAG-3' (SEQ ID NO:6) (amplifying a 174-bp fragment). The primers for MMP-2 were 5'-CACACCAGGTGAAG-GATGTG-3' (SEQ ID NO:7) and 5'-GTTGAAGGAAAC-GAGCGAAG-3' (SEQ ID NO:8) (amplifying a 461-bp fragment). The cDNA of GAPDH was used as a control. The primers for GAPDH were 5'-ACCCAGAAGACTGTG-GATGG-3' (SEQ ID NO:9) and 5'-CCCTGTTGCTGTAGC-CGTAT-3' (SEQ ID NO:10) (amplifying a 421-bp product). The PCR products were analyzed by electrophoresis in 2% agarose gels and stained with ethidium bromide for visualization.

Immunoprecipitation and Immunoblotting

The expression of IL-6 and HGF was tested in ischemic and sham control myocardium. The serum level of IL-6 was also tested in mice with and without myocardial ischemia. Rabbit anti-IL-6 antibody (Chemicon, AB1423, IgG) and rabbit anti-HGF α antibody (Santa Cruz, sc-7949, IgG) were used for detecting IL-6 and HGF expression, respectively, by immunoprecipitation and immunoblotting. β-actin was detected and used as a control. For each test, an equal amount of total proteins was loaded to each lane for electrophoresis. The relative expression of each protein was assessed based on the average optical intensity of a protein band measured by using an image analysis system and normalized with reference to the intensity of a selected control protein band.

Gelatin Zymography

Liver specimens were homogenized in lysis buffer for collecting soluble proteins. Collected proteins were resolved in SDS-polyacrylamide gel containing 1 mg/ml gelatin under non-reducing conditions. The gels were incubated in renaturing buffer (2.5% Triton X-100) for 30 min at 20° C. and incubated in developing buffer (50 mM Tris-HCl, pH 7.4, 0.2 M NaCl, 10 mM $CaCl_2$) for 12 h at 37° C. The gels were stained with 0.5% Coomassie Blue 8250.

siRNA Transfection

Hepatic cells were isolated from Cre-EYFP mice with 5-day myocardial ischemia. The liver was treated with collagenase IV as described above to obtain total liver cells. Hepatic cells were isolated from the total liver cells by Percoll density gradient centrifugation. The isolated hepatic cells were examined by fluorescence microscopy and flow cytometry. More than 90% of the isolated cells expressed EYFP (FIG. 3c). These cells were likely composed of hepatocytes and biliary epithelial cells. The isolated hepatic cells were transfected with HGF-specific siRNA (Santa Cruz, sc-37112) or scrambled siRNA (Santa Cruz, sc-37007) as described.

Hepatic Cell Transplantation

Hepatic cells were isolated from Cre-EYFP mice with 5-day myocardial ischemia as described above. Following coronary arterial ligation, isolated hepatic cells (~$10^5$ cells) were slowly injected into the femoral vein of the recipient mouse. Mice with myocardial ischemia injected with allogenic leukocytes (~$10^5$ cells) were used as controls. Cyclosporin was administrated to mice with cell transplantation via drinking water (100 mg/L).

Fluorescence Microscopy

For testing blood-borne cells, a blood sample was collected from the right ventricular chamber of an anesthetized mouse with an 18 G needle and allowed for coagulation. A coagulated blood specimen was fixed in 4% formaldehyde in PBS, cut into cryo-sections of 5 um in thickness, and used for examination by fluorescence microscopy. This method allows for preparing blood specimens with easy antibody access to intracellular molecules and optical properties suitable for microscopic visualization. For examination of the left ventricle and liver, these organs were fixed via carotid arterial perfusion of 4% formaldehyde in PBS, cut into cryo-sections of 5 um in thickness, and used for fluorescence microscopy. Fluorescence images were deconvolved to reduce optical distortion and background noise.

A quantitative method was developed and used for identifying EYFP-positive cells based on the analysis of fluorescence intensity. A standard level of relative fluorescence intensity was established from EYFP-positive liver specimens as $X-t_{0.05,v}\sigma$ or $X-1.962\sigma$, where X is the mean relative fluorescence intensity measured from the EYFP-positive hepatic cells of the liver and normalized with reference to EYFP-negative cells, $t_{0.05,v}$ is the critical value of the t distribution at the confidence level 95% with degree of freedom $v>1000$, and σ is standard deviation[71]. The relative fluorescence intensity of EYFP-positive hepatic cells was measured by using a fluorescence microscope and an image analysis system. Blood-borne cells with relative fluorescence intensity higher than the standard level were identified as EYFP-positive cells. The same method was used for identifying EYFP-positive cells in the ischemic myocardium as well as CK19-positive cells in the circulating blood.

The following antibodies were used for fluorescence microscopy: rabbit anti-cardiac troponin I antibody (Santa Cruz, sc-15368, IgG) for identifying cardiomyocytes; rat anti-CD45 antibody (R&D Systems, MAB114) for identifying leukocytes; goat anti-cytokeratin 19 antibody (Santa Cruz, sc-33111, IgG) for identifying biliary epithelial cells; and rabbit anti-HGF α antibody (Santa Cruz, sc-7949, IgG) for detecting HGF expression. Specimens reacted with isotype-matched antibodies were used as controls. Hoechst 33258 was used for labeling cell nuclei.

Flow Cytometry

The population of selected cell types was measured and analyzed by flow cytometry. For blood-borne cells, a blood sample was collected from an anesthetized mouse and mixed with equal volume of PBS supplemented with 100 U/ml heparin. The red blood cells were remove, and nucleated cells were collected, fixed in 2% formaldehyde, and tested by flow cytometry for detecting EYFP-positive cells (excitation 488 nm, emission 525 nm). A standard level of fluorescence intensity was established from the hepatic cells of the liver in Cre-EYFP mice by using the method described in the section "Fluorescence microscopy" and used for assessing the population of blood-borne EYFP-positive cells. The expression of CK19 in EYFP-positive cells was not analyzed by flow cytometry because cell membrane permeabilization for immuno-labeling CK19 caused loss of EYFP.

To characterize EYFP expression in different organs of the Cre-EYFP mouse model, cells were prepared from the liver, brain, heart, bone marrow, kidney, pancreas, spleen, and small intestine, for testing by flow cytometry. Cells from the brain were prepared by papain treatment and cells from the remaining organs except for the bone marrow were prepared by collagenase treatment. Cells collected from each organ were fixed in 2% formaldehyde and tested by flow cytometry for assessing the population of EYFP-positive cells. A standard level of fluorescence intensity was established from the hepatic cells of the liver in Cre-EYFP mice as described above and used for assessing the population of EYFP-positive cells from other organs. Cytometry gates for fluorescent markers were set based on the fluorescence intensity of simultaneously prepared control cells (for example, C57BL/6 hepatic cells used as a negative control for liver-derived EYFP+ hepatic cells, blood-borne nucleated cells derived from mice without surgery used as a negative control for blood-borne EYFP+ cells, and cells stained with an isotype-matched nonspecific antibody as a negative control for an antibody marker).

TUNEL Assay

The heart of each anesthetized mouse was fixed by arterial perfusion of 4% formaldehyde in PBS. Specimens were collected from the ischemic region of myocardium and cut into cryo-sections of 5 um in thickness. TUNEL assay was carried out to detect myocardial death.

Measurement of Myocardial Infarct Size

Figure 9:
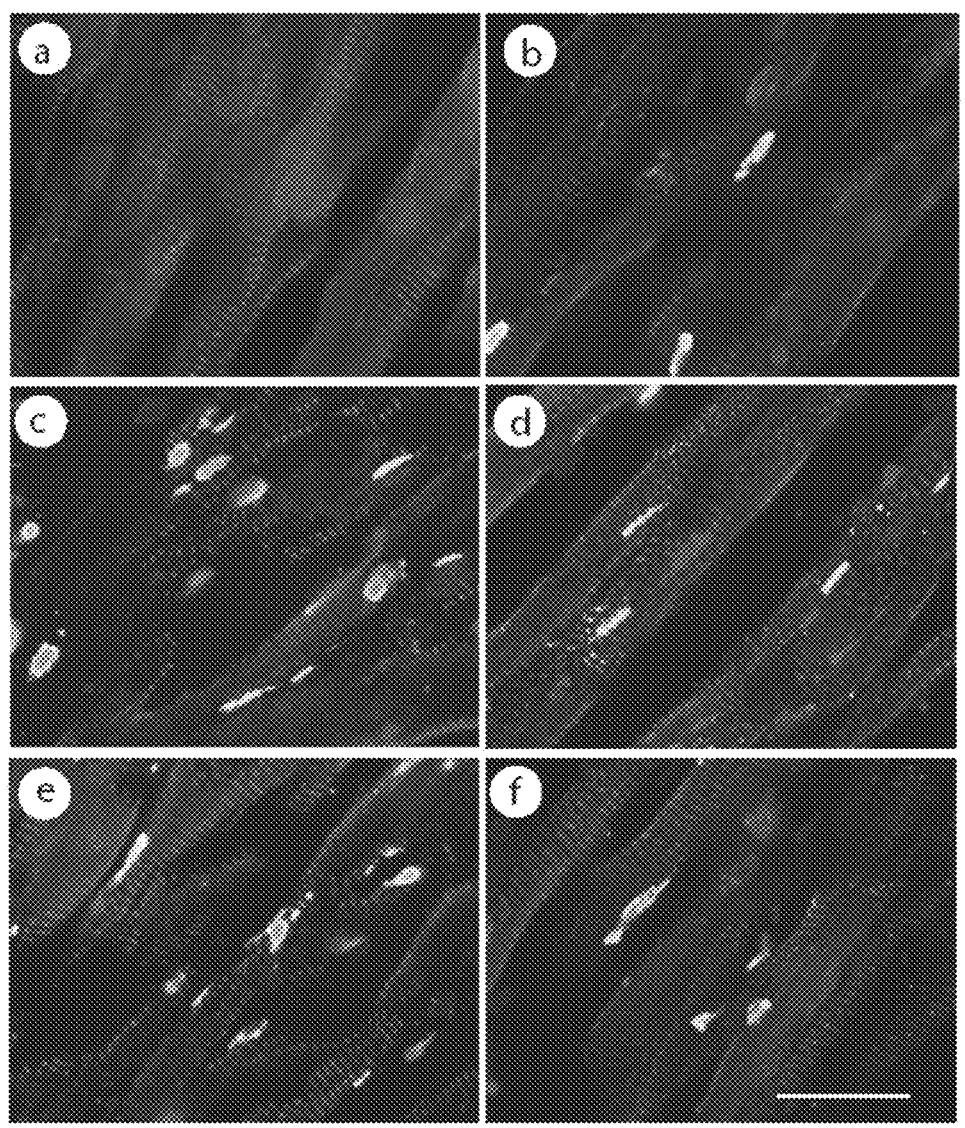
FIG. 9. Influence of hepatic cell transplantation and HGF administration on myocardial death during early myocardial ischemia. (a-f) Fluorescence micrographs showing TUNEL+ myocardial nuclei (green) in the myocardium of C57BL/6J mice with sham operation (panel a) and myocardial ischemia (panel b) at day 1, ischemic IL-6-/- mice with transplantation of leukocytes (panel c) or hepatic cells transfected with scrambled siRNA (panel d) or HGF-specific siRNA (panel e), and an ischemic IL-6-/- mouse with HGF administration (panel f). Scale: 10 um. (g) Measured population size of TUNEL+ myocardial nuclei (as percentage of the total myocardial nuclei) from C57BL/6J and IL-6-/- mice with various modulations. Means and standard deviations are presented (n=6). MI: Myocardial ischemia. HT: Hepatic cell transplantation. LT: Leukocyte transplantation. S: Scrambled. These notations also apply to panel h. (h) Influence of hepatic cell transplantation and HGF administration on the population size of TUNEL+ myocardial nuclei in IL-6-/- mice with 1-day myocardial ischemia. Means and standard deviations are presented (n=6). ab: Anti-HGF antibody. *p<0.05, p<0.01, and *p<0.001.
Figure 9:
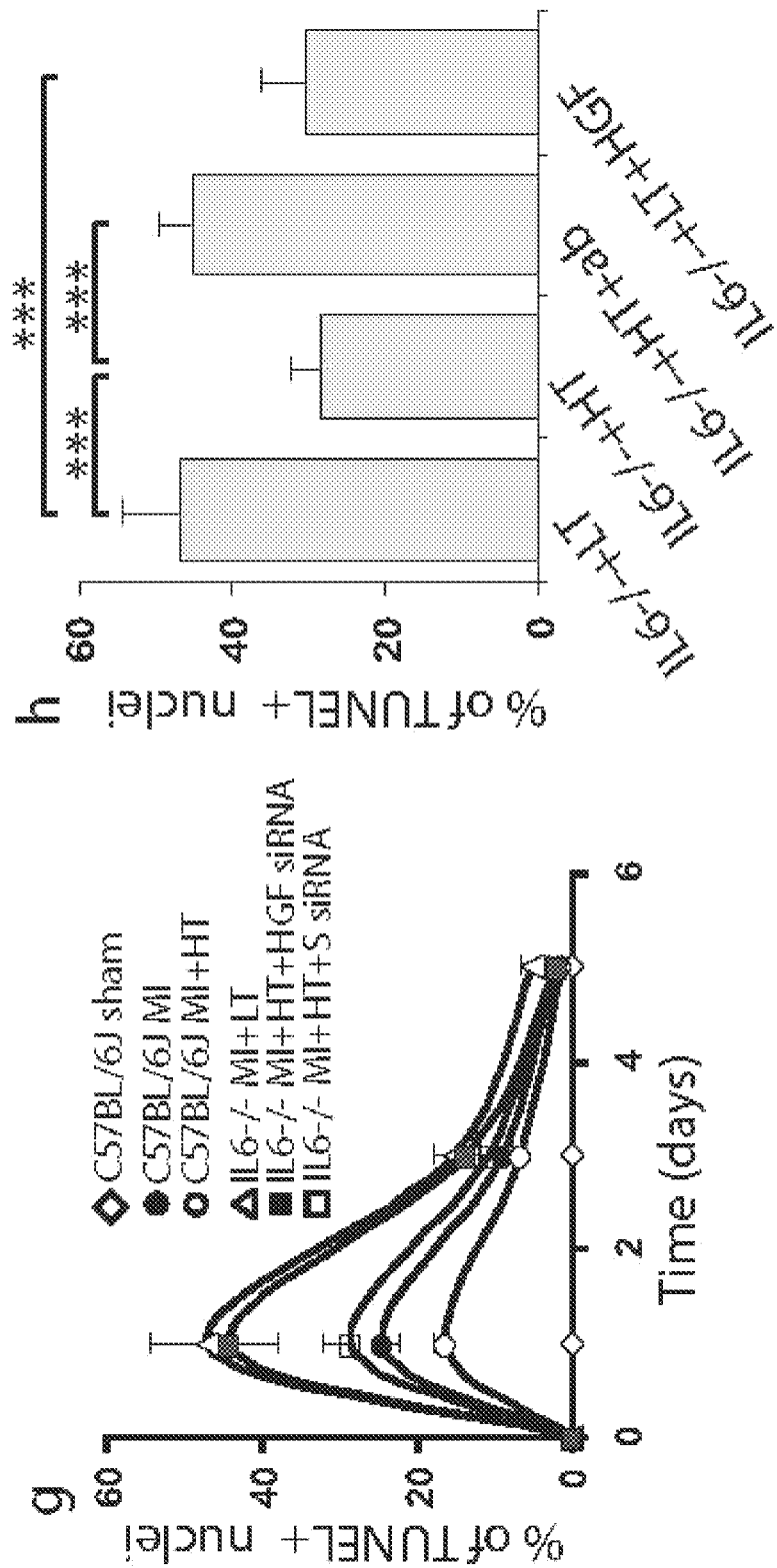

The left ventricle was fixed as described above and cut into transverse serial cryo-sections of 50 um in thickness. All collected specimen sections were stained with AZAN reagents. Specimen sections with myocardial infarcts were collected and used for measuring the areas of myocardial infarcts and the remaining intact myocardium by using an image analysis system (FIG. 9). The total volume of myocardial infarcts and that of the remaining intact myocardium were calculated based on the measured area and section thickness. The volume fraction of myocardial infarcts was calculated with reference to the total volume of the left ventricular segment with myocardial infarcts and used to represent the relative degree of myocardial ischemia.

Hemodynamic Measurements

The fractional shortening of the left ventricle was measured by M-mode echocardiography at the mid-papillary muscle level. The ejection fraction of the left ventricle was measured by B-mode echocardiography with a 15 MHz probe at the maximal ventricular dimensions along the longitudinal axis. Left ventricular dp/dt were measured based on recorded left ventricular blood pressure by using a catheter pressure transducer. All hemodynamic parameters were measured and analyzed in mice with and without myocardial ischemia.

Statistical Analysis

Means and standard deviations were calculated for each measured parameter. The two-tailed Student t-test was used for analyzing differences between two groups. ANOVA was used for multi-group difference analysis. A difference was considered statistically significant at $p<0.05$.

Results

Mobilization of Hepatic Cells in Myocardial Ischemia

Myocardial ischemia was induced in the mouse by ligating the left anterior descending coronary artery for 30 min followed by reperfusion. Lesions of myocardial ischemia, characterized by myocardial disintegration and leukocyte infiltration, were found in the left ventricle following coronary arterial ligation. To demonstrate hepatic cell mobilization in response to myocardial ischemia, a transgenic mouse model was used with liver-specific expression of EYFP, established by crossing a mouse strain expressing the albumin-Cre recombinase gene with a mouse strain expressing the EYFP gene controlled by a loxP-flanked stop sequence, resulting in a model with liver-specific expression of EYFP (referred to as Cre-EYFP model). In this model, EYFP was expressed primarily in hepatocytes and biliary epithelial cells (FIG. 1a), which were about 86.3% of the total liver cells (FIG. 1h). The liver also contains vascular cells and periductular cells, which include CD45+ (about 0.3% of total liver cells), CD11b+ (about 0.06%), and Sca-1+ cells (about 0.04%) (FIG. 10. These cells did not express noticeable EYFP in the Cre-EYFP model (FIG. 1b-d). A RT-PCR analysis showed that, while hepatic cells including hepatocytes and biliary epithelial cells derived from the liver of Cre-EYFP mice expressed EYFP mRNA, CD45+ and Sca-1+ cells did not express noticeable EYFP mRNA (FIG. 1g). c-Kit and CD34 expression were also tested in liver cells. Few c-Kit+ or CD34+ cells were found in the liver of the Cre-EYFP mouse model (FIGS. 1e and 1f). A fluorescence intensity analysis demonstrated that the fluorescence level of hepatocytes and biliary epithelial cells was significantly higher than that of the non-hepatic cell types, including cells from the heart, blood, bone marrow, brain, kidney, spleen, pancreas, and intestine of the Cre-EYFP mouse, and also higher than that of the hepatic cells derived from EYFP-negative C57BL/6J mice (FIG. 1h). These observations suggest that EYFP is specifically expressed in the hepatic cells of the Cre-EYFP model and can be used as a marker for identifying these cells.

Figure 2:
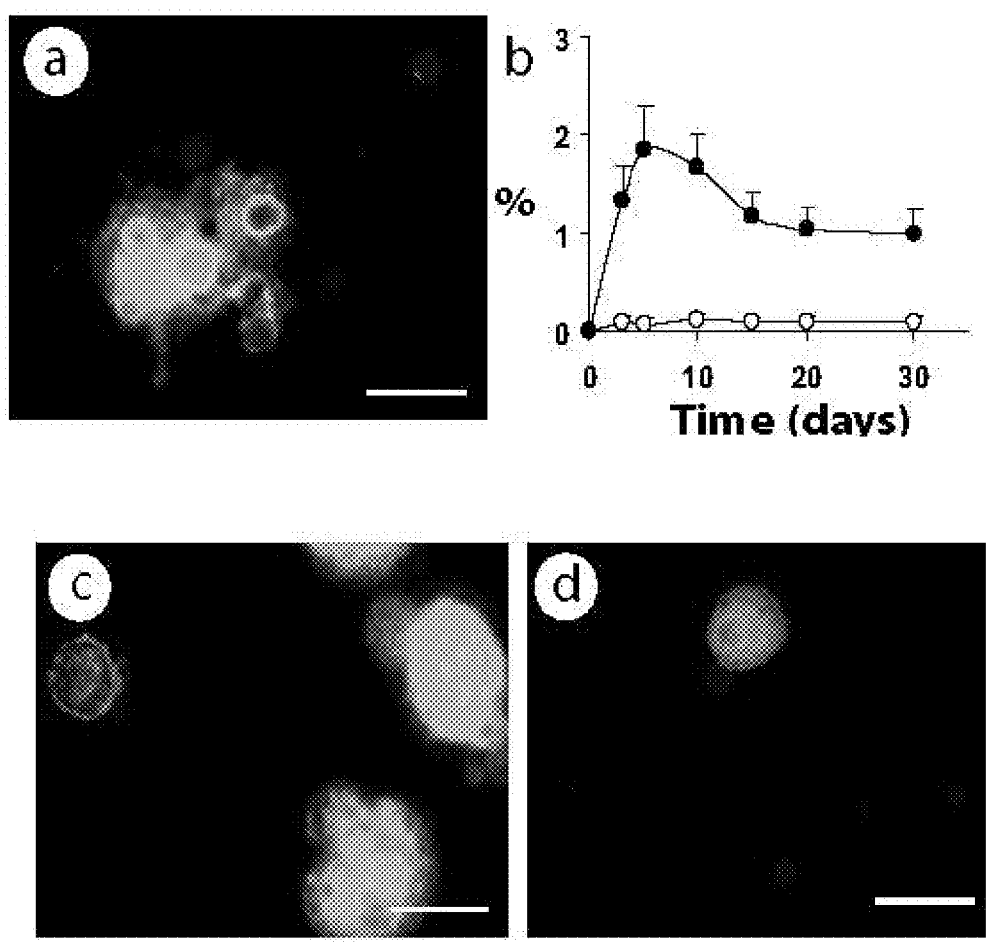
FIG. 2. Mobilization of hepatic cells to the circulatory system of Cre-EYFP mice with myocardial ischemia. (a) Fluorescence micrograph showing blood-borne EYFP+ cells from a Cre-EYFP mouse with 5-day myocardial ischemia. (b) Relative population size of blood-borne EYFP+ cells with reference to the total nucleated blood cells in Cre-EYFP mice with sham-operation (open circles) and myocardial ischemia (solid circles) measured by fluorescence microscopy. Mean and standard deviation are presented ($p<0.001$ for changes in myocardial ischemia by ANOVA, n=6 at each time). (c) Fluorescence micrograph showing EYFP+ hepatic cells isolated from the liver of a sham Cre-EYFP mouse. (d) Expression of CK19 in blood-borne EYFP+ cells from a Cre-EYFP mouse with 5-day myocardial ischemia. For panels a, c, and d, the scale bars are 10 um. (e) One-dimensional cytometry analysis of EYFP+ cells from the liver of Cre-EYFP mice with sham operation, the blood of Cre-EYFP mice with sham operation and myocardial ischemia (MI), and the blood of C57BL/6J mice with myocardial ischemia. A standard level of fluorescence intensity (the left side of the rectangle) was established from the hepatic cells of Cre-EYFP mice as described in the method section and used for assessing the population of blood-borne EYFP-positive cells. The inserts in selected panels show the portion of EYFP-positive cells with a magnified scale. The fraction shown in each panel represents the mean and standard deviation of the EYFP+ cell population from 6 tests. (f) Two-dimensional cytometry analysis demonstrating the lack of CD45, CD11b, c-Kit, or Sca-1 expression in EYFP+ cells derived from the circulating blood of Cre-EYFP mice with sham operation and myocardial ischemia.
Figure 2:
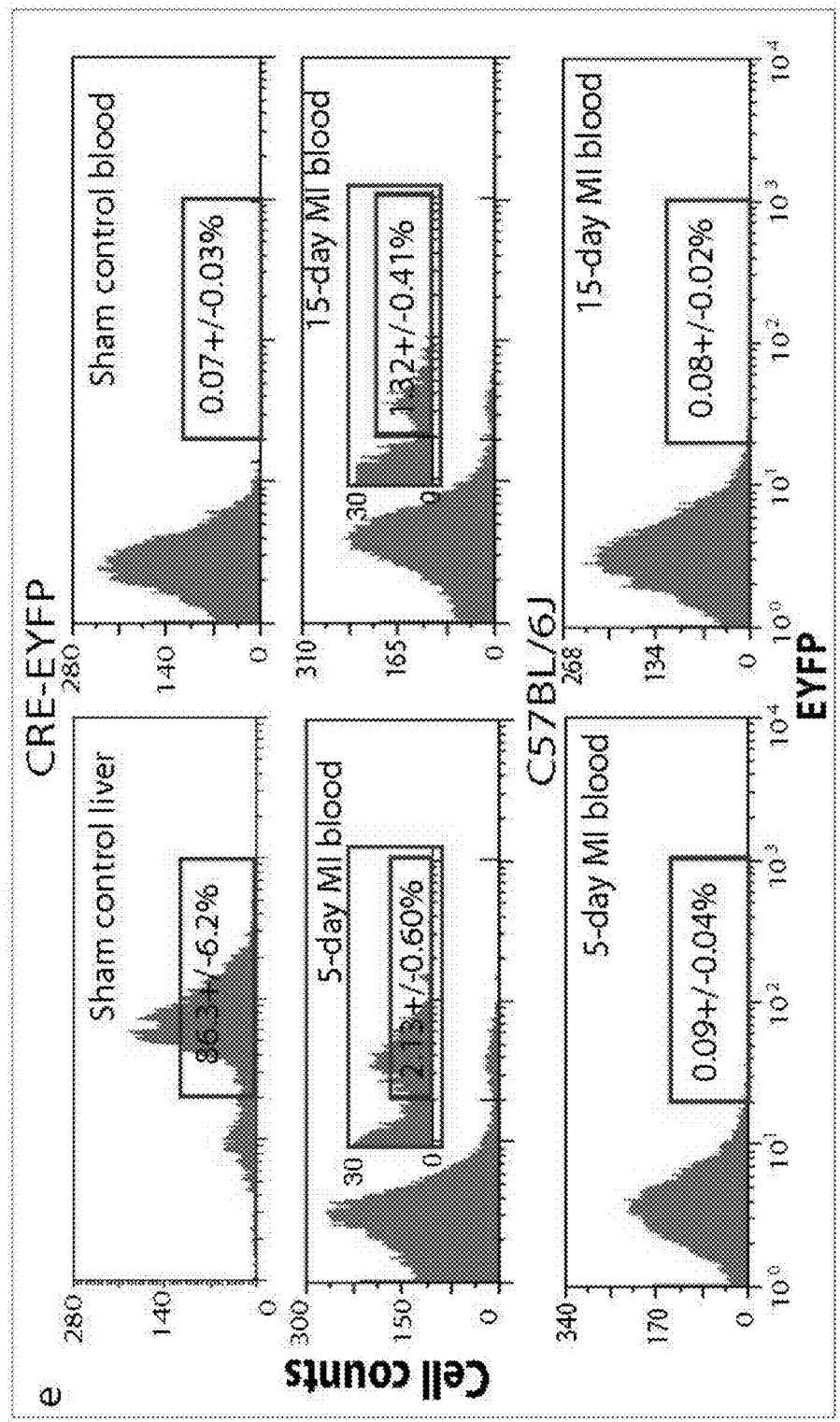
Figure 2:
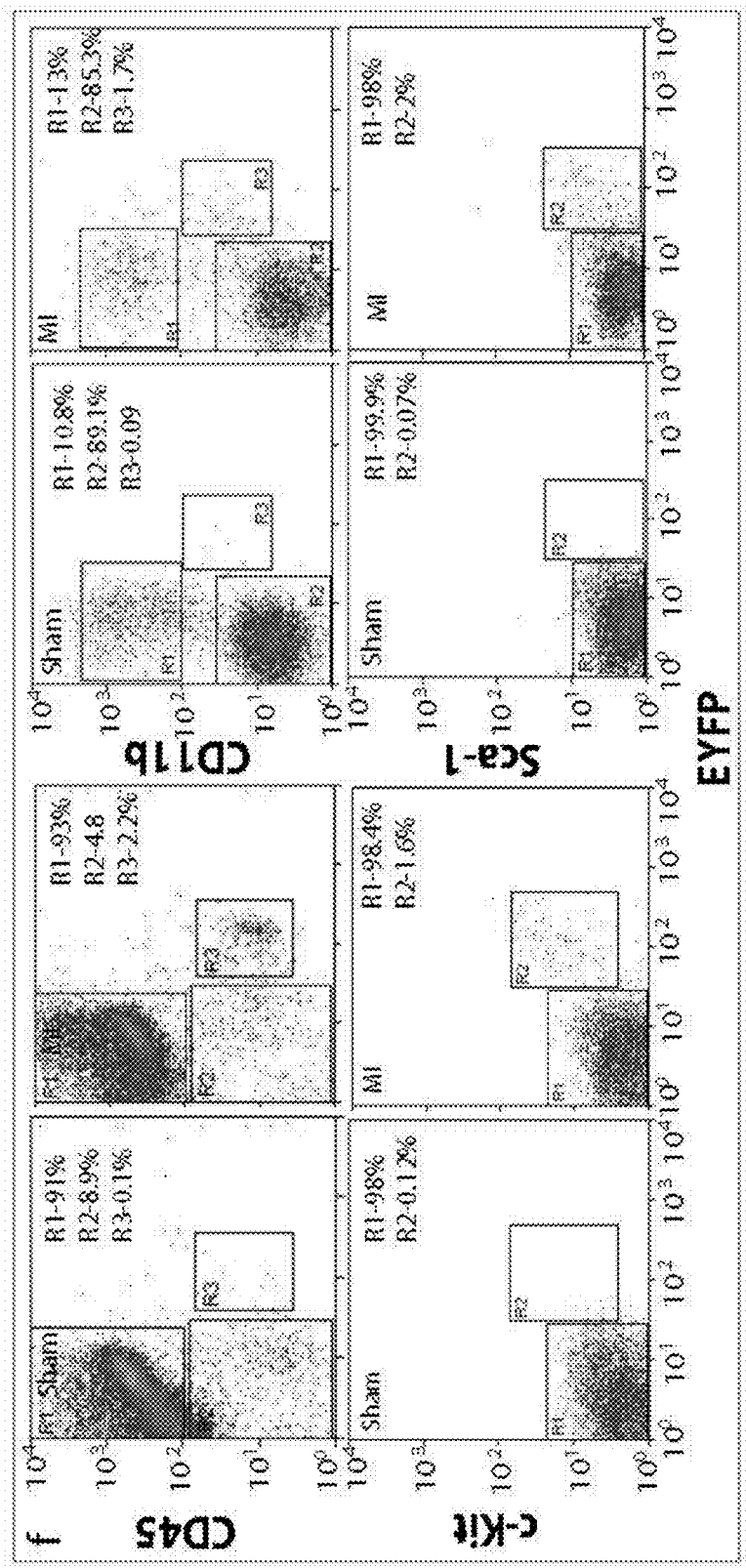

To test hepatic cell mobilization in myocardial ischemia, the population of blood-borne EYFP-positive cells was measured in Cre-EYFP mice by fluorescence microscopy. EYFP-positive cells were found in the circulatory system as early as at day 3 of myocardial ischemia, but not in sham controls (FIGS. 2a and 2b), reached a peak population at day 5, and reduced in population size afterwards (FIG. 2b). These measurements were confirmed by flow cytometry at selected time points (FIG. 2e). The population of the blood-borne EYFP-positive cells in Cre-EYFP mice with myocardial ischemia was significantly larger than that in sham control Cre-EYFP mice at all observation times (FIGS. 2b and 2e). To demonstrate whether bone marrow-derived cells express EYFP, EYFP expression was tested in blood-borne cells by flow cytometry. As shown in FIG. 2f, few CD45+, CD11b+, c-Kit+, or Sca-1+ blood-borne cells expressed EYFP in Cre-EYFP mice with sham-operation and myocardial ischemia. These observations suggest that hepatic cells can be mobilized to the circulatory system in response to experimental myocardial ischemia.

Sources of Mobilized Hepatic Cells in Myocardial Ischemia

In the Cre-EYFP model, EYFP is expressed primarily in two hepatic cell types: hepatocytes and biliary epithelial cells (FIG. 1a). The protein marker cytokeratin (CK) 19 was used, which is expressed primarily in biliary epithelial cells but not in other liver cell types (FIGS. 1a and 2c), together with EYFP expression to identify blood-borne biliary epithelial cells (FIG. 2d). CK19 was found in about 29.0+/−4.8%, 26.5+/−3.4%, and 27.5+/−3.8% of blood-borne EYFP-positive cells at day 5, 15, and 30 (n=6) following the induction of myocardial ischemia, respectively, but not in EYFP-negative blood cells in Cre-EYFP mice with myocardial ischemia. These observations suggest that hepatic cells can be mobilized from the hepatocyte and biliary epithelial cell compartments in experimental myocardial ischemia.

Role of IL-6 in Mediating Hepatic Cell Mobilization

The mobilization of hepatic cells was induced in response to myocardial ischemia. IL-6 was upregulated in the ischemic lesion of myocardium with a peak expression level at day 5 (relative IL-6 expression with reference to the control level without surgical operation: 1.55+/−0.36, 2.44+/−0.50, 1.71+/−0.43, 1.30+/−0.39, 1.24+/−0.40, and 1.19+/−0.34 at day 3, 5, 10, 15, 20, and 30, respectively, n=6, ANOVA $p<0.001$, FIG. 3a). The serum level of IL-6 was also increased along with cardiac expression of IL-6 (relative IL-6 level with reference to the control level without surgical operation: 1.47+/−0.29, 1.96+/−0.26, 1.21+/−0.23, 1.01/−0.12, 1.02+/−0.16, and 1.01+/−0.08 at day 3, 5, 10, 15, 20, and 30, respectively, n=6, ANOVA $p<0.001$, FIG. 3b). In contrast, the level of IL-6 in either the left ventricular myocardium or the serum of sham-operated mice was not significantly altered with reference to the control level without surgical operation during the course of observation (FIGS. 3a and 3b).

To test the possibility that IL-6 mediates hepatic cell mobilization, recombinant mouse IL-6 (Chemicon) was delivered 50 ng/gm×2 per day to sham-operated Cre-EYFP mice via venous injection for 5 days. This modulation induced a significant increase in the population of blood-borne EYFP-positive cells compared to sham-operated mice with placebo administration (FIG. 3c). To confirm the role of IL-6 in mediating hepatic cell mobilization, myocardial ischemia was induced in a Cre-EYFP-IL-6$^{-/-}$ mouse model with IL-6 deficiency and liver-specific expression of EYFP (FIG. 3d). The population of blood-borne EYFP-positive cells in these mice (FIG. 3e) was significantly lower than that in Cre-EYFP mice with myocardial ischemia (FIG. 3c). Venous injection of IL-6 (50 ng/gm×2 per day) to Cre-EYFP-IL-6$^{-/-}$ mice with myocardial ischemia for 5 days significantly enhanced the mobilization of EYFP-positive hepatic cells to the circulatory system compared to control Cre-EYFP-IL-6$^{-/-}$ mice with placebo administration (FIG. 3e). These observations support the role of IL-6 in stimulating the mobilization of hepatic cells.

Leukocyte Retention in Liver Parenchyma in Myocardial Ischemia

Figure 4:
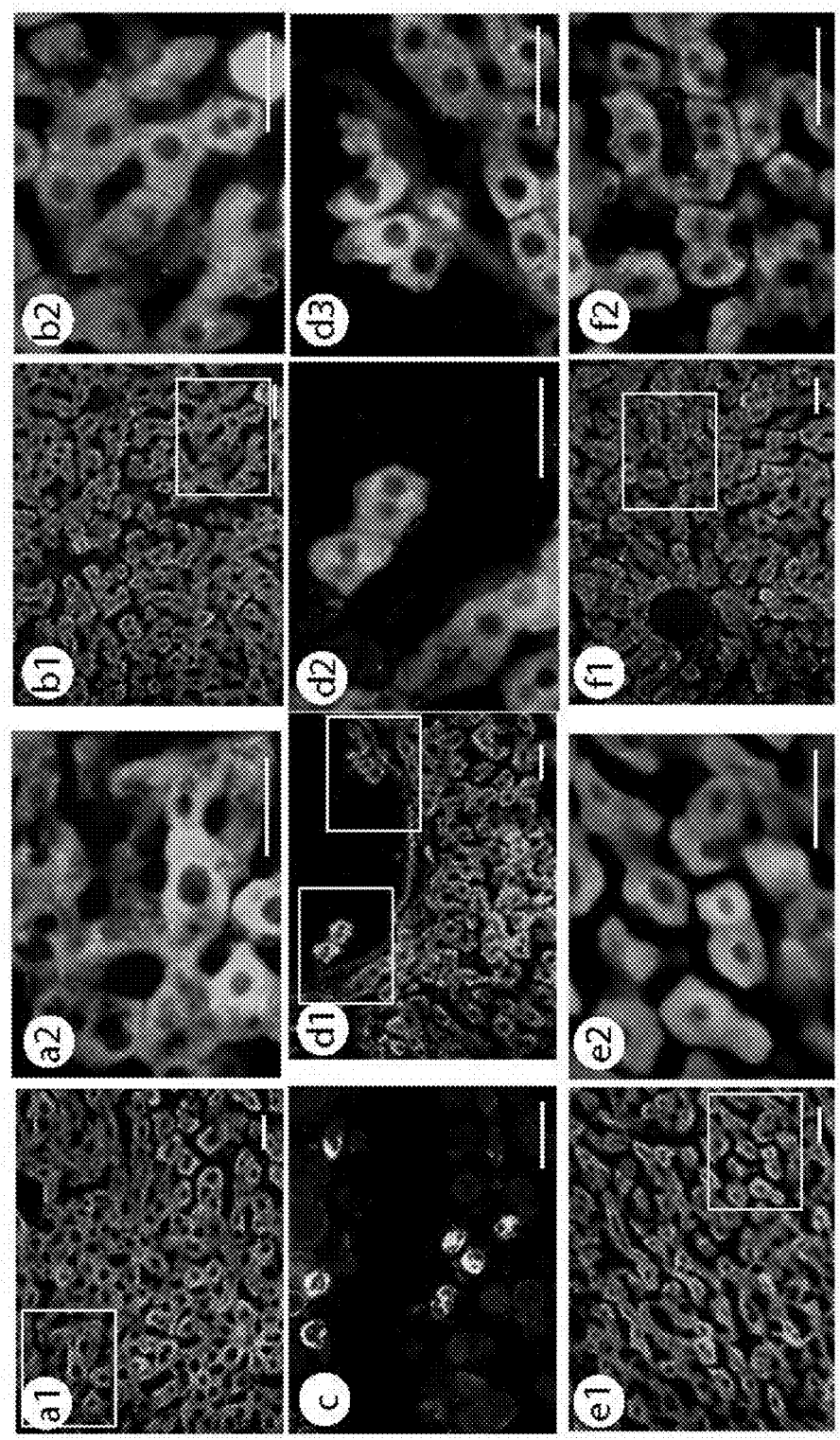
FIG. 4. Leukocyte retention in the liver parenchyma in myocardial ischemia. (a) Fluorescence micrographs showing the lack of CD45+ cells in the liver parenchyma of a Cre-EYFP mouse with sham operation at day 5. Panel a2 is a magnified image of the area (white rectangle) selected from a1. (b) Fluorescence micrographs showing CD45+ cells retained in the liver parenchyma of a Cre-EYFP mouse with 5-day myocardial ischemia. Panel b2 is a magnified image of the area (white rectangle) selected from b1. (c) Fluorescence micrograph showing CD45+ cells with co-expression of MMP-2 in the liver of a C57BL/6J mouse with 5-day myocardial ischemia. (d) Fluorescence micrographs showing association of CD45+ cells with mobilized EYFP+ hepatic cells within a central vein of the liver of a Cre-EYFP mouse with 5-day myocardial ischemia. Panel d2 and d3 are magnified images of the left and right white rectangles, respectively, from d1. (e) Fluorescence micrographs showing the lack of CD45+ cells in the liver parenchyma of a Cre-EYFP-IL-6-/- mouse with 5-day myocardial ischemia. Panel e2 is a magnified image of the area (white rectangle) selected from e1. (f) Fluorescence micrographs showing CD45+ cells retained in the liver parenchyma of a Cre-EYFP-IL-6-/- mouse with 5-day myocardial ischemia with IL-6 administration. Panel f2 is a magnified image of the area (white rectangle) selected from f1. Gray: EYFP. For panel a-f, the scale bars are 10 um. (g) Measured density of CD45+ cells retained in the liver parenchyma of mice with sham-operation (open circles) and myocardial ischemia (solid circles) from day 0 to 30 by fluorescence microscopy. Mean and SD are presented ($p<0.001$ for changes in myocardial ischemia by ANOVA, n=6 at each time). Specimens at time zero were prepared from mice without surgical operation. (h) Influence of IL-6 on CD45+ cell retention in the liver parenchyma of C57BL/6J and IL-6-/- mice with sham-operation and myocardial ischemia. In panel g and h, % of retained CD45+ cells was calculated with reference to the total liver cells. (i) Flow cytometry analysis of liver cells derived from Cre-EYFP mice with sham operation and myocardial ischemia at day 5, showing CD45+ cell retention in the liver in myocardial ischemia.
Figure 4:
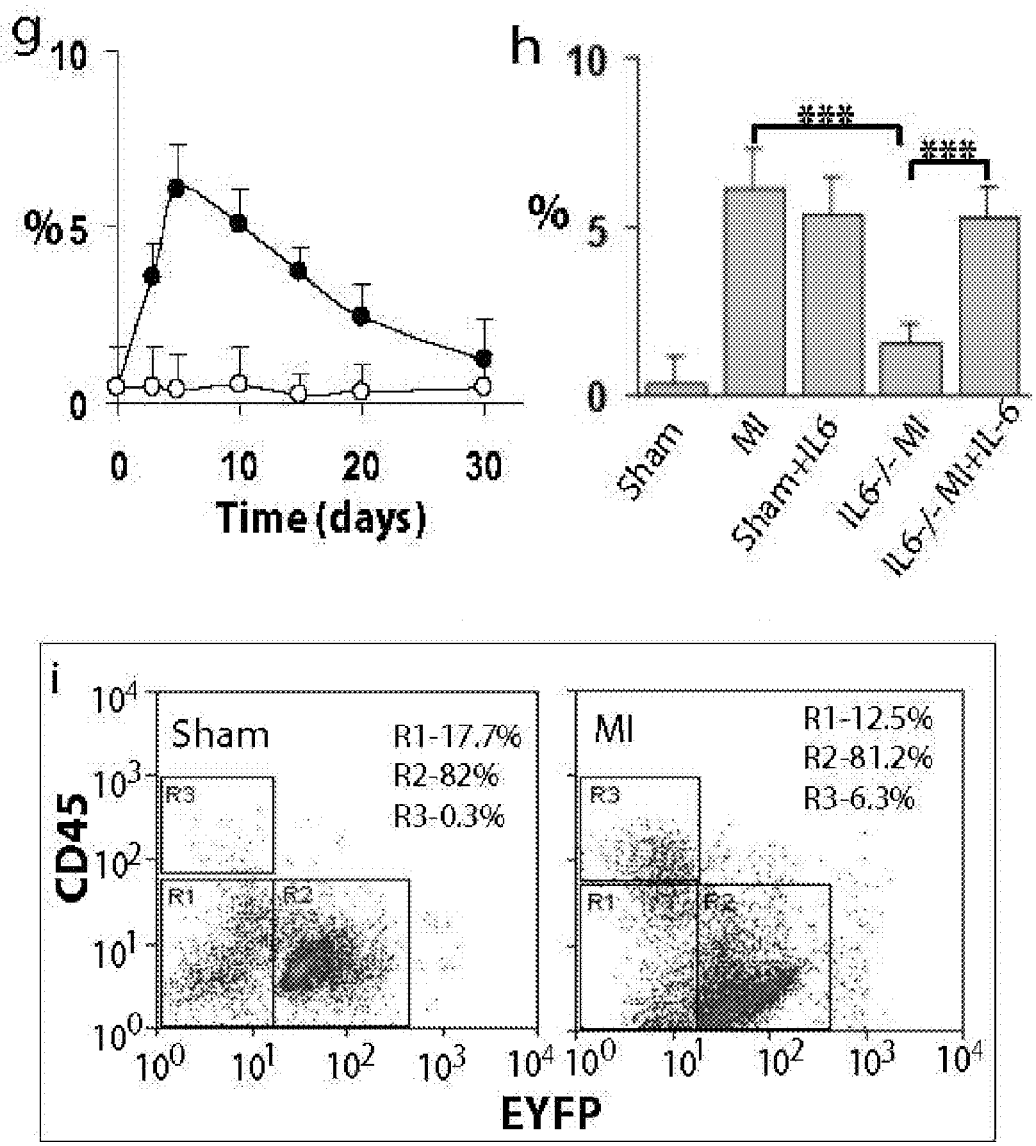

To assess whether IL-6 induces hepatic cell mobilization via the mediation of leukocytes, leukocyte retention was tested in the liver parenchyma of mice with and without IL-6 deficiency in myocardial ischemia. As shown in FIGS. 4a, 4b, and 4g, the density of retained leukocytes in the liver parenchyma (in the gaps between hepatocyte plates) of Cre-EYFP mice with myocardial ischemia was significantly higher than that in mice with sham operation. IL-6 deficiency resulted in a significant reduction in leukocyte retention in myocardial ischemia (FIGS. 4e and 4h). Administration of IL-6 (50 ng/gm×2 per day) to Cre-EYFP-IL-6$^{-/-}$ mice restored leukocyte retention in the liver parenchyma (FIGS. 4f and 4h), suggesting that IL-6 mediated leukocyte retention.

It is important to note that, in control mice without surgery, there exists a population of CD45+ cells in the liver about 0.3% of the total liver cells. These cells were present in the form of cluster and were primarily found in regions around the bile ducts and blood vessels (FIG. 1b). They were rarely found in the liver parenchyma under physiological conditions. In contrast, CD45+ cell retention in the liver parenchyma was found in mice with myocardial ischemia, but not in mice without surgery or with sham-operation. The population of retained CD45+ cells in the liver parenchyma in myocardial ischemia (about 6% of the total liver cells at day 5) was significantly larger than that found around the bile ducts and blood vessels under physiological conditions (about 0.3%) (FIGS. 4h and 4i).

Figure 5:
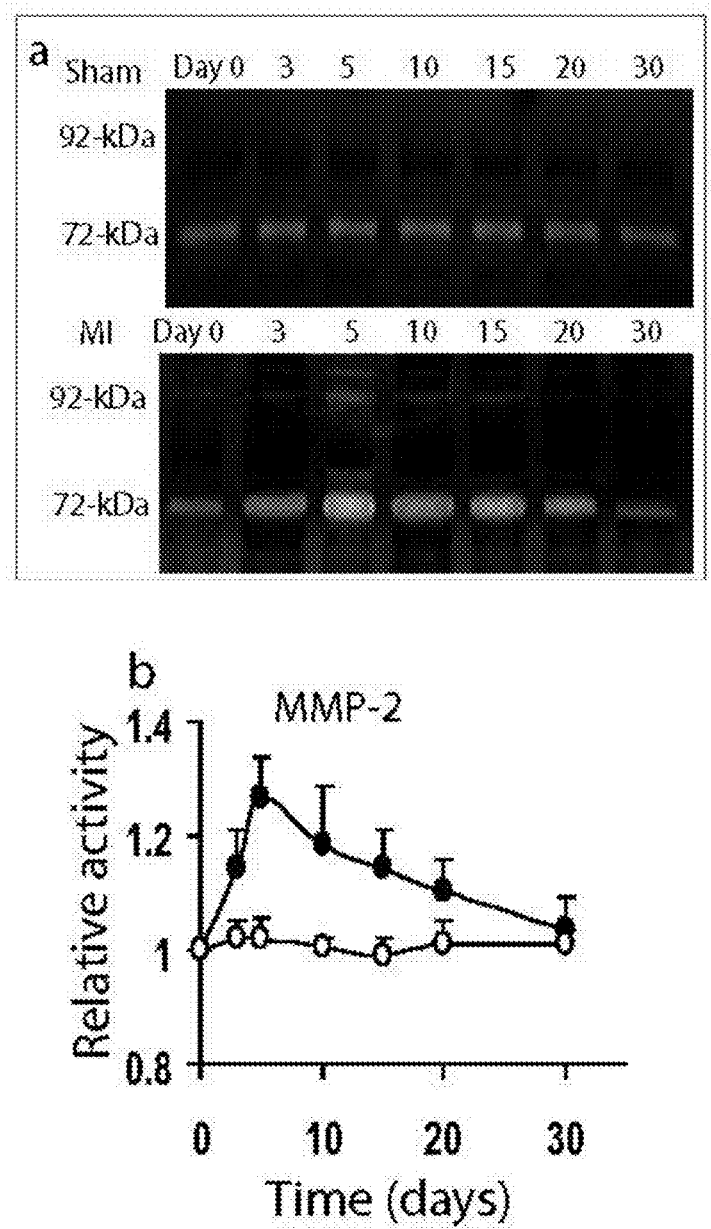
FIG. 5. Contribution of leukocytes to MMP-2 activation in the liver and role of IL-6 in regulating MMP-2 expression and activation. (a) Gelatin zymographs showing the relative activity of MMP-2 (~72 kDa) and MMP-9 (~92 kDa) in the liver of mice with sham operation and myocardial ischemia from day 0 to 30. Specimens at time zero were prepared from mice without surgical operation. Note that the activity of MMP-2 was significantly higher than that of MMP-9 in the same specimens from mice with myocardial ischemia. (b) Measured relative activity of MMP-2 in the liver of mice with sham operation (open circles) and myocardial ischemia (solid circles). The relative activity of MMP-2 was normalized with reference to the relative activity of MMP-2 at time zero. Mean and SD are presented ($p<0.001$ for changes in myocardial ischemia by ANOVA, n=6). (c, d) RT-PCR analysis of the relative MMP-2 mRNA level in CD45+ cells retained in the liver parenchyma (panel c) and hepatic cells (excluding CD45+ cells, panel d) from the liver of mice with sham operation and myocardial ischemia from day 0 to 30. (e, f) Measured relative level of the MMP-2 mRNA in CD45+ cells retained in the liver parenchyma (panel e) and hepatic cells (excluding CD45+ cells, panel f) from the liver of mice with sham operation (open circles) and myocardial ischemia (solid circles) from day 0 to 30. The relative MMP-2 mRNA level was normalized with reference to the relative GAPDH mRNA level of the same specimens. Mean and SD are presented ($p<0.001$ by ANOVA for changes in myocardial ischemia in panel e, n=6). For panel c-f, specimens at time zero were collected from mice without surgical operation. (g) RT-PCR analysis showing the influence of IL-6 on the relative MMP-2 mRNA level in CD45+ cells retained in the liver parenchyma of IL-6-/- mice. (h) Measured relative level of the MMP-2 mRNA in CD45+ cells retained in the liver parenchyma of IL-6-/- mice with myocardial ischemia with and without IL-6 administration. The relative MMP-2 mRNA level was normalized with reference to the relative GAPDH mRNA level of the same specimens. Mean and SD are presented (n=6). (i) Gelatin zymograph showing the influence of IL-6 on the relative activity of MMP-2 in the liver of IL-6-/- mice. (j) Measured relative activity of MMP-2 in the liver of IL-6-/- mice with myocardial ischemia with and without IL-6 administration. The relative activity of MMP-2 was normalized with reference to the relative activity of MMP-2 from the sham control. Mean and SD are presented (n=6). MI: Myocardial ischemia. (k) Gelatin zymograph showing the influence of IL-6 (50 ng/ml), leukocytes (~105 cells/ml), or leukocytes (~105 cells/ml)+IL-6 (50 ng/ml) on the relative activity of MMP-2 in cultured liver specimens at day 5. The first lane is for culture medium without liver specimens. L: leukocytes. (l) Measured relative activity of MMP-2 in cultured liver specimens in the presence of IL-6 (50 ng/ml), leukocytes (~105 cells/ml), or leukocytes (~105 cells/ml)+IL-6 (50 ng/ml) at day 5. The relative activity of MMP-2 was normalized with reference to the relative activity of MMP-2 from the liver-only group. Mean and SD are presented (n=6). For panels h, j, and l, *$p<0.05$, $p<0.01$, *$p<0.001$.
Figure 5:
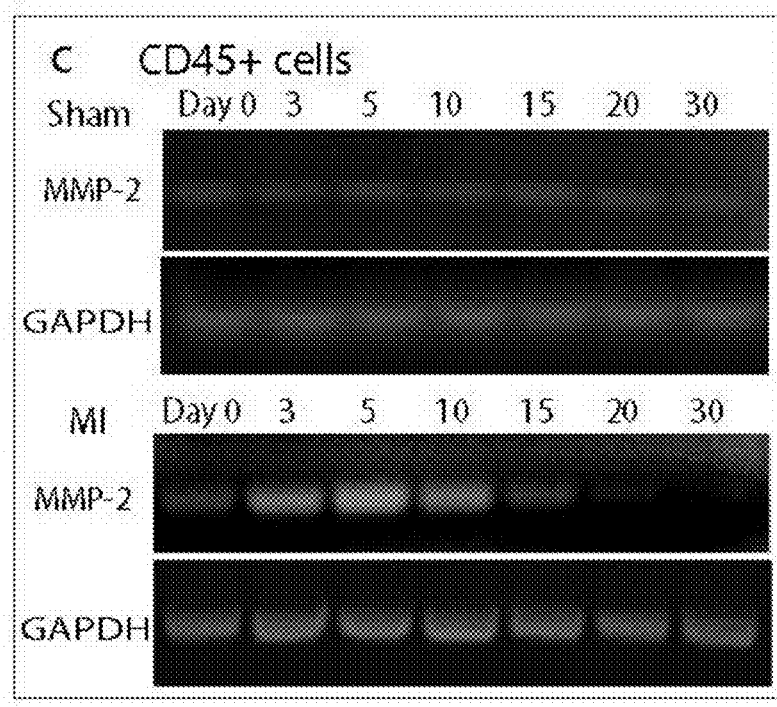
Figure 5:
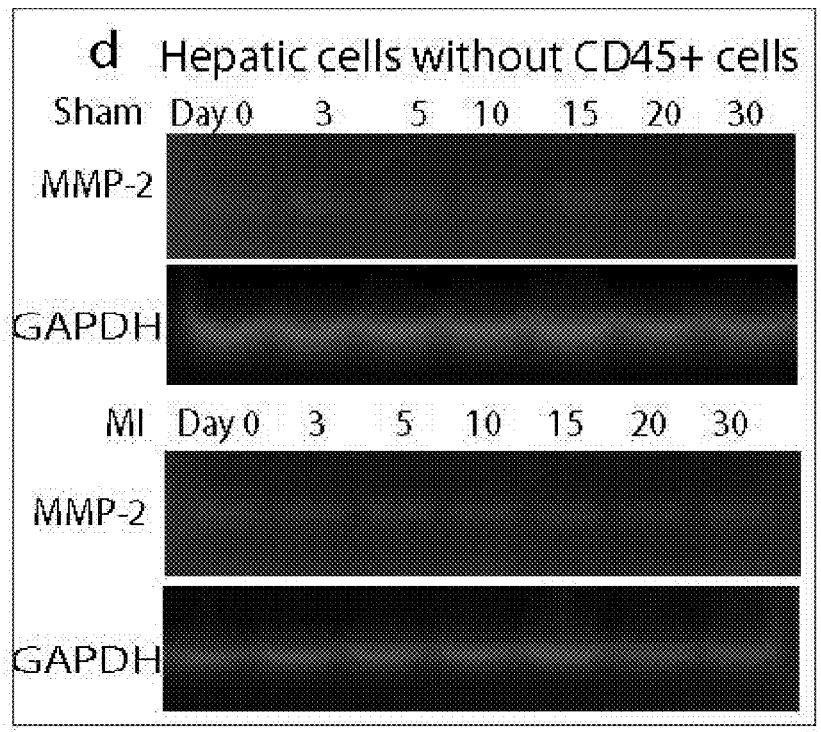
Figure 5:
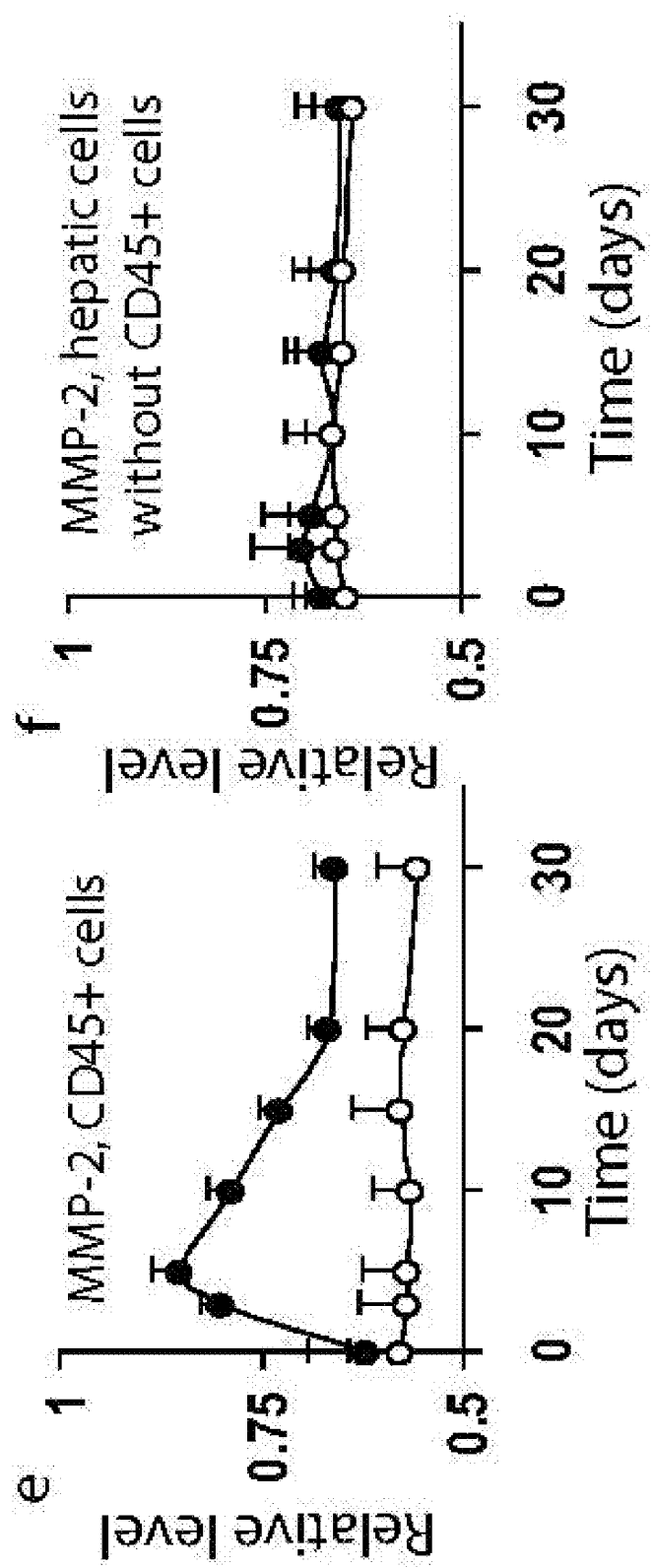
Figure 5:
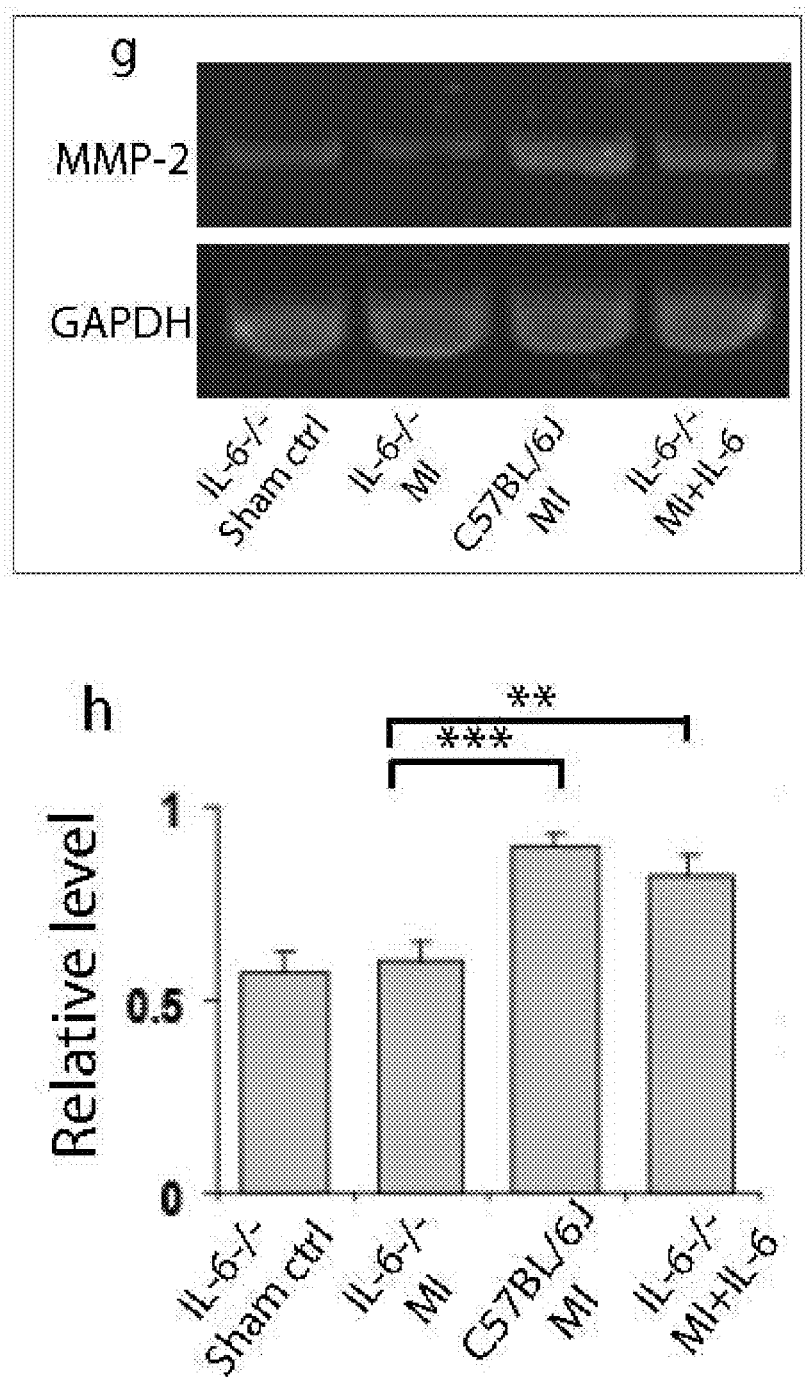
Figure 5:
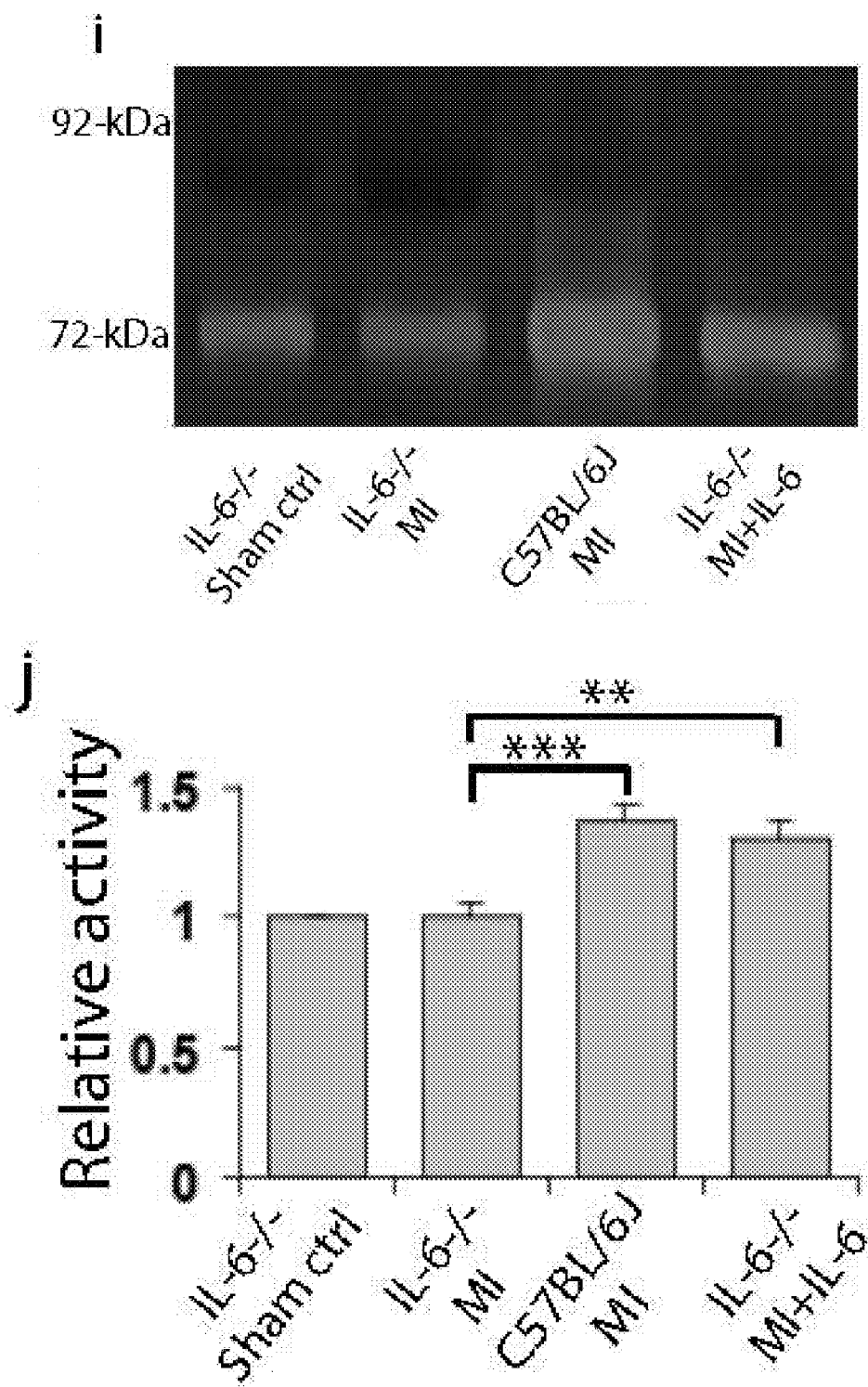
Figure 5:
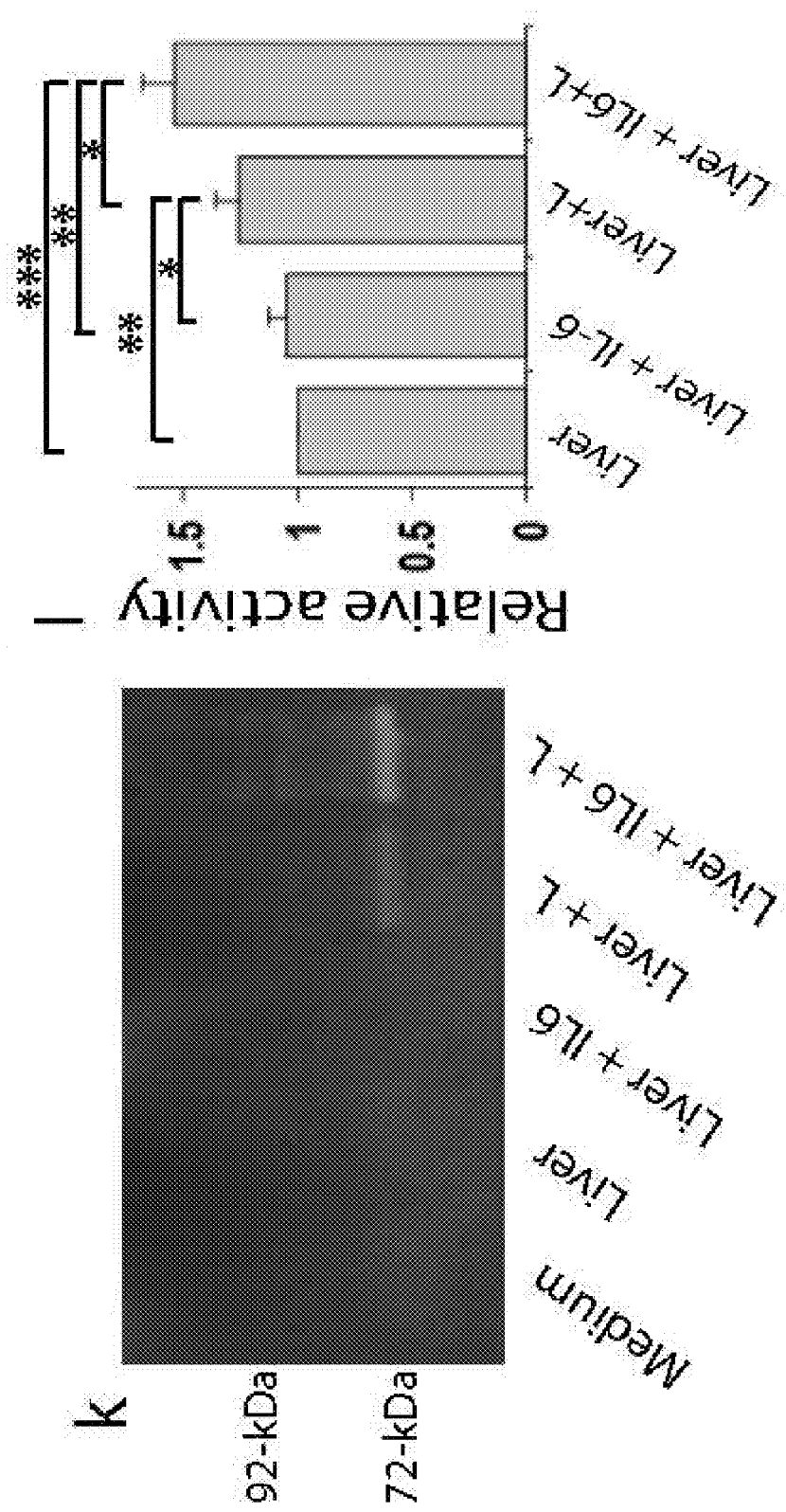

MMP-2 Upregulation in Leukocytes Retained in the Liver Parenchyma in Myocardial Ischemia The liver exhibited a significant increase in the activity of MMP-2, but not MMP-9, in myocardial ischemia (FIGS. 5a and 5b). Thus, MMP-2 expression was tested by RT-PCR in liver-derived cells, including leukocytes and hepatic cells without leukocytes, in myocardial ischemia. Leukocytes retained in the liver, but not hepatic cells, exhibited a significant increase in MMP-2 expression in myocardial ischemia (FIG. 5c-5f). This result was supported by fluorescence microscopy, demonstrating MMP-2 expression in leukocytes retained in the liver parenchyma (FIG. 4c). These observations suggest that leukocytes primarily contributed to MMP-2 upregulation in the liver. In IL-6$^{-/-}$ mice, the MMP-2 expression level in leukocytes and MMP-2 activity in the liver were significantly reduced in myocardial ischemia compared to that in Cre-EYFP and C57BL/6J mice. IL-6 administration to IL-6$^{-/-}$ mice restored leukocyte MMP-2 expression and hepatic MMP-2 activity (FIG. 5g-5j). These findings suggest that IL-6 stimulates not only leukocyte retention in the liver parenchyma, but also leukocyte upregulation of MMP-2 in myocardial ischemia.

To demonstrate the effect of IL-6 and leukocytes on MMP-2 activation, liver specimens derived from IL-6$^{-/-}$ mice were cultured and tested in the presence of IL-6, leukocytes, or both. As shown in FIGS. 5k and 5l, the presence of IL-6 alone (50 ng/ml) did not induce MMP-2 activation in cultured liver specimens, whereas the presence of leukocytes (~10$^5$/ml) induced MMP-2 activation. Application of IL-6 (50 ng/ml) to liver specimens in the presence of leukocytes (~10$^5$/ml) significantly enhanced MMP-2 expression in leukocytes and MMP-2 activity in the liver specimens (FIGS. 5k and 5l), confirming the role of IL-6 in stimulating MMP-2 expression in leukocytes.

Role of MMP-2 in Inducing Hepatic Cell Mobilization

MMP-2 is a proteinase that degrades collagen, gelatin, and elastin, a process that induces cell mobilization. To demonstrate the role of MMP-2 in mediating hepatic cell mobilization, an anti-MMP-2 antibody (100 ng/gm×2 per day) was delivered to Cre-EYFP mice with myocardial ischemia for 5 days via venous injection and measured the relative population of blood-borne EYFP-positive cells. This modulation significantly reduced hepatic cell mobilization (0.59+/−0.12% with reference to total nucleated blood cells, n=7) compared to administration of an isotype-matched control antibody (1.92+/−0.29%, n=7, p<0.001). It was also found that CD45+ cells were associated with mobilized EYFP+ hepatic cells present within the liver central veins (FIG. 4d). While the present invention is not limited to any particular mechanism and an understanding of the mechanism is not necessary to practice the invention: 1) given the observation that leukocytes express MMP-2, the association of leukocytes may facilitate hepatic cell mobilization, and 2) collectively, these observations suggest that leukocytes express and release MMP-2, which in turn mediates hepatic cell mobilization.

Engraftment of Hepatic Cells to Ischemic Lesions of Myocardium

Figure 6:
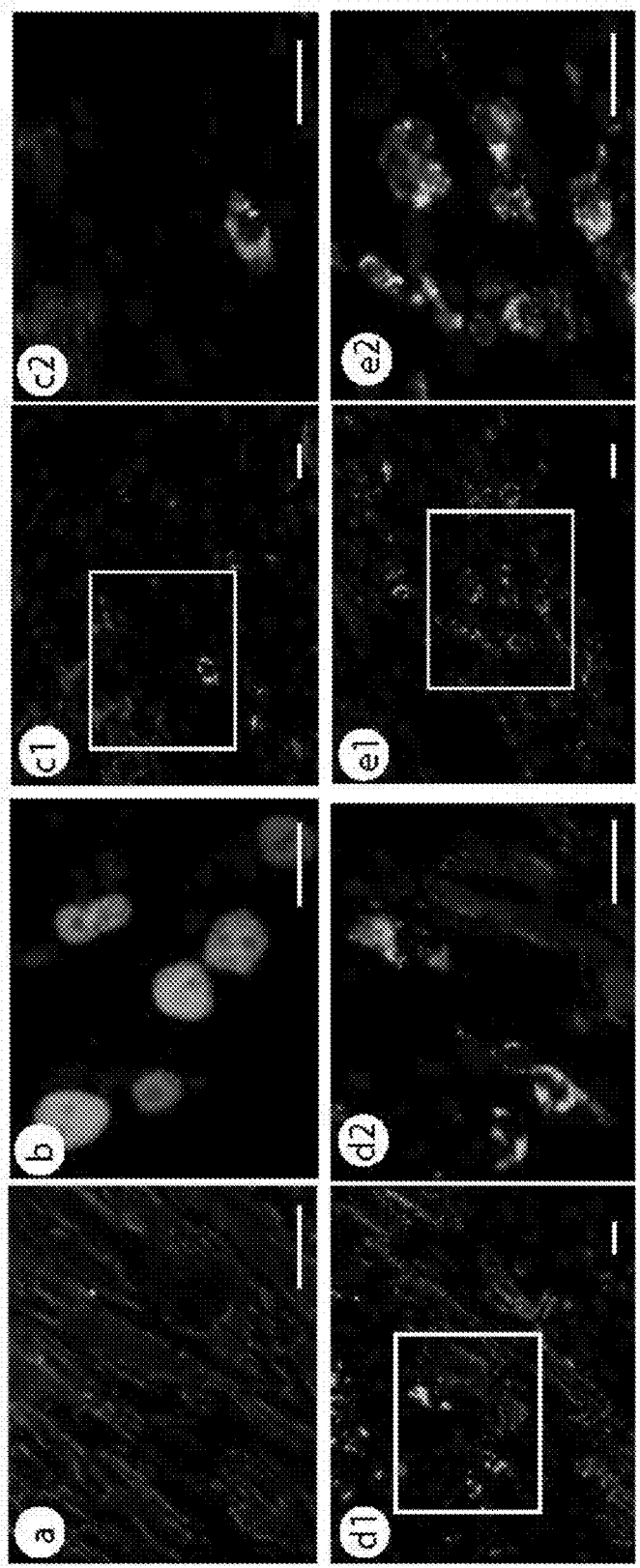
FIG. 6. Recruitment of EYFP+ hepatic cells to the ischemic lesion of myocardium. (a) Fluorescence micrograph showing the left ventricular myocardium of a Cre-EYFP mouse with sham operation at day 5. (b) Fluorescence micrograph showing EYFP+ hepatic cells isolated from the liver of a Cre-EYFP mouse. (c) Fluorescence micrographs showing EYFP+ cells recruited to the ischemic myocardium of a Cre-EYFP mouse at day 5. Panel c2 is a magnified image of the area (white rectangle) selected from c1. (d) Enhanced recruitment of EYFP+ cells to the ischemic myocardium of a Cre-EYFP mouse at day 5 with venous transplantation of hepatic cells derived from the liver of a Cre-EYFP mouse with 5-day myocardial ischemia. Panel d2 is a magnified image of the area (white rectangle) selected from d1. For panel a-d, one shade of gray is for cardiac troponin I, another shade is for EYFP, and another is for cell nuclei. (e) Fluorescence micrographs showing EYFP+ cells and CD45+ cells recruited to the ischemic myocardium of a Cre-EYFP mouse with hepatic cell transplantation at day 5. Panel e2 is a magnified image of the area (white rectangle) selected from e1. Note that CD45+ cells did not express EYFP. For panel a-e, the scale bars are 10 um. (f) Relative population size of EYFP+ cells in the myocardium of Cre-EYFP mice with sham operation (open circles) and in the ischemic lesion of myocardium (solid circles) at day 3, 5, 10, 15, 20, and 30 measured by fluorescence microscopy. Mean and SD are presented (p<0.001 for changes in myocardial ischemia by ANOVA, n=6). Specimens at time zero were prepared from Cre-EYFP mice without surgical operation. (g) Two-dimensional cytometry analysis of EYFP+ and CD45+ cells from the ischemic lesion of myocardium of C57BL/6J and Cre-EYFP mice with 5-day myocardial ischemia. (h) One-dimensional cytometry analysis of EYFP+ cells from the liver of Cre-EYFP and C57BL/6J mice with sham operation, the ischemic myocardium of C57BL/6J mice, and the ischemic myocardium of Cre-EYFP mice with leukocyte or hepatic cell transplantation (LT or HT, respectively). A standard level of fluorescence intensity (the left side of the rectangle) was established from the EYFP+ hepatic cells of Cre-EYFP mice as described in the method section and used for assessing the population of EYFP+cells. The fraction shown in each panel represents the mean and standard deviation of the EYFP+ cell population from 6 tests.
Figure 6:
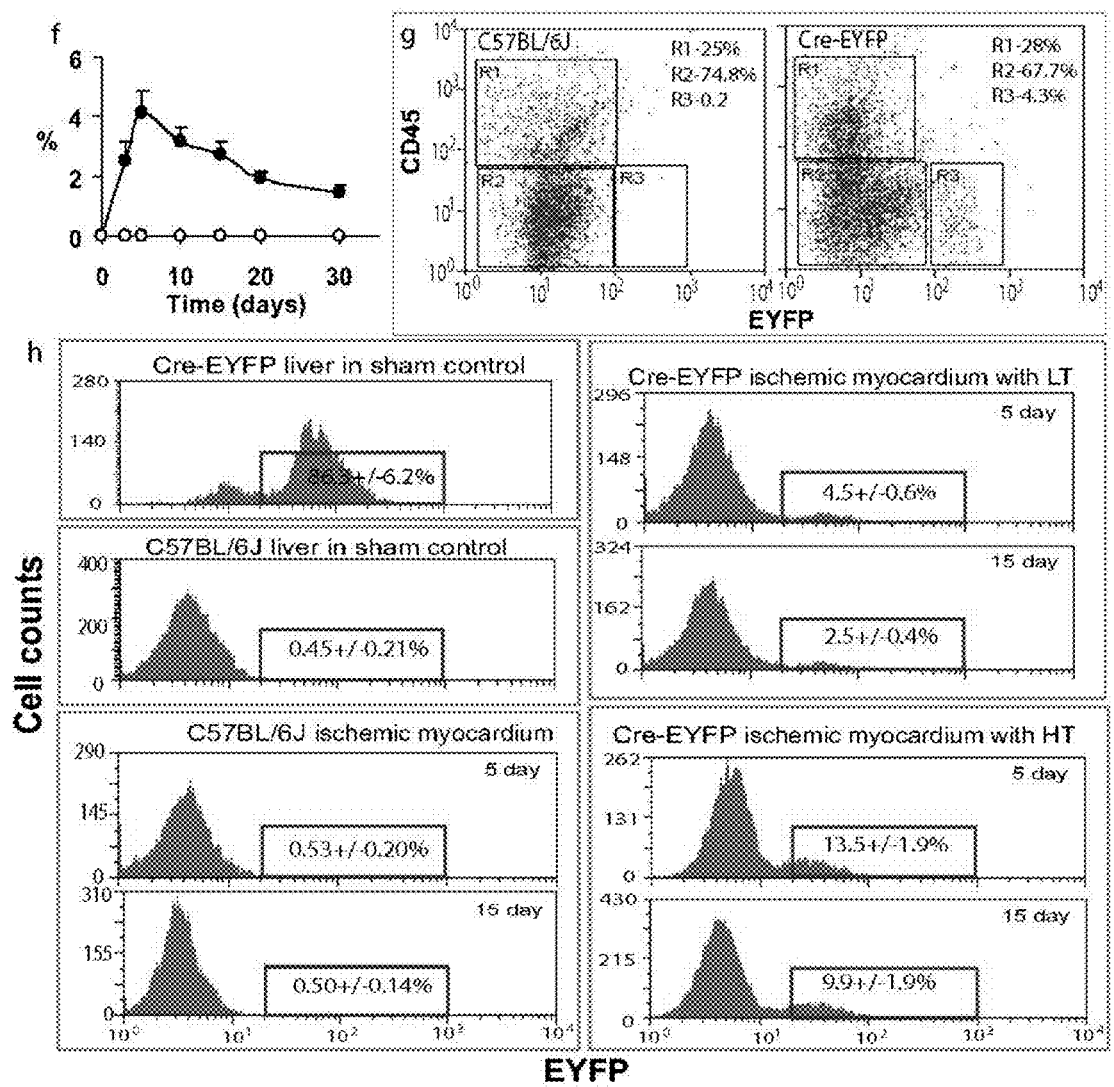

Hepatic cells were mobilized in response to myocardial ischemia, possibly supporting the survival of cardiomyocytes. To test this possibility, it was assessed whether mobilized hepatic cells could engraft to the ischemic lesion of myocardium. As shown in FIG. 6, EYFP-positive cells were found in the ischemic myocardium of Cre-EYFP mice (FIG. 6c), but not in the myocardium of Cre-EYFP mice with sham operation (FIG. 6a) as tested by fluorescence microscopy. These cells were detectable as early as at day 3 following coronary arterial ligation, reached a peak population at day 5, and reduced in population size afterwards (FIG. 6σ. Results from fluorescence microscopy were confirmed by flow cytometry at selected times (FIG. 6h). These observations demonstrate that mobilized hepatic cells can engraft to the ischemic lesion of myocardium. CD45+ cells were also found in the ischemic lesion of myocardium. These cells did not express EYFP and could be readily distinguished from the engrafted EYFP+cells (FIGS. 6e and 6g).

HGF Upregulation in Hepatic Cells of the Liver in Myocardial Ischemia

Figure 7:
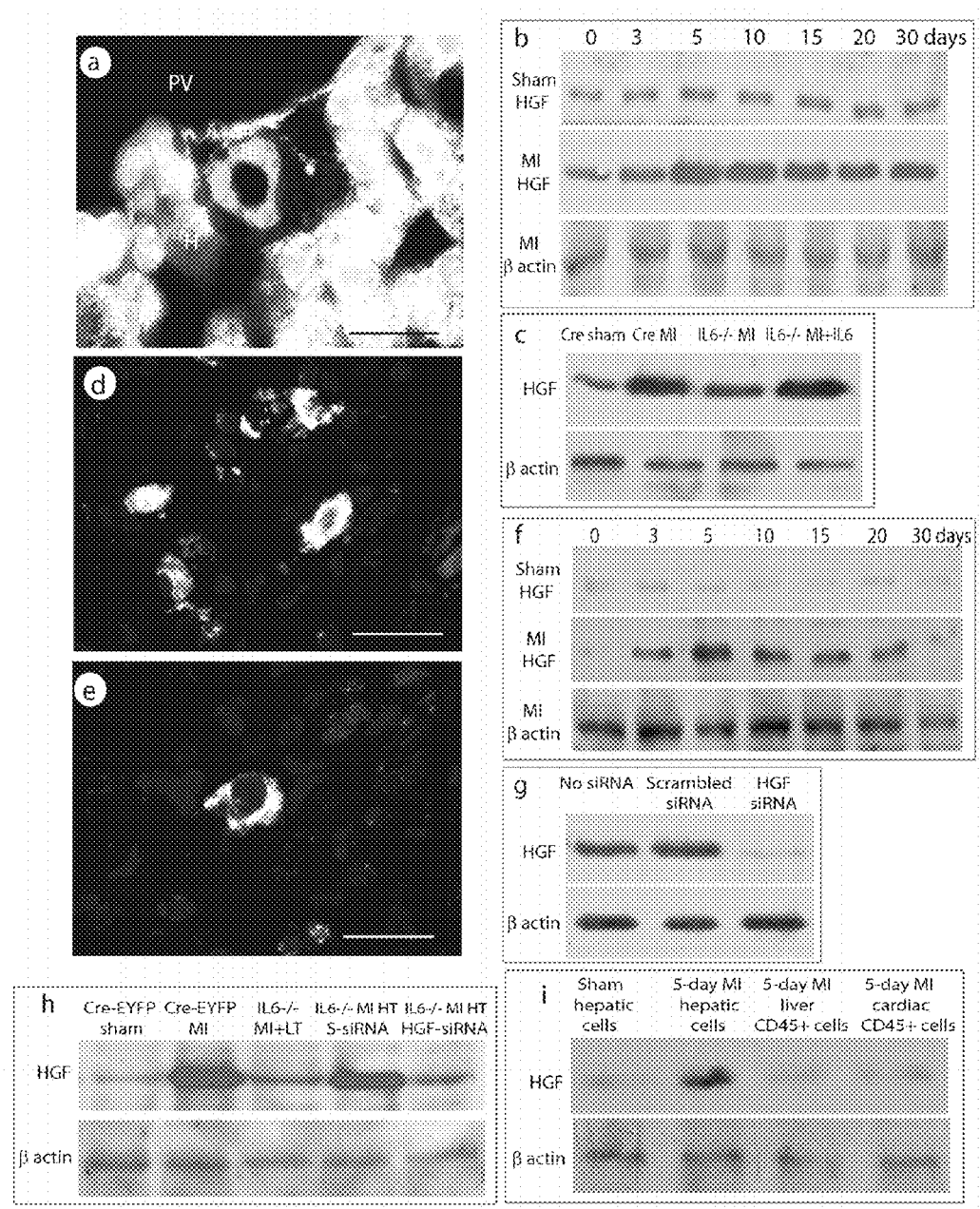
FIG. 7. Contribution of mobilized hepatic cells to HGF upregulation in ischemic myocardium. (a) Fluorescence micrograph showing the expression of HGF in EYFP+hepatocytes in the liver of a Cre-EYFP mouse with 5-day myocardial ischemia. H: hepatocytes. BE: Biliary epithelial cells. PV: Portal venule. Scale: 10 um. (b) Immunoblotting analysis of HGF expression in hepatic cells isolated from the liver of Cre-EYFP mice with sham operation and myocardial ischemia (MI). Specimens at zero time were prepared from mice without surgical operation. (c) Influence of IL-6 on HGF expression in hepatic cells isolated from the liver of mice with myocardial ischemia (MI). Cre: Cre-EYFP mice. (d, e) HGF expression in EYFP+ cells recruited to the ischemic myocardium of Cre-EYFP mice at day 5 (panel d) and 30 (panel e). Scale: 10 um. Note that the EYFP+ cells were a major cell type that expressed HGF. (f) Immunoblotting analysis of HGF expression in sham control and ischemic myocardium of Cre-EYFP mice at day 3, 5, 10, 15, 20, and 30. Specimens at zero time were prepared from mice without surgical operation. (g) Immunoblotting analysis showing knockdown of HGF expression in isolated hepatic cells in vitro by transfection with HGF-specific siRNA at day 3. (h) Immunoblotting analysis of HGF expression in the ischemic myocardium of IL-6-/- mice with transplantation of leukocytes (LT) or hepatic cells (HT) transfected with scrambled (S) siRNA or HGF-specific siRNA. MI: myocardial ischemia. (i) Immunoblotting analysis of HGF expression in hepatic cells isolated from the liver of mice with sham operation and myocardial ischemia as well as CD45+ cells isolated from the liver and ischemic lesion of mice with myocardial ischemia at day 5.

Hepatic cells were capable of expressing HGF (FIGS. 7a and 7b), a growth factor that exerts cardioprotective effects, including promotion of cardiomyocyte survival, alleviation of myocardial fibrosis, and mobilization of resident cardiac progenitor cells to ischemic myocardium. It was found that hepatic cells of the liver exhibited a significant increase in HGF expression in response to myocardial ischemia (relative HGF level with reference to the control level without surgical operation: 1.23+/−0.11, 1.54+/−0.22, 1.36+/−0.21, 1.33+/−0.20, 1.23+/−0.18, and 1.19+/−0.18 at day 3, 5, 10, 15, 20, and 30, respectively, n=6, ANOVA p<0.01, FIG. 7b), while no significant changes were found in sham-operated mice. HGF upregulation in the hepatic cells was possibly regulated by IL-6 as HGF expression was significantly reduced in IL-6$^{-/-}$ mice (relative HGF level: 1.10+/−0.11, n=6) compared to that in Cre-EYFP mice (relative HGF level: 1.54+/−0.22, n=6, p<0.01) at day 5 of myocardial ischemia (FIG. 7c). Administration of IL-6 (50 ng/gm×2 per day) to IL-6$^{-/-}$ mice with myocardial ischemia resulted in a significant increase in hepatic cell expression of HGF in the liver (relative level: 1.43+/−0.36, n=6, p<0.05, FIG. 7c). HGF upregulation in hepatic cells occurred simultaneously with hepatic cell mobilization in myocardial ischemia, suggesting a possibility that HGF expression may be one of the mechanisms by which mobilized hepatic cells contribute to cardioprotection.

Contribution of Mobilized Hepatic Cells to HGF Upregulation in Ischemic Myocardium Myocardial ischemia was associated with HGF upregulation in the ischemic lesion of myocardium (relative expression with reference to the control level without surgical operation: 1.68+/−0.40, 2.24+/−0.69, 1.91+/−0.58, 1.70+/−0.46, 1.50+/−0.44, 1.23+/−0.32 at day 3, 5, 10, 15, 20, and 30, respectively, n=6, ANOVA p<0.001, FIG. 7f), while no significant changes were found in the myocardium of mice with sham operation. Hepatic cells recruited to the ischemic lesion of myocardium were a major cell population expressing HGF (FIGS. 7d and 7e). To test whether mobilized hepatic cells contributed to myocardial HGF upregulation, hepatic cells were isolated from the liver of Cre-EYFP mice with 5-day myocardial ischemia and modulated HGF expression in these cells by transfection with HGF-specific siRNA or scrambled siRNA as described[45,46]. While scrambled siRNA transfection did not significantly influence HGF expression, HGF-siRNA transfection induced a 77.3+/−5.1% decrease in HGF expression (n=6) from the relative HGF level with scrambled siRNA transfection (n=6, p<0.001, FIG. 7g). The siRNA-modulated hepatic cells (~$10^5$) were transplanted to IL-6$^{-/-}$ mice via venous injection following coronary arterial ligation. In IL-6$^{-/-}$ mice transplanted with allogenic leukocytes (a control cell type), HGF expression in the ischemic myocardium (relative expression with reference to the control level of sham-operated mice: 1.11+/−0.16, n=6) was significantly lower than that in Cre-EYFP mice (1.76+/−0.25, n=6, p<0.01, FIG. 7h). The transplantation of scrambled siRNA-transfected hepatic cells, which resulted in increased engraftment of hepatic cells to ischemic myocardium, induced a significant increase in HGF expression in the ischemic myocardium of IL-6$^{-/-}$ mice (1.77+/−0.27, n=6) compared to leukocyte transplantation (1.11+/−0.16, n=6, p<0.01, FIG. 7h). In IL-6$^{-/-}$ mice transplanted with HGF-siRNA-transfected hepatic cells, however, HGF expression in the ischemic myocardium (1.22+/−0.22, n=6) was significantly lower than that in IL-6$^{-/-}$ mice transplanted with scrambled siRNA-treated hepatocytes (1.77+/−0.27, n=6 p<0.01) and was not significantly altered from the HGF level in the ischemic myocardium of IL-6$^{-/-}$ mice with leukocyte transplantation (1.11+/−0.16, n=6, FIG. 7h). These observations support the contribution of mobilized hepatic cells to HGF upregulation in the ischemic myocardium.

Leukocytes were able to migrate to the ischemic lesion of myocardium (FIGS. 6e and 6g) and were a possible cell population contributing to HGF upregulation. To test this possibility, HGF expression was detected and analyzed in CD45+ cells derived from the liver and ischemic myocardium of mice with 5-day myocardial ischemia with reference to HGF expression in hepatic cells derived from mice with myocardial ischemia. As shown in FIG. 7i, the expression of HGF in CD45+ cells derived from the liver and ischemic myocardium of mice with myocardial ischemia appeared considerably lower than that in hepatic cells derived from the liver of mice with myocardial ischemia. These findings support the contribution of hepatic cells to HGF upregulation in the ischemic lesion of myocardium.

Contribution of Hepatic Cells to Cardioprotection in Myocardial Ischemia

Figure 8:
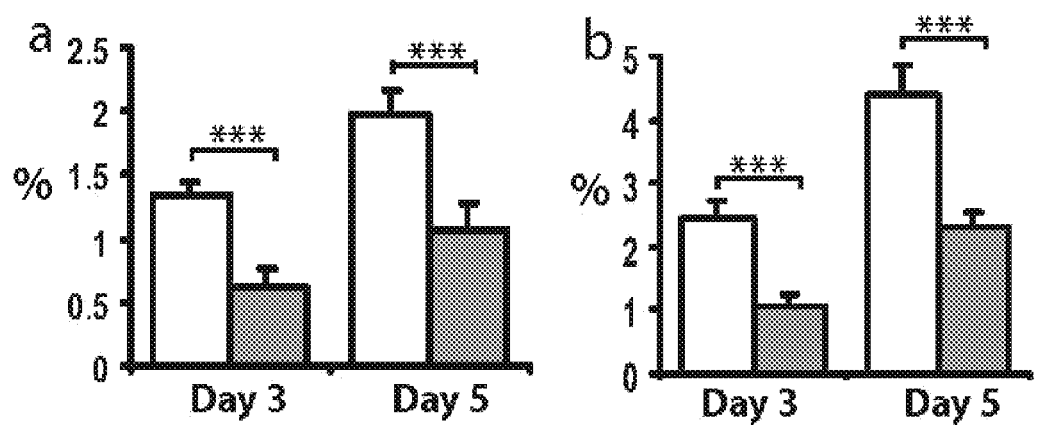
FIG. 8. Impairment of cardioprotection in response to reduced hepatic cell mobilization by partial hepatectomy (~60% removal of the liver mass) in myocardial ischemia. (a) Reduction in the relative density of EYFP+ hepatic cells mobilized to the circulatory system in myocardial ischemia with partial hepatectomy. White bars: Myocardial ischemia with sham liver operation. Dark gray bars: Myocardial ischemia with partial hepatectomy. *p<0.001. (b) Reduction in the relative density of EYFP+ hepatic cells recruited to the ischemic myocardium of mice with partial hepatectomy. White bars: Myocardial ischemia with sham liver operation. Dark gray bars: Myocardial ischemia with partial hepatectomy. *p<0.001. (c-e) Fluorescence micrographs showing retention of CD45+ cells in the liver parenchyma of mice with partial hepatectomy without myocardial ischemia (panel c, c2 is a magnified image of the area selected from c1), myocardial ischemia with sham liver operation (panel d, d2 is a magnified image of the area selected from d1), and myocardial ischemia with partial hepatectomy (panel e, e2 is a magnified image of the area selected from e1). Scale: 10 um. (f) Gelatin zymograph showing the relative activity of MMP-2 in the liver of mice with sham heart operation (Sham), myocardial ischemia with sham liver operation (MI), and myocardial ischemia with partial hepatectomy (MI+H). (g) Immunoblotting analyses of HGF expression in the myocardium of mice with sham heart operation (Sham), myocardial ischemia with partial hepatectomy (MI+H), myocardial ischemia with sham liver operation (MI), and myocardial ischemia with partial hepatectomy and hepatic cell transplantation (MI+H+T). (h-l) Fluorescence micrographs showing TUNEL+ myocardial nuclei (green) in mice with sham heart operation (panel h), sham heart operation and partial hepatectomy (panel i), myocardial ischemia and sham liver operation (panel j), myocardial ischemia and partial hepatectomy (panel k), and myocardial ischemia, partial hepatectomy, and hepatic cell transplantation (panel 1) at day 1. Scale: 10 um. (m) Comparison of TUNEL+ myocardial nucleus density between three groups: myocardial ischemia+sham liver operation (white bars), myocardial ischemia+partial hepatectomy (dark gray bars), and myocardial ischemia+partial hepatectomy+hepatic cell transplantation (light gray bars) at day 1, 3, and 5 following surgical operation. p<0.01. *p<0.001. (n-p) Histological micrographs of AZAN-stained myocardium showing myocardial infarcts (blue) in mice with myocardial ischemia+sham liver operation (panel n), myocardial ischemia+partial hepatectomy (panel o), and myocardial ischemia+partial hepatectomy+hepatic cell transplantation (panel p) at day 5 after surgical operation. Scale: 1 mm. (q) Comparison of the volume fraction of myocardial infarcts between three groups: myocardial ischemia+sham liver operation (MI), myocardial ischemia+partial hepatectomy (MI+H), and myocardial ischemia+partial hepatectomy+hepatic cell transplantation (MI+H+T). ***p<0.001.
Figure 8:
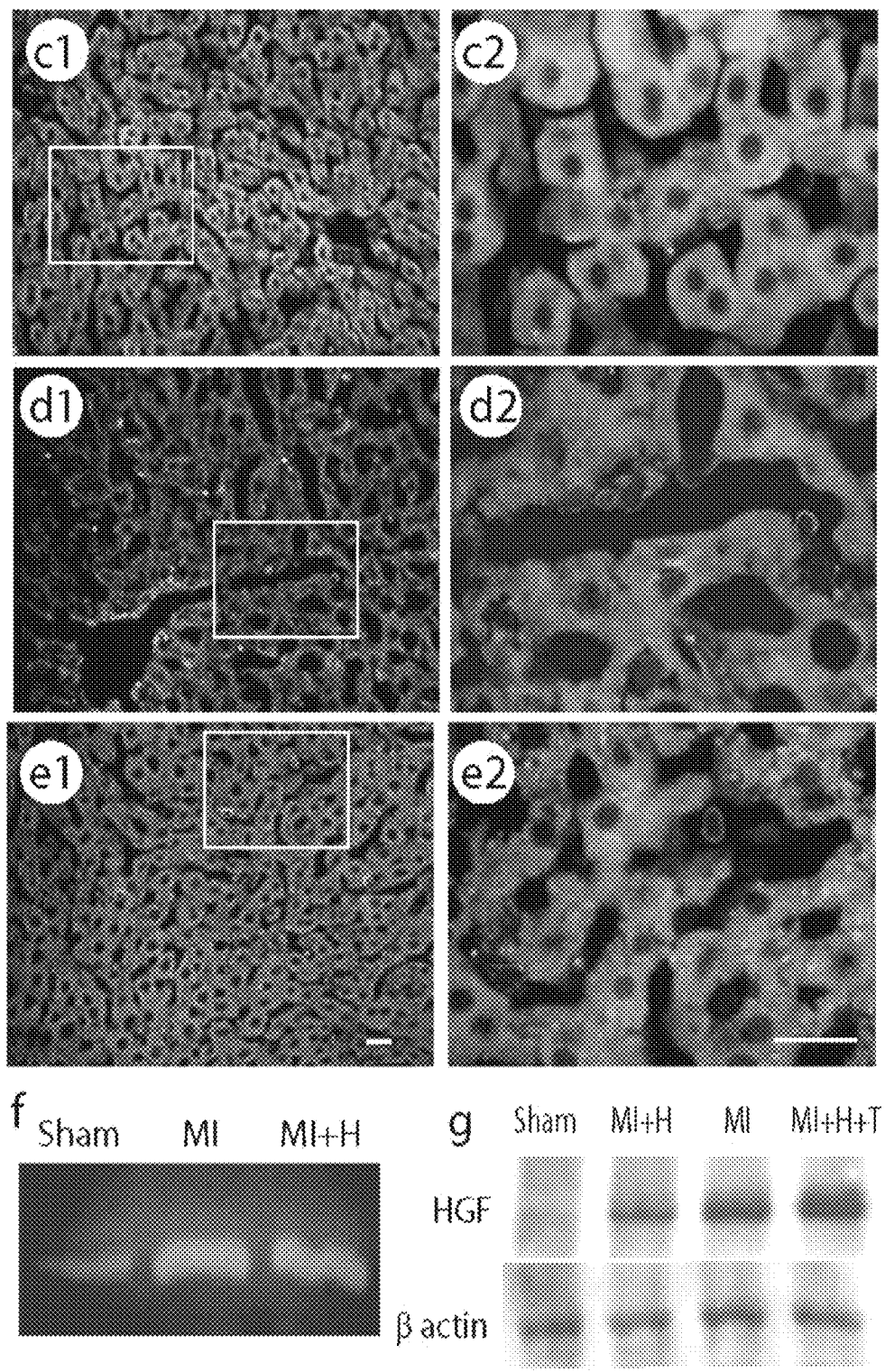
Figure 8:
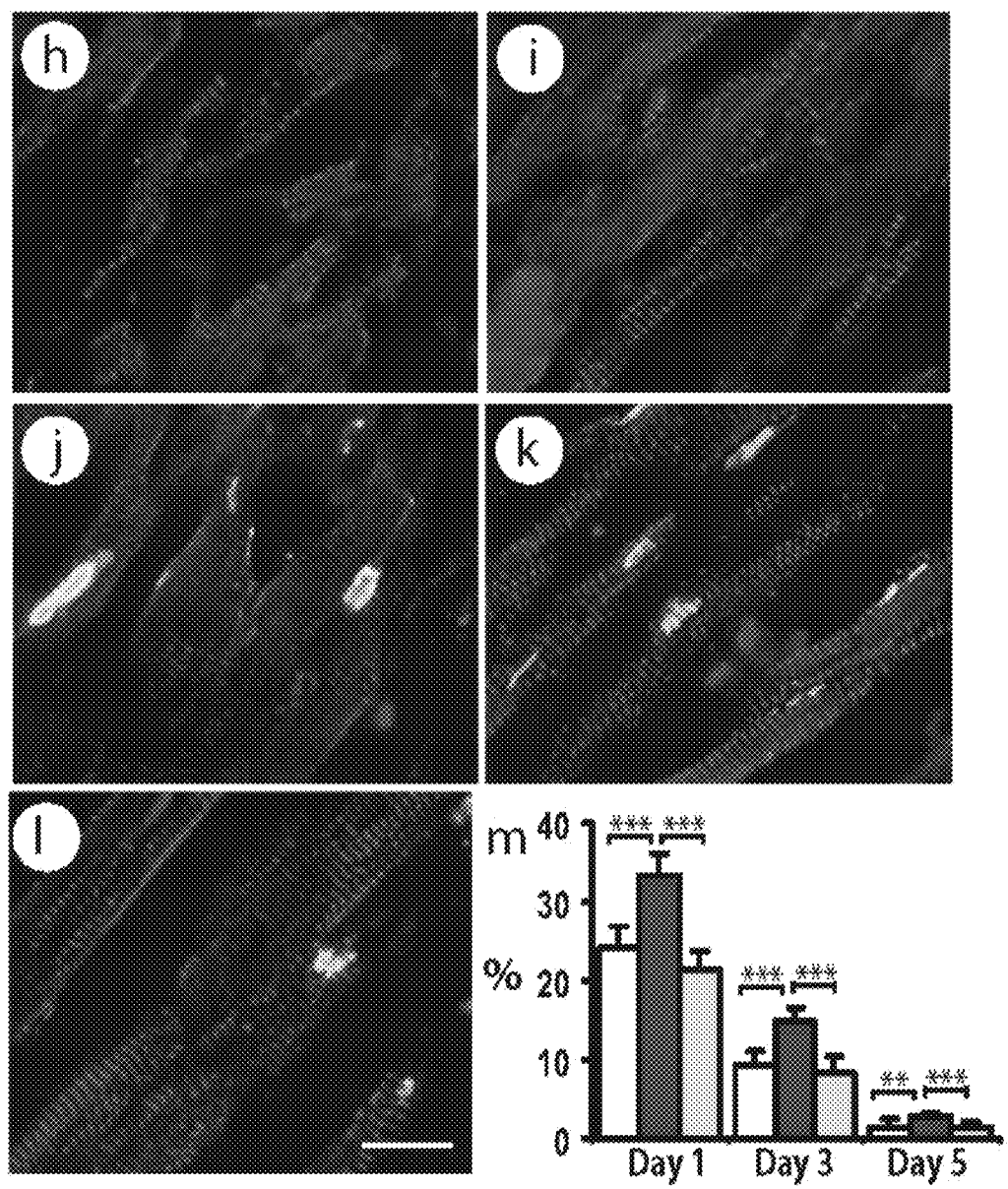
Figure 8:
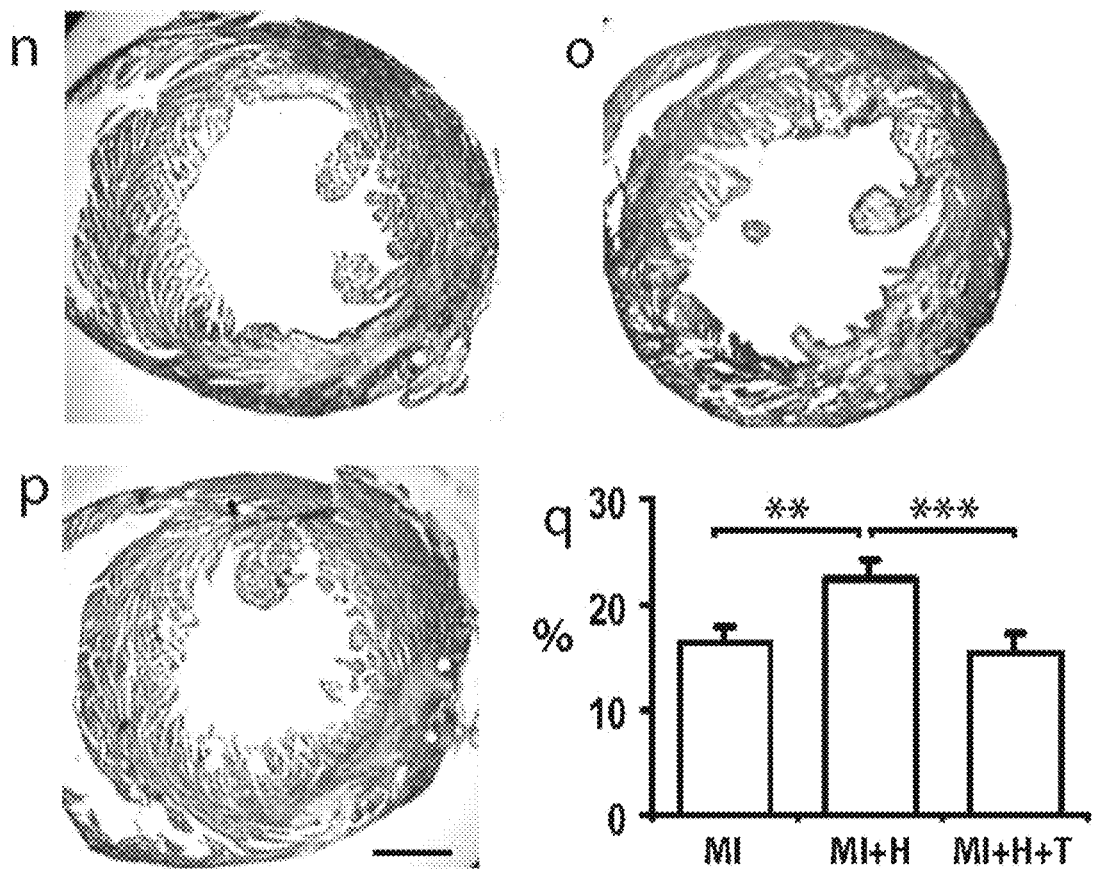

To test the role of the naturally mobilized hepatic cells in supporting myocardial survival, hepatic cell mobilization was suppressed by partial hepatectomy (~60% removal of the liver mass)[47] in Cre-EYFP mice with myocardial ischemia and measured the density of TUNEL+ myocardial nuclei and volume fraction of myocardial infarcts during the early 5 days as TUNEL+ cells and maximal hepatic cell mobilization were observed during this period. Following partial hepatectomy, the remaining liver regained about 22% of the original liver mass within 5 days. Partial hepatectomy resulted in a significant reduction in the relative density of blood-borne EYFP+ cells (FIG. 8a) as well as the relative density of EYFP+ cells recruited to the ischemic myocardium (FIG. 8b). As the density of leukocytes (a cell type expressing MMP-2) retained in the liver parenchyma (FIG. 8c-e) and the relative activity of liver MMP-2 (a proteinase mediating hepatic cell mobilization, FIG. 8f) did not change significantly in the remaining liver after partial hepatectomy, the loss of liver mass was responsible for the attenuation of hepatic cell mobilization. In response to the attenuation of hepatic cell mobilization and recruitment to the ischemic myocardium, the relative expression of HGF in the ischemic myocardium was reduced by 52.7+/−6.3% (p<0.001, n=5) from the level in myocardial ischemia with sham liver operation (FIG. 8g). As a result, the relative density of TUNEL+ myocardial nuclei (FIG. 8h-k, and 8m) and the volume fraction of myocardial infarcts (FIGS. 8n, 8o, and 8q) were increased significantly in myocardial ischemia with partial hepatectomy compared with that in myocardial ischemia with sham liver operation. To confirm the cardioprotective role of hepatic cells, hepatic cells (~$10^5$ cells/mouse) isolated from donor Cre-EYFP mice with 5-day myocardial ischemia were transplanted into mice with myocardial ischemia and partial hepatectomy. This modulation induced a 125.7+/−11.6% increase in the relative expression of HGF (p<0.001, n=5) from the level in myocardial ischemia with partial hepatectomy (FIG. 8g). HGF upregulation in response to hepatic cell transplantation was associated with a significant reduction in the density of TUNEL+ myocardial nuclei (FIG. 8k-m) and the volume fraction of myocardial infarcts (FIG. 8o-q) compared to that in myocardial ischemia with partial hepatectomy. These observations suggest that the maintenance of a natural level of mobilized hepatic cells is important to effective cardioprotection in myocardial ischemia.

Figure 10:
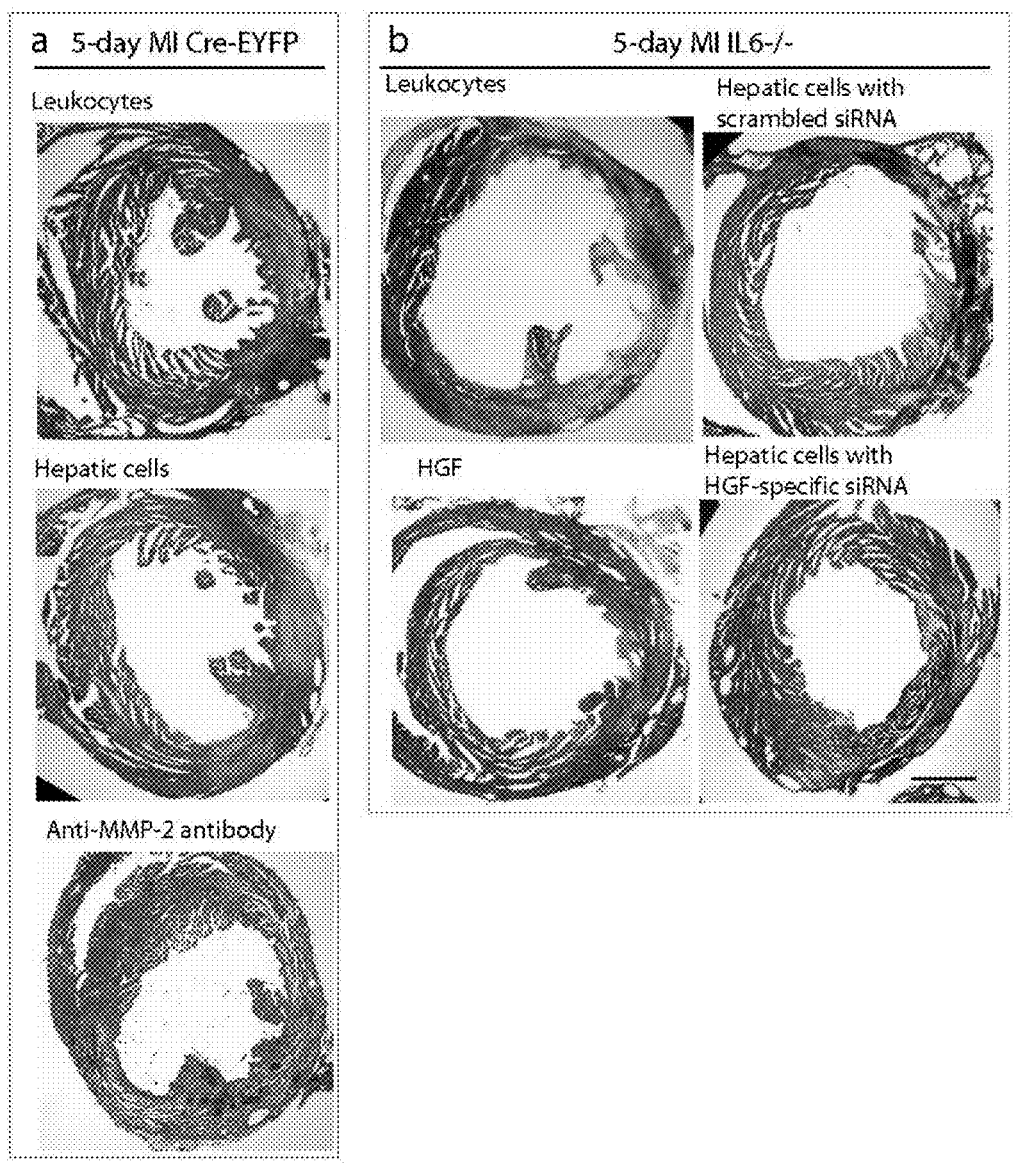
FIG. 10. Enhancement of myocardial survival in myocardial ischemia by hepatic cell transplantation. (a) Histological micrographs of AZAN-stained ischemic myocardium from Cre-EYFP mice with 5-day myocardial ischemia showing the influence of leukocyte or hepatic cell transplantation on the size of myocardial infarcts. The influence of anti-MMP-2 antibody administration is also presented. (b) AZAN-stained ischemic myocardium from IL-6−/− mice with 5-day myocardial ischemia showing the influence of leukocyte or hepatic cell transplantation on the size of myocardial infarcts. The hepatic cells were transfected with either scrambled or HGF-specific siRNA to demonstrate the role of HGF in supporting myocardial survival. The influence of HGF administration is also presented. For panels a and b, the scale bar is 1 mm. (c) Measured volume (vol) fraction of myocardial infarcts in Cre-EYFP mice with transplantation of leukocytes (gray bars) or hepatic cells (black bars) at day 5, 15, and 30. (d) Influence of hepatic cell transplantation, anti-MMP-2 antibody administration, or HGF administration on the volume fraction of myocardial infarcts in Cre-EYFP and IL-6−/− mice at day 5. HT: Hepatic cell transplantation. LT: Leukocyte transplantation. S: Scrambled. ab: Antibody. For panels c and d, means and standard deviations are presented (n=6). ***p<0.001.
Figure 10:
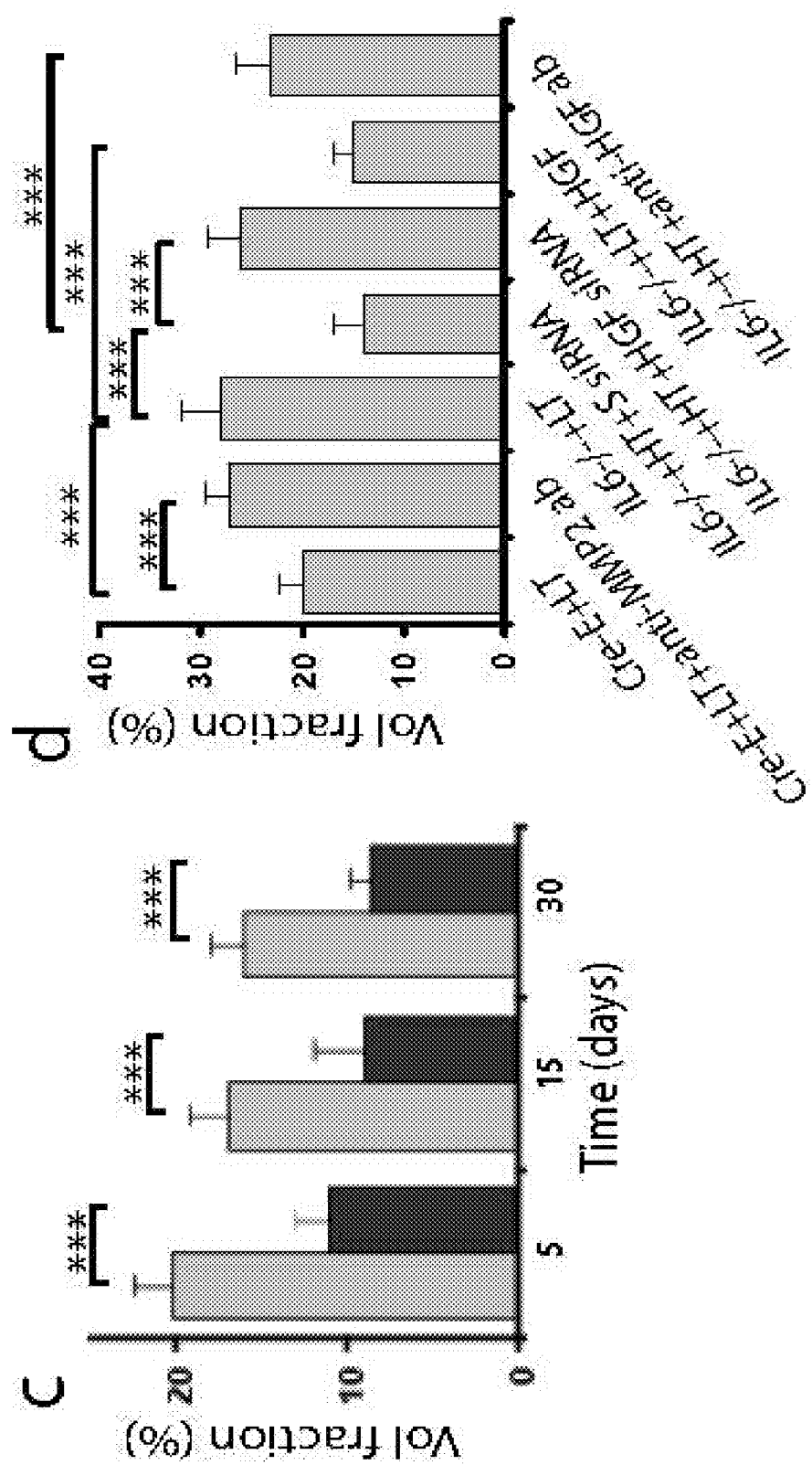

Hepatic cells (~$10^5$) derived from Cre-EYFP mice with 5-day myocardial ischemia were transplanted to Cre-EYFP mice via venous injection following coronary arterial ligation, when Cre-EYFP mice transplanted with allogenic leukocytes were used as controls, and tested myocardial death by the TUNEL assay[48,49] and the volume fraction of myocardial infarcts by the AZAN assay[50,51]. The transplantation of hepatic cells, which resulted in a significant increase in the population of EYFP-positive cells in the ischemic myocardium (FIGS. 6d, 6e, and 6h), induced a significant reduction in the population of TUNEL-positive myocardial nuclei (FIG. 9) and the volume fraction of myocardial infarcts compared to leukocyte transplantation (FIGS. 10a and 10c). It was further demonstrated that the population of TUNEL-positive myocardial nuclei (FIGS. 9c and 9g) and volume fraction of myocardial infarcts (FIGS. 10b and 10d) were significantly increased in IL-6$^{-/-}$ mice, which exhibited a significant reduction in hepatic cell mobilization and engraftment to the ischemic myocardium (FIGS. 3e and 3f), compared to that in Cre-EYFP mice (FIGS. 9 and 10). The most striking change in IL-6$^{-/-}$ mice was the increase in the rate of left ventricular rupture (27/34 or ~79% within 5 days) compared to that in Cre-EYFP mice (~14% within 5 days). Because of the high rate of left ventricular rupture, it was difficult to carry out observations beyond 5 days in IL-6$^{-/-}$ mice with myocardial ischemia. The transplantation of hepatic cells (~$10^5$ cells/mouse) from Cre-EYFP mice with 5-day myocardial ischemia to IL-6$^{-/-}$ mice with myocardial ischemia resulted in engraftment of EYFP-positive cells to the ischemic myocardium (FIGS. 3e and 3g), in association with a significant reduction in the population of TUNEL-positive myocardial nuclei (FIGS. 9c, 9d and 9h), volume fraction of myocardial infarcts (FIGS. 10b and 10d), and the rate of left ventricular rupture (4/11 or ~36% within 5 days). To further demonstrate the role of mobilized hepatic cells in supporting myocardial survival, an anti-MMP-2 antibody was delivered (100 ng/gm×2 per day) into the venous system of mice with myocardial ischemia, which resulted in a reduction in hepatic cell mobilization, and analyzed the influence of this modulation on the infarct volume fraction of the left ventricle. As shown in FIGS. 10a and 10d, administration of anti-MMP-2 antibody resulted in a significant increase in the infarct volume fraction. These observations suggest that hepatic cell mobilization and engraftment contribute to myocardial survival in experimental myocardial ischemia.

Figure 11:
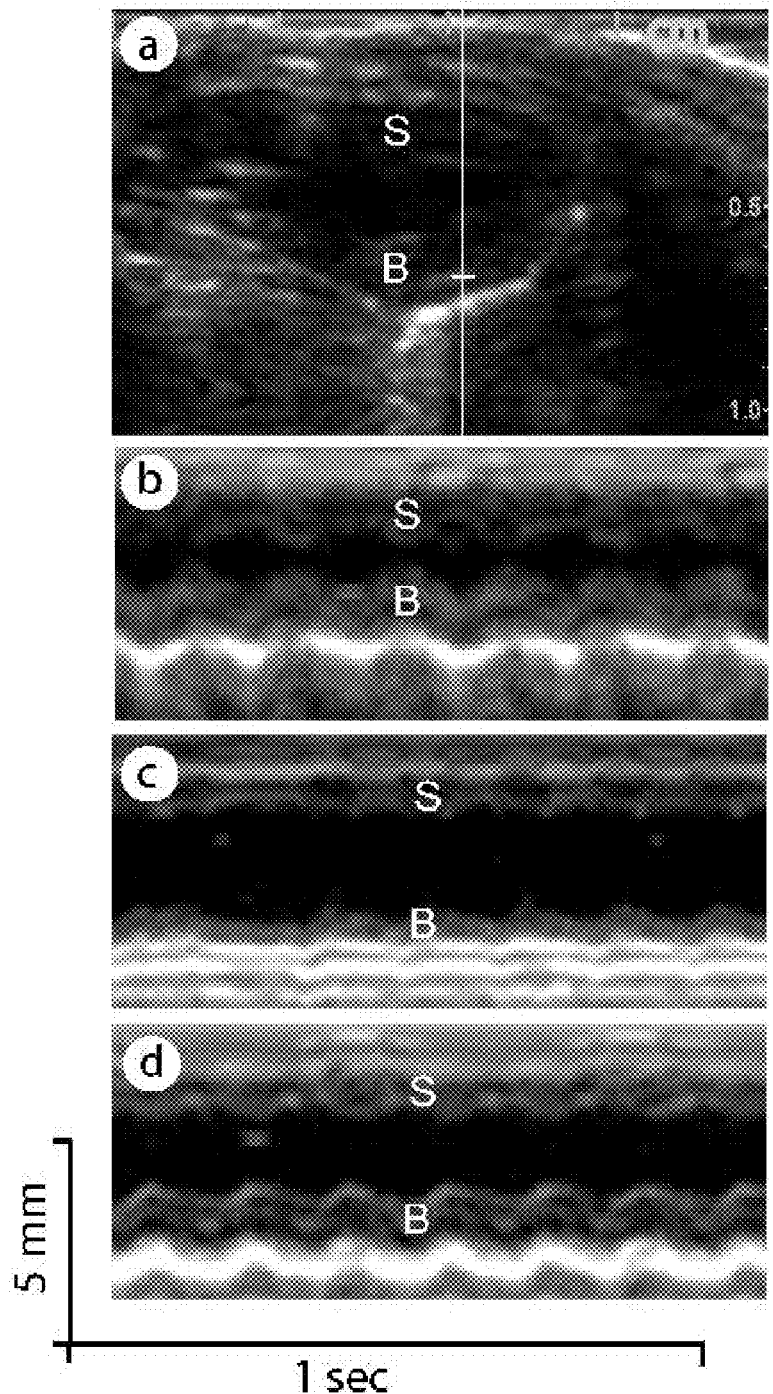
FIG. 11. Enhancement of left ventricular performance in myocardial ischemia by hepatic cell transplantation. (a) B-mode echocardiograph showing the left ventricle of a mouse. S, B: Ventricular septum and left ventricular back wall, respectively. (b-d) M-mode echocardiographs of the left ventricle of mice with sham operation (panel b) and myocardial ischemia with leukocyte transplantation (panel c) or hepatic cell transplantation (panel d) at day 5. (e-g) Fractional shortening (panel e), ejection fraction (panel f), and dp/dt (panel g) of the left ventricle measured from sham-operated (white bars) and ischemic Cre-EYFP mice with transplantation of leukocytes (gray bars) or hepatic cells (black bars) at day 5, 15, and 30. (h-j) Fractional shortening (panel h), ejection fraction (panel i), and dp/dt (panel j) of the left ventricle measured from sham-operated and ischemic IL-6−/− mice with transplantation of leukocytes or hepatic cells at day 5. The influence of HGF or anti-HGF antibody administration is also presented. For panel e-j, means and standard deviations are presented (n=6). p<0.01, and * p<0.001. MI: Myocardial ischemia. HT: Hepatic cell transplantation. LT: Leukocyte transplantation. S: Scrambled. ab: Anti-HGF antibody.
Figure 11:
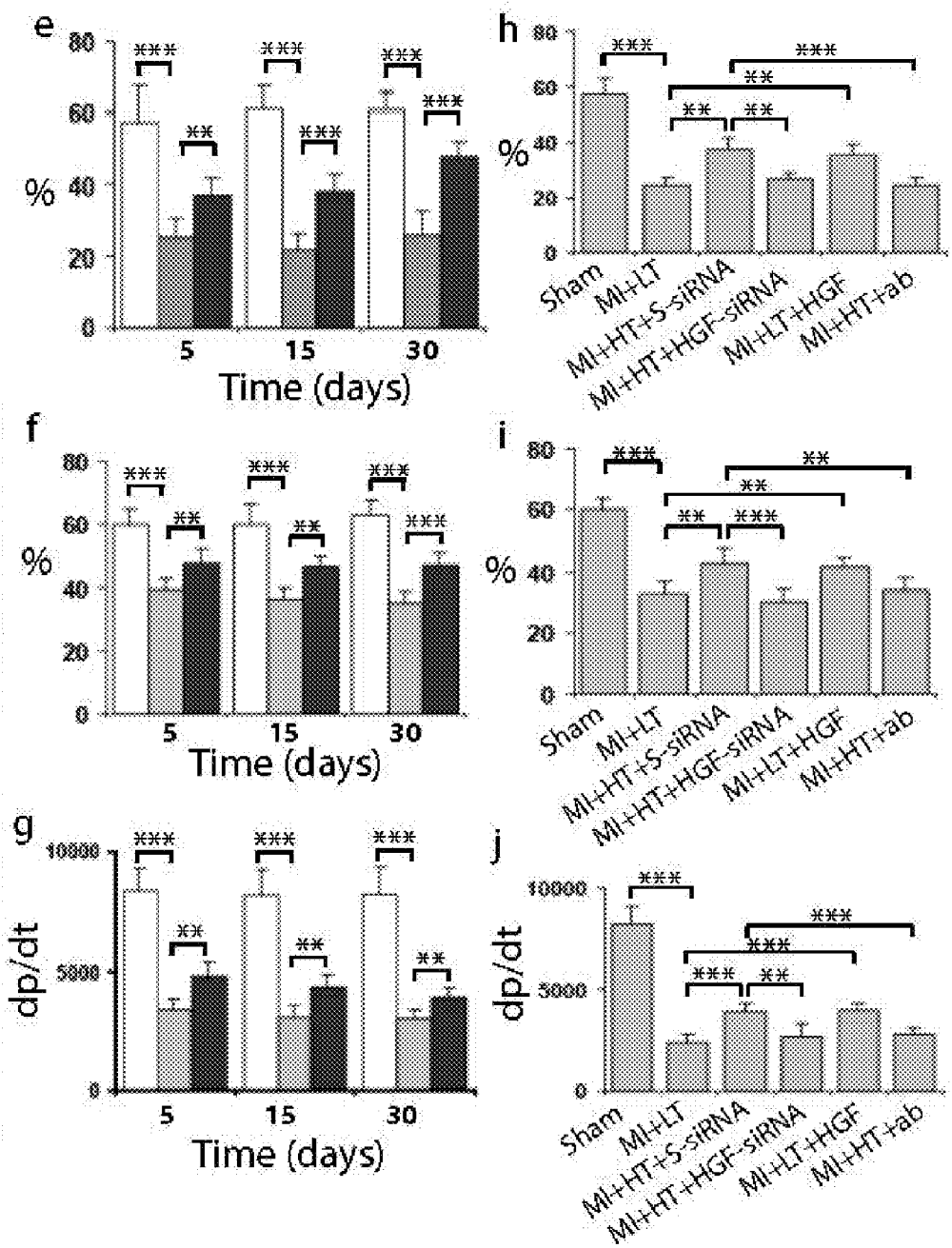

Hepatic Cell-Mediated Improvement of Left Ventricular Performance in Myocardial Ischemia To test whether hepatic cell engraftment to ischemic myocardium enhances myocardial function, hepatic cells (~$10^5$) derived from 5-day ischemic Cre-EYFP mice were transplanted to Cre-EYFP mice via venous injection and assessed the mechanical performance of the ischemic left ventricle. The fractional shortening and ejection fraction of the left ventricle as tested by M- and B-mode echocardiography (FIG. 11a-11f), respectively, reduced significantly in Cre-EYFP mice with myocardial ischemia compared to that in Cre-EYFP mice with sham operation at day 5, 15, and 30 (FIGS. 11B, 11C, 11e, and 11f). Furthermore, the left ventricular dp/dt reduced significantly in myocardial ischemia compared to that in sham controls (FIG. 11g). The transplantation of hepatic cells (~$10^5$) induced a significant improvement of the fractional shortening, ejection fraction, and dp/dt of the ischemic left ventricle compared to leukocyte transplantation (FIG. 11d-11g). In IL6$^{-/-}$ mice, the transplantation of hepatic cells (~$10^5$) induced a similar change in the left ventricular performance (FIG. 11h-11j). These observations suggest that the engraftment of hepatic cells to ischemic myocardium enhances myocardial performance.

Role of HGF in Mediating the Cardioprotective Effect of Hepatic Cells

Given the observations that hepatic cells derived from the liver exhibit HGF upregulation in myocardial ischemia (FIG. 7b) and HGF exerts cardioprotective effects[41-44], while the present invention is not limited to any particular mechanism, HGF upregulation may be one of the mechanisms by which mobilized hepatic cells support the survival and performance of ischemic myocardium. To test this mechanism, the population of TUNEL-positive myocardial nuclei, volume fraction of myocardial infarcts, and mechanical performance of the ischemic left ventricle in IL-6$^{-/-}$ mice with transplantation of HGF-siRNA- or scrambled siRNA-transfected hepatic cells was measured. The transplantation of scrambled siRNA-transfected hepatic cells resulted in a significant reduction in the population of TUNEL-positive myocardial nuclei (FIGS. 9c, 9d, and 9h) and volume fraction of myocardial infarcts (FIGS. 10b and 10d) in association with a significant increase in the mechanical performance of the ischemic left ventricle (FIG. 11h-11j) compared to leukocyte transplantation, whereas the transplantation of HGF-siRNA-transfected hepatic cells did not induce significant changes in these parameters (FIGS. 9c, 9e, 9h; 10b and 10d; 11h-11j). Anti-HGF antibody (100 ng/gm×2 per day) was also delivered via venous injection to ischemic IL-6$^{-/-}$ mice with hepatic cell transplantation (~$10^5$). This modulation significantly attenuated the cardioprotective effect of hepatic cell transplantation (FIGS. 9h; 10d; 11h-11j). Furthermore, administration of HGF (50 ng/gm×2 per day) to ischemic IL-6$^{-/-}$ mice via venous injection resulted in a significant reduction in the population of TUNEL-positive myocardial nuclei (FIGS. 9f and 9h) and volume fraction of myocardial infarcts (FIGS. 10b and 10d) in association with enhanced mechanical performance of the ischemic left ventricle (FIG. 11h-11j). These findings suggest that HGF upregulated in hepatic cells mediates at least partially the cardioprotective effect of hepatic cells in myocardial ischemia.

Discussion

Liver Response to Myocardial Ischemia

The liver has long been considered an organ responsible for metabolism, detoxification, bile secretion, and production of serum proteins. As a vital organ for controlling homeostasis, the liver has evolved with a unique self-protective function—complete mass regeneration in response to chemical-induced liver injury and partial hepatectomy. The liver contains a large reserve of hepatocytes and biliary epithelial cells, which are quiescent under physiological conditions. In response to liver injury, more than 90% of these cells can be activated to proliferate, resulting in rapid liver regeneration. In contrast to the liver, the adult heart lacks the function of complete regeneration in myocardial injury. As the heart supports the survival and function of the entire body system, it is conceivable that not only myocardial, but also non-myocardial mechanisms may be activated to minimize the impact of myocardial ischemia. This Example has shown that the liver is capable of assisting the heart in cardioprotection by mobilizing hepatic cells in experimental myocardial ischemia. Mobilized hepatic cells support the survival and performance of ischemic myocardium. When hepatic cell mobilization was impaired, as found in the mouse model of partial hepatectomy and IL-6 deficiency, myocardial injury was significantly intensified compared to control mice with a normal level of hepatic cell mobilization. While the present invention is not limited to any particular mechanism, and an understanding of the mechanism is not necessary to understand or practice the invention, it is believed that the mobilization of hepatic cells represents a non-myocardial mechanism for cardioprotection in myocardial ischemia.

The liver contains hematopoietic cells, including CD45+, CD11b+, and Sca-1+ cells as shown in previous studies and in this Example. Hematopoietic cells, such as bone marrow-derived stem cells and macrophages, have been shown to be capable of differentiating to hepatocyte-like cells. The hematopoietic cell-derived hepatic cells, along with liver-borne hematopoietic cells, may be mobilized in response to MMP-2 activation in myocardial ischemia. These cells may likely contribute to myocardial survival and performance. However, the population of the hematopoietic cell-derived hepatic cells is considerably small (about 0.0013%). In this Example, there was no finding of EYFP+ hepatic cells co-expressing hematopoietic markers, such as CD45, CD11b, or Sca-1, within the liver cell populations examined. This was due to the possibility that either the population of hematopoietic cell-derived hepatic cells was too small to be detected or the hematopoietic markers were no longer expressed in the liver cells derived from the hematopoietic stem cells. In this Example, the fraction of the hematopoietic cell-derived liver cells, if any, was considered part of the hepatic cell population.

Cardioprotective Role of Mobilized Hepatic Cells

Hepatic cells can be mobilized to the ischemic lesion of myocardium, suggesting that hepatic cells may contribute to cardioprotection. This Example established several strategies to test the cardioprotective role of mobilized hepatic cells: (1) increasing the population of circulating hepatic cells by transplantation of hepatic cells isolated from mice with 5-day myocardial ischemia; (2) reducing hepatic cell mobilization in myocardial ischemia by using the IL-6$^{-/-}$ mouse model, as IL-6 mediates hepatic cell mobilization, and stimulating hepatic cell mobilization by administration of IL-6 to IL-6$^{-/-}$ mice with myocardial ischemia; (3) reducing hepatic cell mobilization by administration of anti-MMP-2 antibody; and (4) reducing hepatic cell mobilization by partial hepatectomy (~60% removal of the liver mass).

The transplantation of hepatic cells resulted in an increase in the population of circulating hepatic cells. This modulation significantly improved the survival and performance of ischemic myocardium, especially, in IL-6$^{-/-}$ mice, which exhibited a significant reduction in hepatic cell mobilization. It should be noted that the hepatic cells used for transplantation were prepared from mice with 5-day myocardial ischemia, as these hepatic cells exhibited HGF upregulation. When recruited to the ischemic lesion of myocardium, hepatic cells were capable of expressing HGF, which contributed to cardioprotection.

Experiments involving the IL-6$^{-/-}$ mouse model demonstrated that IL-6 deficiency induced a significant reduction in hepatic cell mobilization in myocardial ischemia, which was associated with severe impairment of cardioprotection. The administration of IL-6 to IL-6$^{-/-}$ mice with myocardial ischemia stimulated hepatic cell mobilization, resulting in a significant improvement of myocardial survival.

Another experiment designed to demonstrate the cardioprotective role of hepatic cells was to reduce hepatic cell mobilization by administration of anti-MMP-2 antibody to mice with myocardial ischemia, as MMP-2 was shown to mediate hepatic cell mobilization. The administration of anti-MMP-2 antibody induced a significant reduction in hepatic cell mobilization, resulting in a significant increase in myocardial infarction.

The analyses presented above demonstrated that the experiments involving hepatic cell transplantation, IL-6 deficiency and restoration, and modulation of MMP-2 activities provided insightful information for assessing the cardioprotective role of hepatic cells. However, these experiments did not provide direct evidence that confirms the cardioprotective role of naturally mobilized hepatic cells. To resolve this issue, another experiment was carried out: myocardial ischemia with partial hepatectomy (~60% removal of the liver mass). Partial hepatectomy resulted in a significant reduction in the population of circulating hepatic cells as well as the density of hepatic cells recruited to the ischemic myocardium. As demonstrated in this Example, hepatic cell mobilization was primarily mediated by MMP-2 expressed in leukocytes. In myocardial ischemia with partial hepatectomy, the density of leukocytes retained in the liver parenchyma and the enzymatic activity of liver MMP-2 did not change significantly in the remaining liver compared with that in myocardial ischemia with sham liver operation, suggesting that the loss of liver mass was responsible for the attenuation of hepatic cell mobilization. This change resulted in a significant impairment of cardioprotection in myocardial ischemia as demonstrated by the TUNEL assay and the analysis of myocardial infarcts. Partial hepatectomy itself might unlikely influence the cardioprotective processes, as this procedure alone did not induce any myocardial injury and death (FIG. 10. Furthermore, transplantation of hepatic cells to mice with myocardial ischemia and partial hepatectomy significantly improved the survival of ischemic myocardium. These observations support the cardioprotective role of naturally mobilized hepatic cells in myocardial ischemia.

Hepatic Cell Mobilization

Hepatic cell mobilization is a regulated process in myocardial ischemia. While the present invention is not limited to any particular mechanism and an understanding of the mechanism is not necessary to practice the invention, it is believed that the following mechanism applies to the induction of hepatic cell mobilization. Myocardial ischemia induces IL-6 upregulation in the ischemic myocardium, resulting in an increase in the serum level of IL-6. IL-6 can stimulate leukocyte retention in the liver parenchyma and also induce leukocyte upregulation of MMP-2, a proteinase responsible for degradation of type IV and V collagen, gelatin, and elastin[35]. MMP-2 in turn mediates hepatic cell mobilization. When myocardial injury is healed, IL-6 expression decreases in association with a reduction in leukocyte retention and leukocyte expression of MMP-2. As a result, hepatic cell mobilization reduces accordingly.

IL-6 is a cytokine known to stimulate leukocyte adhesion to the endothelium, a process mediated by adhesion molecules. For instance, IL-6 can induce lymphocyte adhesion to endothelial cells via activating L-selectin in response to fever-range thermal stress. IL-6 can interact with the soluble form of the IL-6 receptor α subunit (sIL-6Ra). Upon interacting with IL-6, sIL-6Ra binds to the transmembrane receptor gp130. This activity results in activation of JAK-1, which induces tyrosine phosphorylation on the gp130 cytoplasmic domain. Selected phosphotyrosines on gp130 can thereby recruit SH2 domain-containing tyrosine phosphatase (SHP)-2, which can be phosphorylated by JAK-1. Phosphorylated SHP-2 can interact with the adaptor protein SOS/Grb-2, which in turn activates the MEK-ERK1/2 signaling pathway. Activated ERK1/2 induces activation of the transcriptional factors AP-1, CREB, and/or Egr-1, which trigger the expression of target genes responsible for regulating the activity of L-selectin, resulting in enhanced leukocyte adhesion to the endothelium.

Leukocytes express MMPs, including MMP-2. IL-6 has been shown to induce MMP-2 expression in leukocytes. The MEK-ERK1/2 signaling pathway plays a critical role in mediating IL-6-induced MMP expression. The IL-6Rα-gp130-SHP-2 signaling pathway described above is potentially responsible for activating the MEK-ERK1/2 signaling pathway. ERK1/2 can further activate the transcriptional factor AP-1, which acts on the AP-1 responsive site of the MMP-2 gene, inducing MMP-2 expression. IL-6 itself is expressed in activated leukocytes, inducing inflammatory processes such as leukocyte transmigration and fever. The physiological significance of MMP upregulation in response to IL-6 is to facilitate leukocyte transmigration to the site of injury and inflammation by degrading extracellular matrix. In myocardial ischemia, such inflammatory processes may be activated in the liver, resulting in hepatic cell mobilization.

Hepatic Cell-Mediated Cardioprotection

Hepatic cells can be mobilized to assist the heart in cardioprotection in ischemic injury. The present Example has demonstrated that HGF mediates the cardioprotective effect of hepatic cells in myocardial ischemia. HGF is a growth factor that promotes cardiomyocyte survival, alleviates myocardial fibrosis, and mobilizes resident cardiac stem cells to ischemic myocardium. As shown in this Example, this growth factor was upregulated in the hepatic cells of the liver in response to IL-6 stimulation in myocardial ischemia, a process associated with hepatic cell mobilization. While the present invention is not limited to any particular mechanism, and an understanding of the mechanism is not necessary to understand or practice the present invention, given the fact that HGF expression was significantly enhanced in the ischemic lesion of myocardium following hepatic cell transplantation and engraftment to the ischemic myocardium, it is believed that hepatic cell engraftment to the ischemic myocardium may contribute to HGF upregulation. This contribution was supported by the following observations. HGF was not significantly upregulated in the ischemic myocardium of IL-6$^{-/-}$ mice, which were associated with impaired hepatic cell mobilization. Transplantation of HGF-expressing hepatic cells derived from mice with myocardial ischemia to IL-6$^{-/-}$ mice induced significant HGF upregulation in the ischemic myocardium. In contrast, transplantation of hepatic cells with significantly reduced HGF expression by HGF-siRNA transfection to IL-6$^{-/-}$ mice did not induce significant HGF upregulation.

To demonstrate the role of HGF in mediating the cardioprotective effect of hepatic cells, HGF or anti-HGF antibody were administered to mice with myocardial ischemia. Administration of HGF significantly enhanced the survival and mechanical performance of ischemic myocardium, whereas administration of anti-HGF antibody, following transplantation of hepatic cells derived from mice with myocardial ischemia, significantly attenuated the cardioprotective effect of hepatic cells. These observations support the cardioprotective role of HGF in myocardial ischemia.

Example 2

Alleviation of Ischemic Myocardial Injury by Administration of Hepatic Cell-Derived Factors Myocardial ischemia induces cardiomyocyte injury and death, resulting in impairment of cardiac function. In spite of extensive investigations, few clinically effective agents have been developed for protecting myocardium from ischemic injury. Myocardial ischemia remains a leading cause of human death. As adult cardiomyocytes possess a limited capacity of self-protection and regeneration, mechanisms involving nonmyocytic cells are activated to support the survival and performance of cardiomyocytes. As described above, it has been determined that the liver can respond to myocardial ischemia to mobilize its cells to the circulatory system in a mouse model. While a fraction of mobilized hepatic cells engrafted to the lesion of ischemia, the remaining hepatic cells degraded within the circulatory system and released cell contents, which may also be used for effective cardioprotection in myocardial ischemia. As such, in certain embodiments, myocardial injury-alleviating therapies are based on factors derived from hepatic cells.

Hepatic cell-derived factors were prepared from allogenic liver specimens and used for alleviating ischemic myocardial injury in a mouse model. As myocardial ischemia stimulated hepatic cells to express cardioprotective factors, including hepatocyte growth factor (HGF), hepatic cell-derived factors were prepared from mice with 5-day myocardial ischemia preconditioning, while hepatic cell-derived factors from sham control mice were used as control agents. The choice of 5-day myocardial ischemia preconditioning was based on the observation that a peak expression level of HGF was found at this time. To prepare hepatic cell-derived factors, mice with or without myocardial ischemia preconditioning were anesthetized by intraperitoneal injection of ketamine (100 mg/kg) and xylazine (10 mg/kg). The portal vein of the liver was cannulated, perfused with phosphate buffered saline (PBS) for 5 min to remove residual blood, and then perfused with 0.25% collagenase type IV in PBS for 30 min at 37° C. to dissociate liver cells. Total liver cells were dispersed mechanically, and hepatic cells including hepatocytes and biliary epithelial cells were isolated by Percoll density gradient centrifugation. The isolated hepatic cells were washed in PBS for 3 times to remove residual collagenase and Percoll, subjected to 3 freezing-thawing cycles, and homogenized mechanically. The hepatic cell homogenates were centrifuged at 16,000 rpm for 20 min to remove cell organelles and debris. The supernatant, which contains hepatic cell-derived factors, was filtered through 0.2 µm filters and used for administration.

Figure 12:
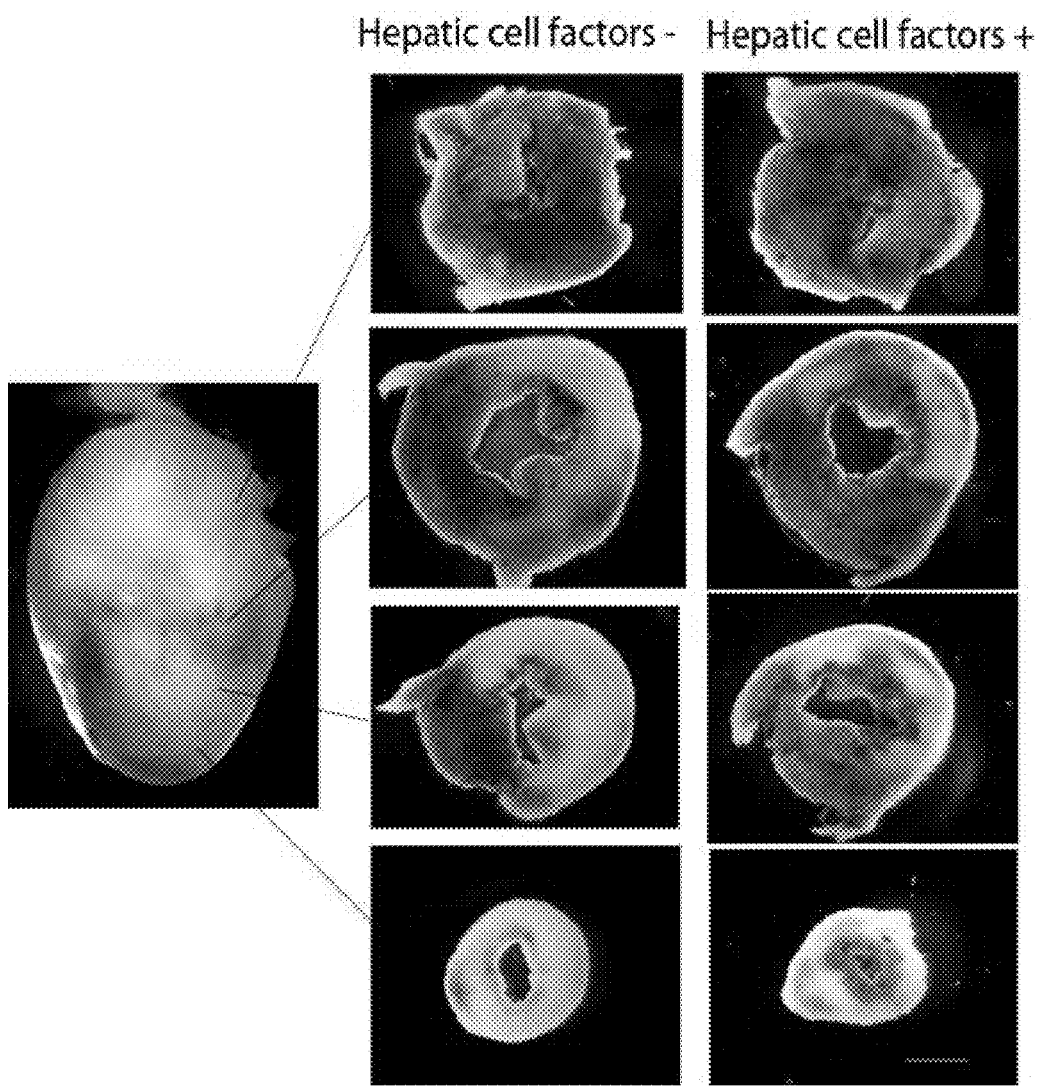
FIG. 12. Alleviation of myocardial infarction by administration of allogeneic hepatic cell-derived factors. The heart was freshly collected from mice with 24 hr-myocardial ischemia, cut into slices of approximately 1 mm in thickness, incubated with 1% TTC in PBS at 37° C. for 30 min, and fixed in 4% formaldehyde in PBS. The dark gray color represents intact myocardium, whereas the white/light gray color represents infarcted myocardium. Hepatic cell factors −: administration of leukocyte-derived factors only. Hepatic cell factors +: administration of hepatic cell-derived factors from mice with 5-day myocardial ischemia. Scale: 1 mm.
Figure 13:
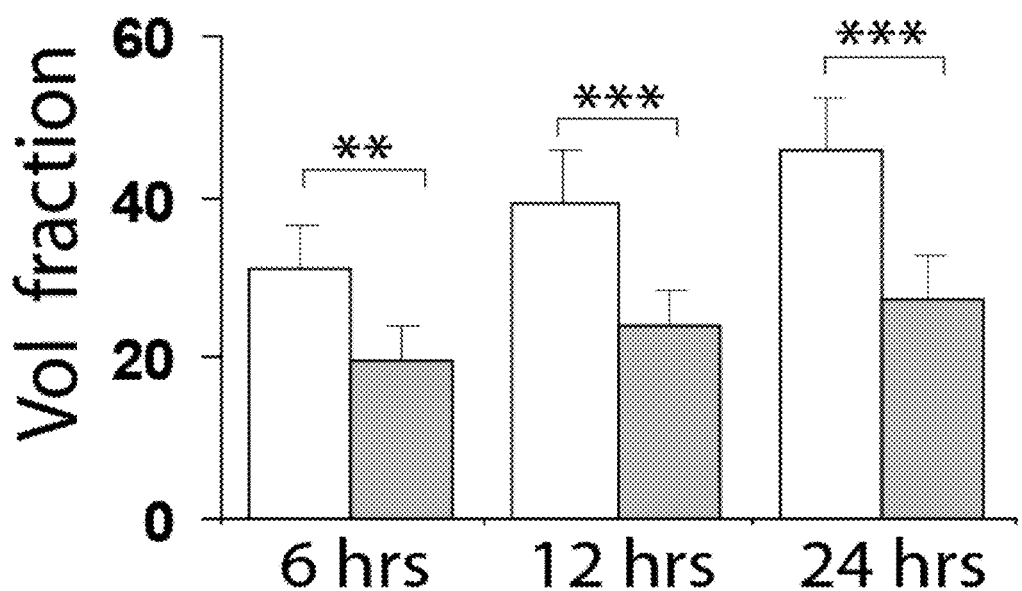
FIG. 13. Alleviation of myocardial infarction in response to administration of allogeneic hepatic cell-derived factors (from mice with 5-day myocardial ischemia) at 6, 12, and 24 hrs of myocardial ischemia. White bars: Volume (vol) fraction of myocardial infarcts in mice with administration of leukocyte-derived factors. Gray bars: Volume fraction of myocardial infarcts in mice with administration hepatic cell-derived factors. Means and SDs are presented (n=6). p<0.01, *p<0.001.

Myocardial ischemia in mice were induced by ligating the left anterior descending coronary artery for 30 min followed by reperfusion. Hepatic cell-derived factors from mice with 5-day myocardial ischemia (5 µg/gm body weight×2 per day, IV) were administered to mice with myocardial ischemia starting at 24 hrs before the induction of myocardial ischemia, while leukocyte-derived factors were used as control agents. Observations were carried out at 6, 12, and 24 hrs. Myocardial infarction was tested by the TTC assay. It was demonstrated that administration of allogeneic hepatic cell-derived factors to mice with myocardial ischemia significantly reduced myocardial infarction. As shown in FIGS. 12 and 13, the volume fraction of myocardial infarcts in mice with administration of hepatic cell-derived factors was significantly lower than that in mice with administration of leukocyte-derived factors at all observation times.

Figure 14:
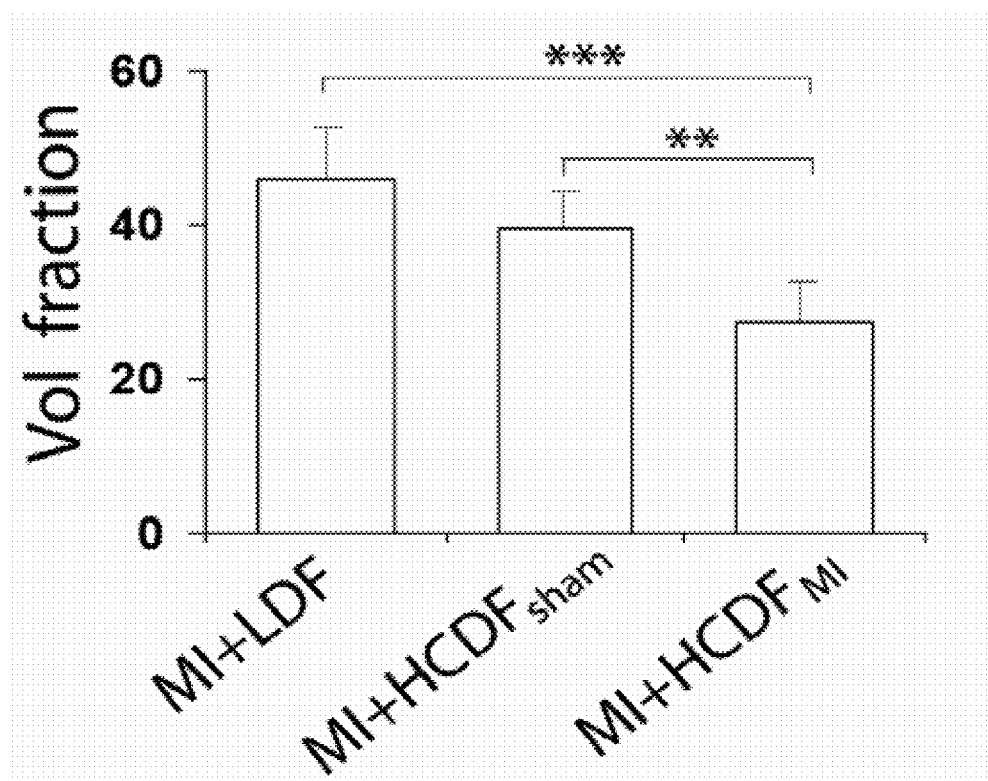
FIG. 14. Differential effects of hepatic cell-derived factors from mice with 5-day sham-operation and 5-day myocardial ischemia on the volume (vol) fraction of myocardial infarcts at 24 hrs. MI+LDF: myocardial ischemia with administration of leukocyte-derived factors. MI+HCDF$_{sham}$: myocardial ischemia with administration of hepatic cell-derived factors from mice with 5-day sham-operation. MI+HCDF$_{MI}$: myocardial ischemia with administration of hepatic cell-derived factors from mice with 5-day myocardial ischemia. Means and SDs are presented (n=6). p<0.01, *p<0.001.
Figure 15:
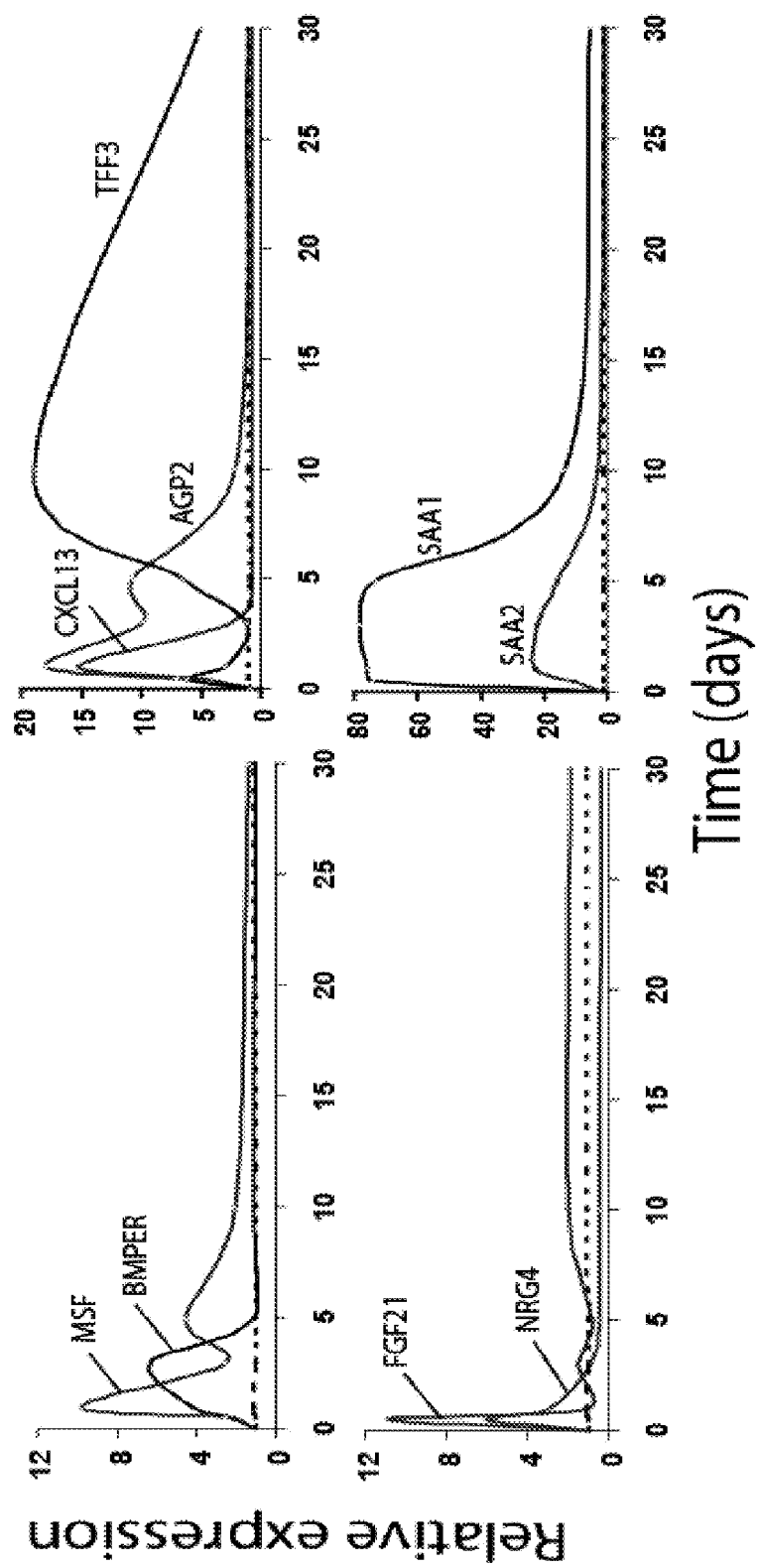
FIG. 15 shows the time-dependent expression of genes encoding hepatocyte-expressed proteins in mice with myocardial ischemia. Data at time zero were measured from sham control mice. "Relative expression" is defined as the ratio of gene expression in myocardial ischemia to that in sham controls. The beta actin gene was used as a control (dotted line).

To test whether myocardial ischemia preconditioning was important for generating hepatic cell-derived factors effective for alleviating myocardial injury, allogeneic hepatic cell-derived factors from mice with or without 5-day myocardial ischemia were administered to recipient mice with myocardial ischemia (5 µg/gm body weight×2 per day, IV). The degree of myocardial infarction was analyzed at 24 hrs of myocardial ischemia. As shown in FIG. 14, while administration of hepatic cell-derived factors without myocardial ischemia preconditioning resulted in a moderate reduction in myocardial infarction, administration of hepatic cell-derived factors with myocardial ischemia preconditioning induced a significant reduction in myocardial infarction. These observations suggested that administration of hepatic cell-derived factors alleviated myocardial injury, and myocardial ischemia preconditioning was important for generating effective hepatic cell-derived factors.

Example 3

Identification of Hepatocyte Secreted Factors

This example describes the identification of proteins secreted by hepatocytes to aid healing of ischemic injury.
Methods
Coronary arterial ligation and partial hepatectomy were performed as described in Example 1 using C57BL/6J mice.
Identification of Hepatocyte-Expressed Proteins Effective for Protection of Ischemic Myocardium Hepatocytes exhibited upregulation of numbers of secretory factors in response to myocardial ischemia. These proteins were screened for selecting factors beneficial to protection of ischemic myocardium. The mouse recombinant forms of the hepatocyte-expressed secretory proteins, including AGP2, BUMPER, FGF21, CXCL13, NRG4, PRG4, and TFF3, were administered individually to mice with acute myocardial ischemia for testing their role in protection of ischemic myocardium. Recombinant BUMPER and CXCL13 were obtained from R&D Systems, FGF21 was from Prospec, and AGP2, NRG4, PRG4, and TFF3 were from Abnova. For selecting cardioprotective factors, a recombinant protein was injected immediately following LAD coronary artery ligation at a dose of 50 ng/gm IV. Mouse serum albumin at the same dose was used as a control. At 6 hrs of myocardial ischemia, the mouse was euthanized and the heart was collected for TTC assay and measurement of the volume fraction of myocardial infarction (see below). A sample size of 6 was used for each recombinant protein and the albumin control. A factor was considered effective for protection of ischemic myocardium when its administration resulted in a significant reduction in the volume fraction of myocardial infarcts ($p<0.05$).

ELISA

ELISA was conducted to test the serum level of the hepatocyte-expressed secretory proteins effective for protection of ischemic myocardium. Serum was produced from blood samples collected from sham control and myocardial ischemic mice. Antibodies for the tested proteins and an HRP-conjugated secondary antibody were obtained from Santa Cruz. The Invitrogen Amplex ELISA development kit with the Ultrared reagent was used for the test based on the provider's instruction. The ELISA samples were measured using the BioTek Synergy4 plate reader. A relative serum level of each tested protein was calculated based on the serum level of the protein from control mice without surgical manipulation. Six tests were carried out for each protein at each observation time.

Determination of Doses for Administration of Hepatocyte-Expressed Proteins

One aim of this Example is to test whether administration of a combination of recombinant hepatocyte-expressed secretory proteins results in effective protection of ischemic myocardium, as these factors are naturally expressed in response to myocardial ischemia. Important issues examined are what is an effective dose range for each protein and what are the relative dose ratios between the administered proteins. The following strategy was used to determine the effective doses for the hepatocyte-expressed factors: (1) test the effect of a selected mouse recombinant hepatocyte-expressed protein most effective in protection of ischemic myocardium at various doses including 0, 12.5, 25, and 50 ng/gm with mouse serum albumin used as a control; (2) select the effective dose of this protein as a baseline for calculating the doses of other hepatocyte-upregulated proteins; (3) test the ratios of the maximal serum levels of the hepatocyte-expressed secretory proteins based on the ELISA results; and (4) combine all selected recombinant proteins based on the ratios of their maximal serum levels with the protein dose determined in step 2 as a baseline. A dose range of the combined recombinant proteins effective for protection of ischemic myocardium was determined by testing various doses (see below). The combination of the recombinant hepatocyte-expressed secretory proteins at a selected dose was injected into the femoral vein immediately following the ligation of the LAD coronary artery.

Measurement and Analysis of Myocardial Infarction

The degree of myocardial infarction was assessed based on the volume fraction of myocardial infarcts. The triphenyltetrazolium chloride (TTC) assay was used for staining and measuring the intact and infarcted myocardium at 6 and 24 hrs of myocardial ischemia. A fresh mouse heart was collected, frozen rapidly at −80 C, and cut into 1-mm thick slices using a blade with a 1-mm spacer. The cardiac slices were incubated in 1% TTC/PBS at 37 C for 30 min. All myocardial specimen slices below the coronary arterial ligation were measured for areas of the intact and infarcted myocardium. The total volumes of the intact and infarcted myocardium were calculated based on the measured area and section thickness. The volume fraction of myocardial infarcts was calculated with reference to the total volume of the left ventricular wall below the coronary arterial ligation and used to represent the degree of myocardial infarction.

For testing the degree of myocardial infarction at day 5, 10, and 30, the AZAN assay was conducted to stain and measure the intact and infarcted/fibrotic myocardium as described (Zou et al. 2003, Circulation, 108(6):748-53). The mouse heart was fixed by perfusion of 4% formaldehyde in PBS at a pressure of 120 mm Hg and cut into 50 um transverse serial cryo-sections. All specimen sections below the coronary arterial ligation were stained with the AZAN reagents, and used for measuring the areas of the intact and infarcted myocardium. The total volumes and the volume fraction of the intact and infarcted myocardium were measured and analyzed for evaluating the degree of myocardial infarction.

Measurement and Analysis of Left Ventricular dp/dt and −dp/dt

The left ventricular dp/dt and −dp/dt were measured and used to represent the myocardial contractile activity. A mouse was anesthetized as described above and a Millar catheter pressure transducer was inserted to the left ventricle via right carotid arterial catheterization. The left ventricular pressure, dp/dt, and −dp/dt were measured and recorded using a data acquisition system from sham control and myocardial ischemic mice.

Statistics

Means and standard deviations were calculated for each measured parameter. The two-tailed Student t-test was used for analyzing differences between two groups. ANOVA was used for multi-group difference analyses. A difference was considered statistically significant at $p<0.05$.

Results and Discussion

Figure 16:
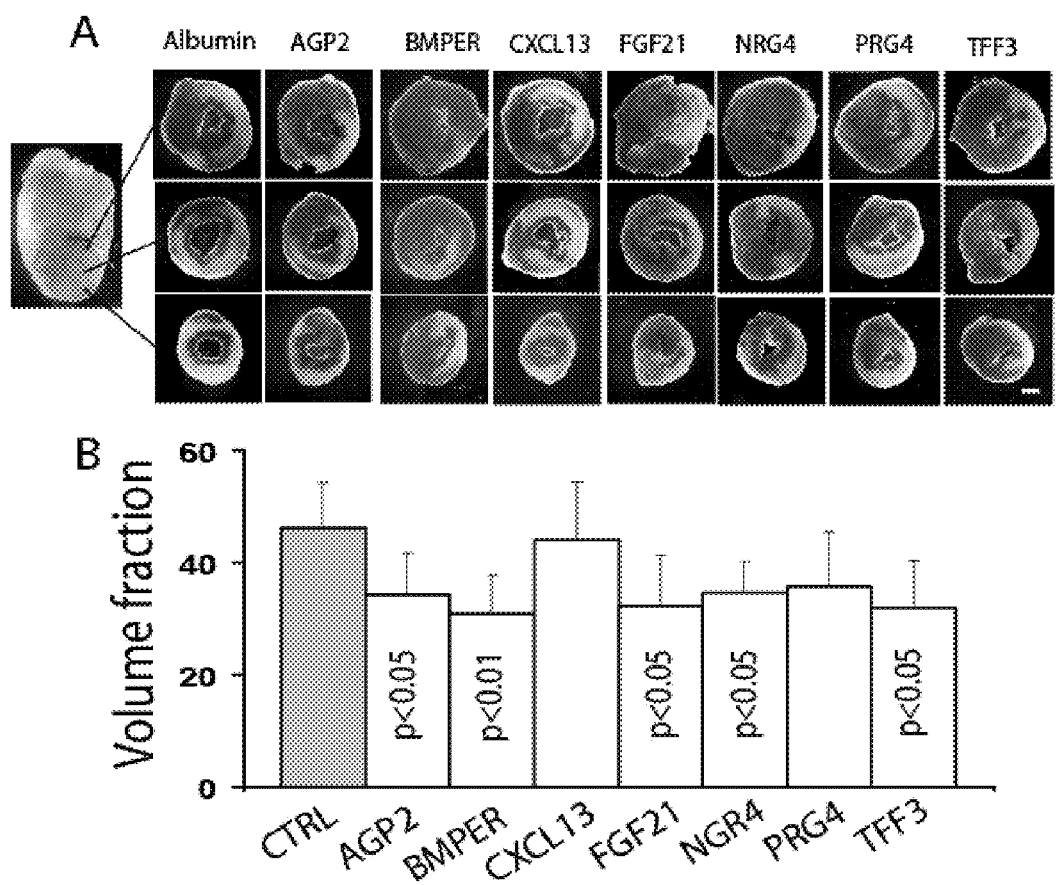
FIG. 16 shows screening hepatocyte secretory proteins for factors effective in protection of ischemic myocardium. (A) TTC (1%)-stained left ventricular specimens from myocardial ischemic mice administered with albumin, AGP2, BMPER, CXCL13, FGF21, NRG4, PRG4, and TFF3 (50 ng/gm, IV). Three slices were collected and presented from locations immediately below the LAD ligation, the middle between the LAD ligation and the apex, and near the apex of each mouse heart. TTC stains the intact myocardium red and the infarct white. Scale bar: mm. (B) Graphic representation of the influence of administration of albumin, AGP2, BMPER, CXCL13, FGF21, NRG4, PRG4, and TFF3 on the volume fraction of myocardial infarction. The p value on each bar is for comparison between the albumin control and a hepatocyte-expressed secretory factor. The volume fraction of myocardial infarcts was calculated with reference to the left ventricular wall volume below the LAD ligation. Means and SDs are presented. n=6 for each factor.

Hepatocyte-Expressed Secretory Factors Effective for Protection of Ischemic Myocardium Hepatocytes are capable of responding to myocardial ischemia and upregulating genes encoding secretory proteins, including AGP2, BUMPER, FGF21, CXCL13, NRG4, PRG4, and TFF3. These proteins were screened for identifying factors effective for protection of ischemic myocardium. This screening strategy was to administer the mouse recombinant form of each factor individually following the ligation of the LAD coronary artery at a dose of 50 ng/gm IV and to test the influence of the factor on the degree of myocardial infarction at 6 hrs of myocardial ischemia. A recombinant protein that causes a significant reduction in myocardial infarction ($p<0.05$), compared to controls with serum albumin administration, was considered a factor contributing to protection of ischemic myocardium. As shown in FIG. 16, for the seven tested proteins, administration of AGP2, BUMPER, FGF21, NRG4, or TFF3 resulted in a significant reduction in the volume fraction of myocardial infarction at 6 hrs as evaluated by the TTC assay. Thus, AGP2, BUMPER, FGF21, NRG4, and TFF3 were further tested for protein-level expression in hepatocytes, serum level, and time-dependent effect on protection of ischemic myocardium.

Figure 17:
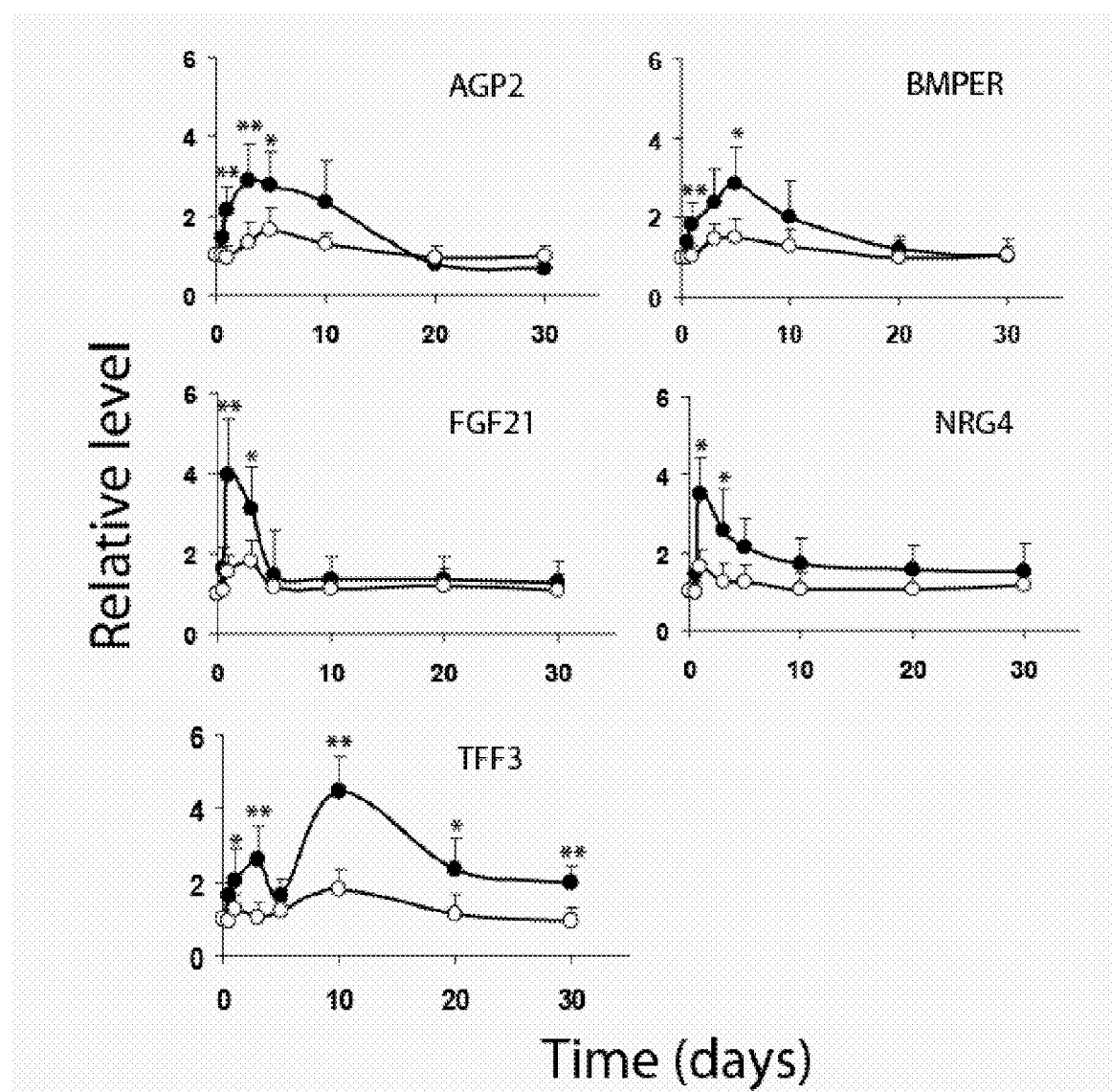
FIG. 17 shows serum levels of AGP2, BMPER, FGF21, NRG4, and TFF3 in sham control and myocardial ischemic mice by ELISA. Open circles: Sham controls. Closed circles: Myocardial ischemia. Means and SDs are presented. n=6 for each time point. *p<0.05 and **p<0.01 for comparison between sham control and myocardial ischemia at a selected time point.

Elevation in the Serum Level of Hepatocyte-Expressed Secretory Factors in Myocardial Ischemia As the secretory proteins AGP2, BUMPER, FGF21, NRG4, and TFF3 were upregulated in hepatocytes in response to myocardial ischemia, it was reasoned that these factors might be released to blood, contributing to protection of ischemic myocardium. The serum levels of these proteins were tested by ELISA at selected times following the ligation of the LAD coronary artery including 0.5, 1, 3, 5, 10, 20, and 30 days. As shown in FIG. 17, changes in the serum level of AGP2, BUMPER, FGF21, NRG4, and TFF3 followed different trends. The serum level of AGP2 and BMPER increased significantly at day 1, reached maximum at day 3 and 5, respectively, and returned to about the control baseline at day 20. FGF21 and NRG4 increased more rapidly and reached maximum at day 1, and returned toward the control level afterward. TFF3 increased significantly at day 1, reduced at day 3, increased again after day 3, reached maximum at day 10, and maintained a significantly higher level at day 20 and 30 compared to the sham controls. Changes in the serum level of these factors were consistent with their mRNA expression profile. These observations suggested that myocardial ischemia induced elevation in the serum level of AGP2, BUMPER, FGF21, NRG4, and TFF3. The sham operation also induced an elevation in the serum level of AGP2, BUMPER, FGF21, NRG4, and TFF3. However, these alterations were significantly lower than those in myocardial ischemia.

Doses for Administration of Hepatocyte-Expressed Factors

To determine an effective dose range for protection of ischemic myocardium by AGP2, BUMPER, FGF21, NRG4, and TFF3, dose tests were conducted (0, 12.5, 25, and 50 ng/gm) for the mouse recombinant form of BMPER, as this factor was most effective in protection of ischemic myocardium (FIG. 16). The minimal dose of BMPER effective for protection of ischemic myocardium was determined by comparisons between various doses and the albumin control. This dose was used as a baseline for selecting doses for other hepatocyte-expressed factors based on the ratios of the maximal serum levels of these factors tested by ELISA. The combination of all selected factors based on these ratios was used for further tests.

Figure 18:
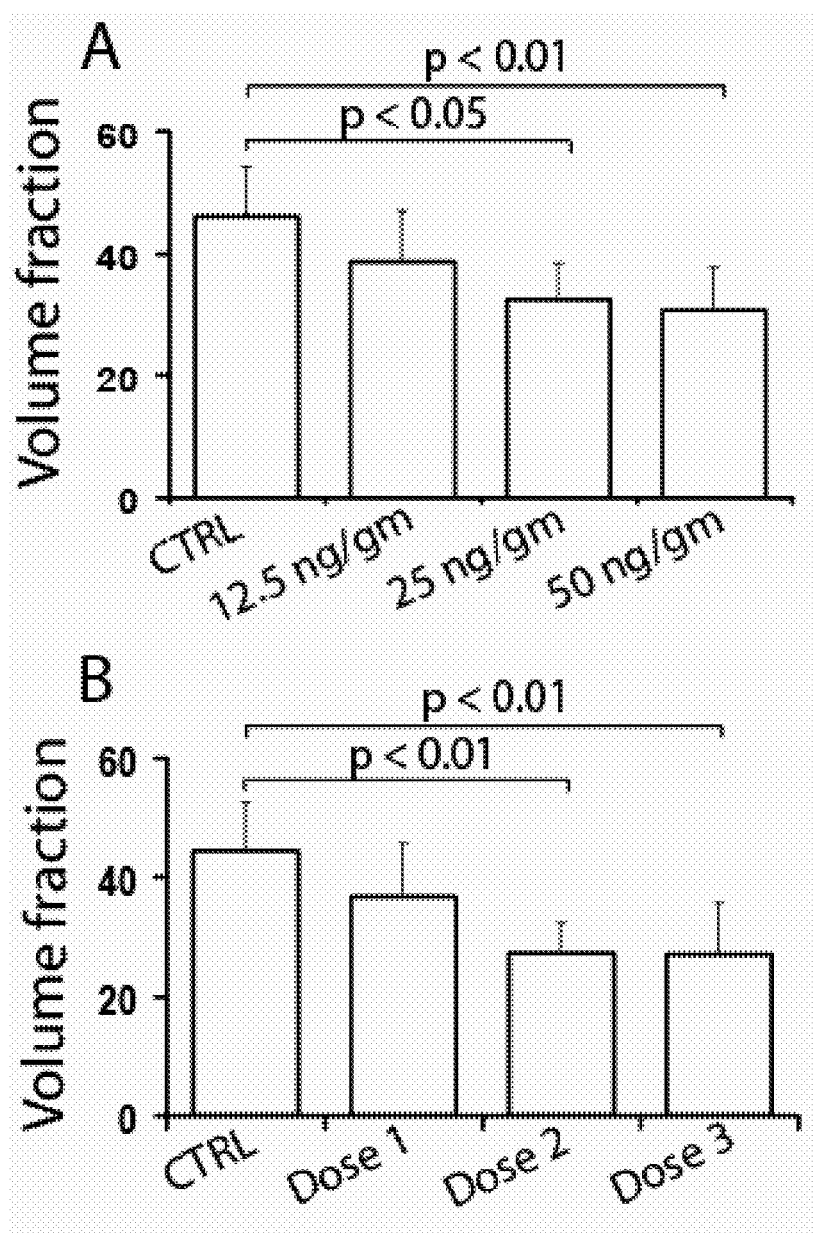
FIG. 18 shows dose-dependent effects of BMPER and the combination of AGP2, BMPER, FGF21, NRG4, and TFF3 on the volume fraction of myocardial infarcts (%). (A) Influence of BMPER administration on myocardial infarction at 3 doses: 12.5, 25, and 50 ng/gm. CTRL: Albumin control. (B) Influence of combined AGP2, BMPER, FGF21, NRG4, and TFF3 on myocardial infarction at 3 dose combinations: (1) 12.5, 12.5, 17.25, 15.4, 19.4 ng/gm; (2) 25, 25, 34.5, 30.8, 38.8 ng/gm; and (3) 50, 50, 69, 61.6, and 77.6 ng/gm for AGP2, BMPER, FGF21, NRG4, and TFF3, respectively. Means and SDs are presented. n=6 for each dose.

As shown in FIG. 18A, among the doses for recombinant BMPER, administration at the dose 25 ng/gm resulted in a significant reduction in myocardial infarction. An increase to 50 ng/gm BMPER did not induce further significant reduction in myocardial infarction. Thus, the dose 25 ng/gm BMPER was selected as the baseline for selecting doses for other hepatocyte-expressed secretory factors. ELISA tests demonstrated that the ratios of the maximal AGP2, BUMPER, FGF21, NRG4, and TFF3 serum levels were 1:1:1.38:1.23:1.55, giving a dose combination of 25, 25, 34.5, 30.8, 38.8 ng/gm for the 5 factors, respectively. To assess whether this combination dose was adequate for administration, three combination doses were tested based on the ratios of the maximal AGP2, BUMPER, FGF21, NRG4, and TFF3 serum levels: 12.5, 12.5, 17.25, 15.4, 19.4 ng/gm (dose 1); 25, 25, 34.5, 30.8, 38.8 ng/gm (dose 2); and 50, 50, 69, 61.6, and 77.6 ng/gm, respectively (dose 3). As shown in FIG. 18B, administration of dose 2 resulted in a significant reduction in myocardial infarction compared to albumin controls at 6 hrs following the ligation of the LAD coronary artery. Such a treatment resulted in a higher level of alleviation of myocardial infarction compared to BMPER administration at the dose level 25 ng/gm, although the difference was not statistically significant. Administration of dose 3 did not lead to a further significant reduction in myocardial ischemia. These observations indicate that the combination dose 25, 25, 34.5, 30.8, 38.8 ng/gm for AGP2, BUMPER, FGF21, NRG4, and TFF3, respectively, was adequate for administration of hepatocyte-expressed secretory factors.

Figure 19:
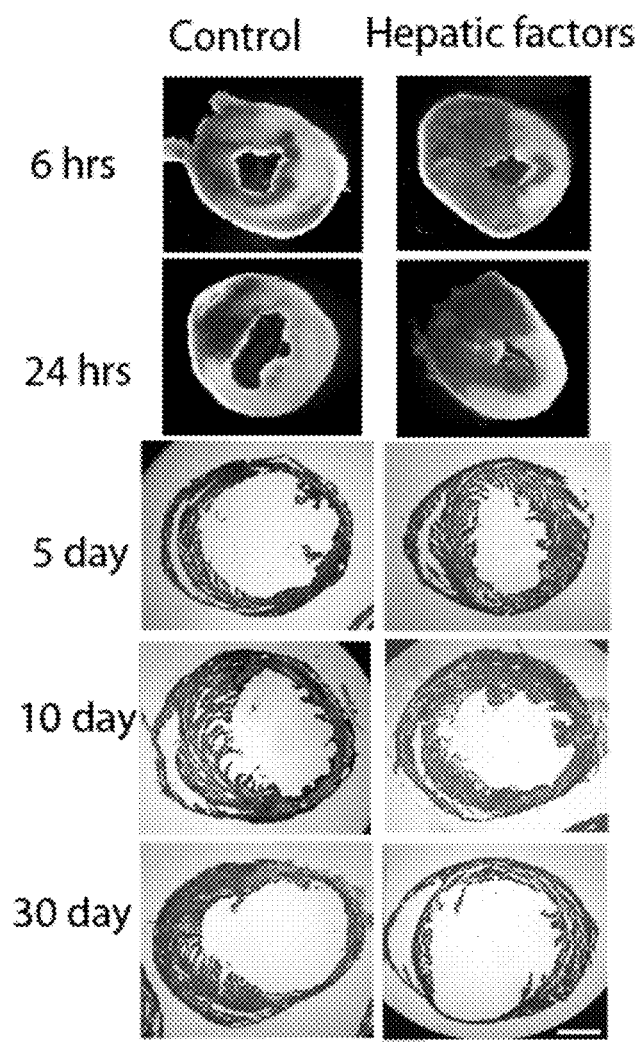
FIG. 19 shows alleviation of myocardial infarction in response to administration of combined AGP2, BMPER, FGF21, NRG4, and TFF3. Control: Administration of albumin. 6 and 24 hrs: TTC staining 5, 10, and 30 days: AZAN staining Scale bar: 1 mm. For the bar graph, the open bars are for albumin controls and the closed bars are for administration of combined AGP2, BMPER, FGF21, NRG4, and TFF3. Means and SDs are presented. n=6 for each time point.
Figure 19:
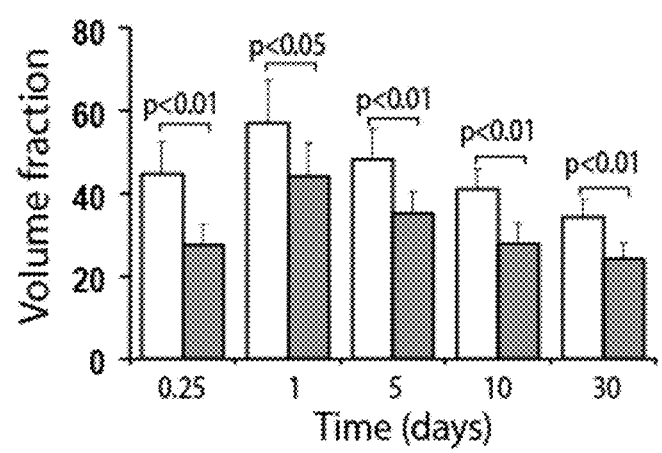

Influence of Hepatocyte-Expressed Secretory Factors on Myocardial Infarction and Contractile Activities To test time-dependent protective effects of the combination of AGP2, BUMPER, FGF21, NRG4, and TFF3, these factors were administered (25, 25, 34.5, 30.8, 38.8 ng/gm, respectively, IV) immediately following the ligation of the LAD coronary artery twice per day for a maximum of 3 days and the volume fraction of myocardial infarcts at 0.25, 1, 5, 10, and 30 days was tested (1 and 2 injections for 0.25 and 1 day observations, respectively). As shown in FIG. 19, administration of these factors resulted in significant alleviation of myocardial infarction at all observation times, while the alleviation levels differed between the observation times. These observations indicate that hepatocyte-expressed secretory factors may be used for protection of ischemic myocardium. Note that the volume fraction of myocardial infarcts reached the highest level at day 1 and reduced gradually afterward. This reduction was due to fibrosis-induced shrinkage of infarcted myocardium.

Figure 20:
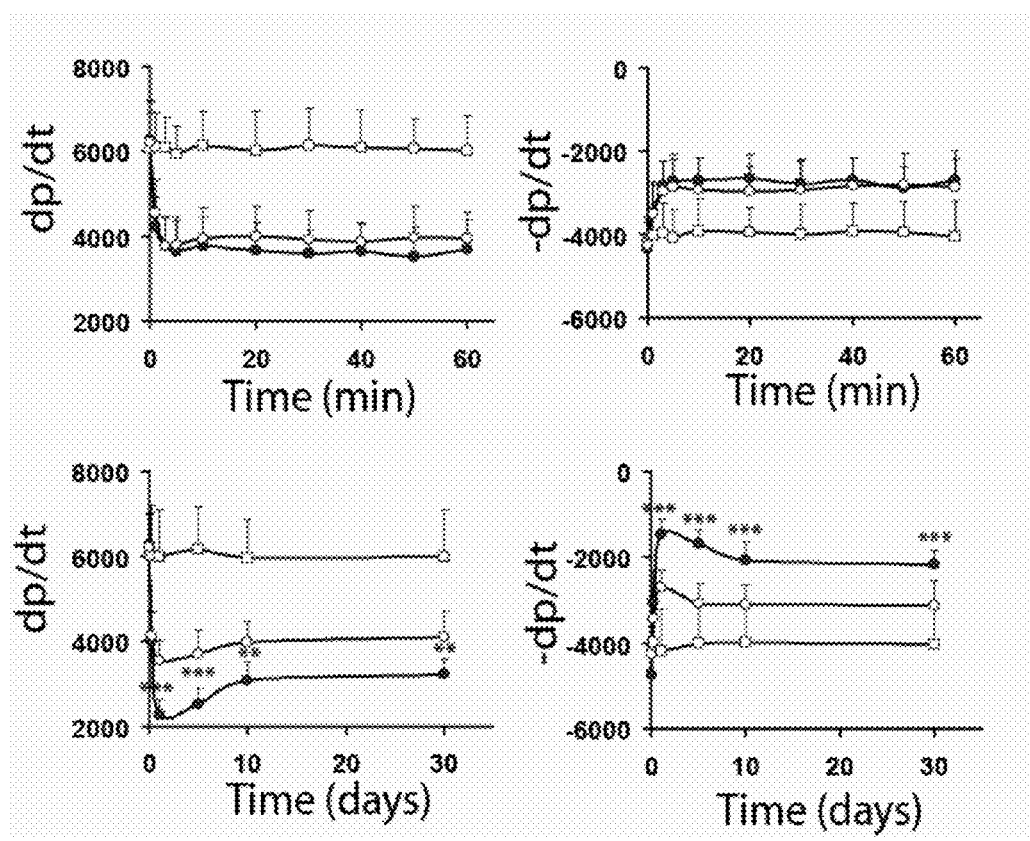
FIG. 20 shows improvement of left ventricular dp/dt and −dp/dt in response to administration of combined AGP2, BMPER, FGF21, NRG4, and TFF3 in myocardial ischemia. The two upper panels represent continuous dp/dt and −dp/dt measurements during the early 60 min following the ligation of the LAD coronary artery. The lower panels represent dp/dt and −dp/dt measurements at day 0.25, 1, 5, 10, and 30. Open squares: Sham controls. Closed circles: Myocardial ischemia with albumin administration. Open circles: Myocardial ischemia with administration of combined AGP2, BMPER, FGF21, NRG4, and TFF3. Means and SDs are presented. p<0.01 and *p<0.001 for comparison between groups with albumin and the 5 hepatocyte-expressed secretory factors at each time point. n=6 for each time point.

The influence of AGP2, BUMPER, FGF21, NRG4, and TFF3 was further tested on the left ventricular dp/dt and −dp/dt during the first 60 min and at 0.25, 1, 5, 10, and 30 days. As shown in FIG. 20, during the early 60 min, the left ventricular dp/dt and −dp/dt reduced rapidly at 1 min following the ligation of the LAD coronary artery. Administration of the 5 combined hepatocyte-expressed factors did not significantly influence the left ventricular dp/dt and −dp/dt during the early hour. The left ventricular dp/dt and −dp/dt dropped further at 0.25 and 1 day, and slightly increased afterward, but did not returned to the sham control level at day 30. Administration of the 5 combined hepatocyte-expressed factors (25, 25, 34.5, 30.8, 38.8 ng/gm, respectively) resulted in a significant elevation in the absolute value of the left ventricular dp/dt and −dp/dt at day 1, 5, 10, and 30. These observation suggest that the hepatocyte-expressed secretory factors should be useful for improving the contractile function of ischemic myocardium.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

I claim:

1. A method of treating a subject having myocardial ischemia comprising: administering a composition to a subject having myocardial ischemia such that myocardial injury in said subject is reduced, wherein said composition comprises at least one factor selected from the group consisting of:
   i) α-1-acid glycoprotein 2 (AGP2) or a biologically active fragment thereof;
   ii) bone morphogenetic protein binding endothelial regulatory (BMPER) or a biologically active fragment thereof and
   iii) trefoil factor 3 (TFF3) or a biologically active fragment thereof.

2. The method of claim 1, wherein said at least one factor is α-1-acid glycoprotein 2 (AGP2) or a biologically active fragment thereof.

3. The method of claim 1, wherein said at least one factor is administered at a dosage of 5 µg/kg-75 µg/kg.

4. The method of claim 1, wherein said at least one factor is administered at a dosage of 15 µg/kg-50 µg/kg.

5. The method of claim 4, wherein said BMPER is administered at a dosage of 15 µg/kg-35 µg/kg.

6. The method of claim 1, wherein said at least one factor comprises at least two of said factors.

7. The method of claim 1, wherein said at least one factor is bone morphogenetic protein binding endothelial regulator (BMPER) or a biologically active fragment thereof.

8. The method of claim 1, wherein said at least one factor comprises trefoil factor 3 (TFF3) or a biologically active fragment thereof.

9. The method of claim 1, wherein said administration is performed intravenously.

10. A method of treating a human subject having myocardial ischemia comprising: administering a composition to a human subject having myocardial ischemia such that myocardial injury in said subject is reduced, wherein said composition comprises at least one factor selected from the group consisting of:
   i) α-1-acid glycoprotein 2 (AGP2) as shown in SEQ ID NO: 11, or a biologically active variant or biologically active fragment of SEQ ID NO:11 that has one or two amino acid changes from the corresponding sequence in SEQ ID NO:11;
   ii) bone morphogenetic protein binding endothelial regulatory (BMPER) as shown in SEQ ID NO:13, or a biologically active variant or biologically active fragment of SEQ ID NO:13 that has one or two amino acid changes from the corresponding sequence in SEQ ID NO:13; and
   iii) trefoil factor 3 (TFF3) as shown in SEQ ID NO:25, or a biologically active variant or biologically active fragment of SEQ ID NO:25 that has one or two amino acid changes from the corresponding sequence in SEQ ID NO:25.

11. The method of claim 10, wherein said at least one factor comprises a biologically active variant of SEQ ID NO:11 that has one or two amino acid changes from the corresponding sequence in SEQ ID NO:11.

12. The method of claim 10, wherein said at least one factor comprises a biologically active variant of SEQ ID NO:13 that has one or two amino acid changes from the corresponding sequence in SEQ ID NO:13.

13. The method of claim 10, wherein said at least one factor comprises a biologically active variant of SEQ ID NO:25 that has one or two amino acid changes from the corresponding sequence in SEQ ID NO:25.

* * * * *

UNITED STATES PATENT AND TRADEMARK OFFICE
CERTIFICATE OF CORRECTION

| | | |
|---|---|---|
| PATENT NO. | : 8,889,625 B2 | Page 1 of 1 |
| APPLICATION NO. | : 12/833534 | |
| DATED | : November 18, 2014 | |
| INVENTOR(S) | : Shu Q. Liu | |

It is certified that error appears in the above-identified patent and that said Letters Patent is hereby corrected as shown below:

In the Claims

Column 59, lines 31 to 33, should read:

ii) bone morphogenetic protein binding endothelial regulatory (BMPER) or a biologically active fragment thereof; and Signed and Sealed this Seventeenth Day of February, 2015

Michelle K. Lee
*Deputy Director of the United States Patent and Trademark Office*

SEQUENCE LISTING

<160> NUMBER OF SEQ ID NOS: 27

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
acctgaagat gttcgcgatt atct                                            24

```
<210> SEQ ID NO 2
<211> LENGTH: 23
<212> TYPE: DNA
<213> ORGANISM: Artificial Sequence
<220> FEATURE:
<223> OTHER INFORMATION: Synthetic

<400> SEQUENCE: 2
accgtcagta cgtgagatat ctt                                              23

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
gtcagtggag agggtgaagg                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
tacataacct tcgggcatgg                                                  20

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
ttccatccag ttgccttctt gg                                               22

<210> SEQ ID NO 6
<211> LENGTH: 23
<212> TYPE: DNA
<213> ORGANISM: Artificial Sequence
<220> FEATURE:
<223> OTHER INFORMATION: Synthetic

<400> SEQUENCE: 6
ttctcatttc cacgatttcc cag                                              23

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
cacaccaggt gaaggatgtg                                                  20

<210> SEQ ID NO 8
<211> LENGTH: 20
<212> TYPE: DNA
<213> ORGANISM: Artificial Sequence
<220> FEATURE:
<223> OTHER INFORMATION: Synthetic
```

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 8
gttgaaggaa acgagcgaag                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
acccagaaga ctgtggatgg                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ccctgttgct gtagccgtat                                              20

<210> SEQ ID NO 11
<211> LENGTH: 201
<212> TYPE: PRT
<213> ORGANISM: Homo sapiens

<400> SEQUENCE: 11

Met Ala Leu Ser Trp Val Leu Thr Val Leu Ser Leu Leu Pro Leu Leu
1               5                   10                  15

Glu Ala Gln Ile Pro Leu Cys Ala Asn Leu Val Pro Val Pro Ile Thr
            20                  25                  30

Asn Ala Thr Leu Asp Arg Ile Thr Gly Lys Trp Phe Tyr Ile Ala Ser
        35                  40                  45

Ala Phe Arg Asn Glu Glu Tyr Asn Lys Ser Val Gln Glu Ile Gln Ala
    50                  55                  60

Thr Phe Phe Tyr Phe Thr Pro Asn Lys Thr Glu Asp Thr Ile Phe Leu
65                  70                  75                  80

Arg Glu Tyr Gln Thr Arg Gln Asn Gln Cys Phe Tyr Asn Ser Ser Tyr
                85                  90                  95

Leu Asn Val Gln Arg Glu Asn Gly Thr Val Ser Arg Tyr Glu Gly Gly
            100                 105                 110

Arg Glu His Val Ala His Leu Leu Phe Leu Arg Asp Thr Lys Thr Leu
        115                 120                 125

Met Phe Gly Ser Tyr Leu Asp Asp Glu Lys Asn Trp Gly Leu Ser Phe
    130                 135                 140

Tyr Ala Asp Lys Pro Glu Thr Thr Lys Glu Gln Leu Gly Glu Phe Tyr
145                 150                 155                 160

Glu Ala Leu Asp Cys Leu Cys Ile Pro Arg Ser Asp Val Met Tyr Thr
                165                 170                 175

Asp Trp Lys Lys Asp Lys Cys Glu Pro Leu Glu Lys Gln His Glu Lys
            180                 185                 190

Glu Arg Lys Gln Glu Glu Gly Glu Ser
        195                 200

<210> SEQ ID NO 12
<211> LENGTH: 606

<212> TYPE: DNA
<213> ORGANISM: Homo sapiens

<400> SEQUENCE: 12

```
atggcgctgt cctgggttct tacagtcctg agcctcctac ctctgctgga agcccagatc    60
ccattgtgtg ccaacctagt accggtgccc atcaccaacg ccaccctgga ccggatcact   120
ggcaagtggt tttatatcgc atcggccttt cgaaacgagg agtacaataa gtcggttcag   180
gagatccaag caaccttctt ttactttacc cccaacaaga cagaggacac gatctttctc   240
agagagtacc agacccgcca gaaccagtgc ttctataact ccagttacct gaatgtccag   300
cgggagaatg ggaccgtctc cagatacgag ggaggccgag aacatgttgc tcacctgctg   360
ttccttaggg acaccaagac cttgatgttt ggttcctacc tggacgatga aagaactgg   420
gggctgtctt tctatgctga caagccagag acgaccaagg agcaactggg agagttctac   480
gaagctctcg actgcttgtg cattcccagg tcagatgtca tgtacaccga ctggaaaaag   540
gataagtgtg agccactgga gaagcagcac gagaaggaga ggaaacagga ggaggggaa   600
tcctag                                                              606
```

<210> SEQ ID NO 13
<211> LENGTH: 685
<212> TYPE: PRT
<213> ORGANISM: Homo sapiens

<400> SEQUENCE: 13

```
Met Leu Trp Phe Ser Gly Val Gly Ala Leu Ala Glu Arg Tyr Cys Arg
1               5                   10                  15

Arg Ser Pro Gly Ile Thr Cys Cys Val Leu Leu Leu Asn Cys Ser
            20                  25                  30

Gly Val Pro Met Ser Leu Ala Ser Ser Phe Leu Thr Gly Ser Val Ala
        35                  40                  45

Lys Cys Glu Asn Glu Gly Glu Val Leu Gln Ile Pro Phe Ile Thr Asp
    50                  55                  60

Asn Pro Cys Ile Met Cys Val Cys Leu Asn Lys Glu Val Thr Cys Lys
65                  70                  75                  80

Arg Glu Lys Cys Pro Val Leu Ser Arg Asp Cys Ala Leu Ala Ile Lys
                85                  90                  95

Gln Arg Gly Ala Cys Cys Glu Gln Cys Lys Gly Cys Thr Tyr Glu Gly
            100                 105                 110

Asn Thr Tyr Asn Ser Ser Phe Lys Trp Gln Ser Pro Ala Glu Pro Cys
        115                 120                 125

Val Leu Arg Gln Cys Gln Glu Gly Val Val Thr Glu Ser Gly Val Arg
    130                 135                 140

Cys Val Val His Cys Lys Asn Pro Leu Glu His Leu Gly Met Cys Cys
145                 150                 155                 160

Pro Thr Cys Pro Gly Cys Val Phe Glu Gly Val Gln Tyr Gln Glu Gly
                165                 170                 175

Glu Glu Phe Gln Pro Glu Gly Ser Lys Cys Thr Lys Cys Ser Cys Thr
            180                 185                 190

Gly Gly Arg Thr Gln Cys Val Arg Glu Val Cys Pro Ile Leu Ser Cys
        195                 200                 205

Pro Gln His Leu Ser His Ile Pro Gly Cys Cys Pro Lys Cys
    210                 215                 220

Leu Gly Gln Arg Lys Val Phe Asp Leu Pro Phe Gly Ser Cys Leu Phe
225                 230                 235                 240
```

```
Arg Ser Asp Val Tyr Asp Asn Gly Ser Ser Phe Leu Tyr Asp Asn Cys
            245                 250                 255

Thr Ala Cys Thr Cys Arg Asp Ser Thr Val Val Cys Lys Arg Lys Cys
            260                 265                 270

Ser His Pro Gly Gly Cys Asp Gln Gly Gln Glu Gly Cys Cys Glu Glu
            275                 280                 285

Cys Leu Leu Arg Val Pro Pro Glu Asp Ile Lys Val Cys Lys Phe Gly
        290                 295                 300

Asn Lys Ile Phe Gln Asp Gly Glu Met Trp Ser Ser Ile Asn Cys Thr
305                 310                 315                 320

Ile Cys Ala Cys Val Lys Gly Arg Thr Glu Cys Arg Asn Lys Gln Cys
                325                 330                 335

Ile Pro Ile Ser Ser Cys Pro Gln Gly Lys Ile Leu Asn Arg Lys Gly
            340                 345                 350

Cys Cys Pro Ile Cys Thr Glu Lys Pro Gly Val Cys Thr Val Phe Gly
            355                 360                 365

Asp Pro His Tyr Asn Thr Phe Asp Gly Arg Thr Phe Asn Phe Gln Gly
        370                 375                 380

Thr Cys Gln Tyr Val Leu Thr Lys Asp Cys Ser Ser Pro Ala Ser Pro
385                 390                 395                 400

Phe Gln Val Leu Val Lys Asn Asp Ala Arg Arg Thr Arg Ser Phe Ser
                405                 410                 415

Trp Thr Lys Ser Val Glu Leu Val Leu Gly Glu Ser Arg Val Ser Leu
            420                 425                 430

Gln Gln His Leu Thr Val Arg Trp Asn Gly Ser Arg Ile Ala Leu Pro
        435                 440                 445

Cys Arg Ala Pro His Phe His Ile Asp Leu Asp Gly Tyr Leu Leu Lys
    450                 455                 460

Val Thr Thr Lys Ala Gly Leu Glu Ile Ser Trp Asp Gly Asp Ser Phe
465                 470                 475                 480

Val Glu Val Met Ala Ala Pro His Leu Lys Gly Lys Leu Cys Gly Leu
                485                 490                 495

Cys Gly Asn Tyr Asn Gly His Lys Arg Asp Asp Leu Ile Gly Gly Asp
            500                 505                 510

Gly Asn Phe Lys Phe Asp Val Asp Asp Phe Ala Glu Ser Trp Arg Val
        515                 520                 525

Glu Ser Asn Glu Phe Cys Asn Arg Pro Gln Arg Lys Pro Val Pro Glu
530                 535                 540

Leu Cys Gln Gly Thr Val Lys Val Lys Leu Arg Ala His Arg Glu Cys
545                 550                 555                 560

Gln Lys Leu Lys Ser Trp Glu Phe Gln Thr Cys His Ser Thr Val Asp
                565                 570                 575

Tyr Ala Thr Phe Tyr Arg Ser Cys Val Thr Asp Met Cys Glu Cys Pro
            580                 585                 590

Val His Lys Asn Cys Tyr Cys Glu Ser Phe Leu Ala Tyr Thr Arg Ala
        595                 600                 605

Cys Gln Arg Glu Gly Ile Lys Val His Trp Glu Pro Gln Gln Asn Cys
    610                 615                 620

Ala Ala Thr Gln Cys Lys His Gly Ala Val Tyr Asp Thr Cys Gly Pro
625                 630                 635                 640

Gly Cys Ile Lys Thr Cys Asp Asn Trp Asn Glu Ile Gly Pro Cys Asn
                645                 650                 655
```

Lys Pro Cys Val Ala Gly Cys His Cys Pro Ala Asn Leu Val Leu His
        660                 665                 670

Lys Gly Arg Cys Ile Lys Pro Val Leu Cys Pro Gln Arg
        675                 680                 685

<210> SEQ ID NO 14
<211> LENGTH: 2058
<212> TYPE: DNA
<213> ORGANISM: Homo sapiens

<400> SEQUENCE: 14

| | | | | | |
|---|---|---|---|---|---|
| atgctctggt | tctccggcgt | cggggctctg | gctgagcgtt | actgccgccg | ctcgcctggg | 60 |
| attacgtgct | gcgtcttgct | gctactcaat | tgctcggggg | tccccatgtc | tctggcttcc | 120 |
| tccttcttga | caggttctgt | tgcaaaatgt | gaaaatgaag | gtgaagtcct | ccagattcca | 180 |
| tttatcacag | acaacccttg | cataatgtgt | gtctgcttga | caaggaagt | gacatgtaag | 240 |
| agagagaagt | gccccgtgct | gtcccgagac | tgtgccctgg | ccatcaagca | gaggggagcc | 300 |
| tgttgtgaac | agtgcaaagg | ttgcacctat | gaaggaaata | cctataacag | ctccttcaaa | 360 |
| tggcagagcc | cggctgagcc | ttgtgttcta | cgccagtgcc | aggagggcgt | tgtcacagag | 420 |
| tctggggtgc | gctgtgttgt | tcattgtaaa | acccctttgg | agcatctggg | aatgtgctgc | 480 |
| cccacatgtc | caggctgtgt | gtttgagggt | gtgcagtatc | aagaaggga | ggaatttcag | 540 |
| ccagaaggaa | gcaaatgtac | caagtgttcc | tgcactggag | caggacaca | atgtgtgaga | 600 |
| gaagtctgtc | ccattctctc | ctgtccccag | caccttagtc | acataccccc | aggacagtgc | 660 |
| tgccccaaat | gtttgggtca | gaggaaagtg | tttgacctcc | cttttgggag | ctgcctcttt | 720 |
| cgaagtgatg | tttatgacaa | tggatcctca | tttctgtacg | ataactgcac | agcttgtacc | 780 |
| tgcagggact | ctactgtggt | ttgcaagagg | aagtgctccc | accctggtgg | ctgtgaccaa | 840 |
| ggccaggagg | ctgttgtga | agagtgcctc | ctacgagtgc | ccccagaaga | catcaaagta | 900 |
| tgcaaatttg | caacaagat | tttccaggat | ggagagatgt | ggtcctctat | caattgtacc | 960 |
| atctgtgctt | gtgtgaaagg | caggacggag | tgtcgcaata | gcagtgcat | tcccatcagt | 1020 |
| agctgcccac | agggcaaaat | tctcaacaga | aaaggatgct | gtcctatttg | cactgaaaag | 1080 |
| cccggcgttt | gcacggtgtt | tggagatccc | cactacaaca | cttttgacgg | tcggacattt | 1140 |
| aactttcagg | ggacgtgtca | gtacgttttg | acaaaagact | gctcctcccc | tgcctcgccc | 1200 |
| ttccaggtgc | tggtgaagaa | cgacgcccgc | cggacacgct | ccttctcgtg | gaccaagtcg | 1260 |
| gtggagctgg | tgctgggcga | gagcagggtc | agcctgcagc | agcacctcac | cgtgcgctgg | 1320 |
| aacggctcgc | gcatcgcgct | cccctgccgc | gcgccacact | tccacatcga | cctggatggc | 1380 |
| tacctcttga | agtgaccac | caaagcaggt | ttggaaatat | cttgggatgg | agacagtttt | 1440 |
| gtagaagtca | tggctgcgcc | gcatctcaag | ggcaagctct | gtggtctttg | tggcaactac | 1500 |
| aatggacata | aacgtgatga | cttaattggt | ggagatggaa | acttcaagtt | tgatgtggat | 1560 |
| gactttgctg | aatcttggag | ggtggagtcc | aatgagttct | gcaacagacc | tcagagaaag | 1620 |
| ccagtgcctg | aactgtgtca | agggacagtc | aaggtaaagc | tccgggccca | tcgagaatgc | 1680 |
| caaaagctca | aatcctggga | gtttcagacc | tgccactcga | ctgtggacta | cgccactttc | 1740 |
| taccggtcct | gtgtgacaga | catgtgtgaa | tgtccagtcc | ataaaaactg | ttattgcgag | 1800 |
| tcatttttgg | catatacccg | ggcctgccag | agagagggca | tcaaagtcca | ctgggagcct | 1860 |
| cagcagaatt | gtgcagccac | ccagtgtaag | catggtgctg | tgtacgatac | ctgtggtccg | 1920 |
| ggatgtatca | agacgtgtga | caactggaat | gaaattggtc | catgcaacaa | gccgtgcgtt | 1980 |

```
gctgggtgcc actgtccagc aaacttggtc cttcacaagg gaaggtgcat caagccagtc    2040
ctttgtcccc agcggtga                                                  2058
```

<210> SEQ ID NO 15
<211> LENGTH: 209
<212> TYPE: PRT
<213> ORGANISM: Homo sapiens

<400> SEQUENCE: 15

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 16
<211> LENGTH: 940
<212> TYPE: DNA
<213> ORGANISM: Homo sapiens

<400> SEQUENCE: 16

```
ctgtcagctg aggatccagc cgaaagagga gccaggcact caggccacct gagtctactc      60
acctggacaa ctggaatctg caccaattc taaaccactc agcttctccg agctcacacc      120
ccggagatca cctgaggacc cgagccattg atggactcgg acgagaccgg gttcgagcac     180
tcaggactgt gggtttctgt gctggctggt cttctgctgg gagcctgcca ggcacacccc     240
atccctgact ccagtcctct cctgcaattc ggggggccaag tccggcagcg gtacctctac    300
acagatgatg cccagcagac agaagcccac ctggagatca gggaggatgg gacggtgggg     360
ggcgctgctg accagagccc cgaaagtctc ctgcagctga aagccttgaa gccgggagtt     420
attcaaatct gggagtcaa gacatccagg ttcctgtgcc agcggccaga tggggccctg     480
tatggatcgc tccactttga ccctgaggcc tgcagcttcc gggagctgct tcttgaggac     540
```

```
ggatacaatg tttaccagtc cgaagcccac ggcctcccgc tgcacctgcc agggaacaag    600
tccccacacc gggaccctgc accccgagga ccagctcgct tcctgccact accaggcctg    660 cccccgcac tcccggagcc acccggaatc ctggcccccc agcccccga tgtgggctcc      720 tcggaccctc tgagcatggt gggaccttcc cagggccgaa gccccagcta cgcttcctga    780
agccagaggc tgtttactat gacatctcct ctttatttat taggttattt atcttattta    840 ttttttatt tttcttactt gagataataa agagttccag aggagaaaaa aaaaaaaaa      900 aaaaaaaaa aaaaaaaaa aaaaaaaaa aaaaaaaa                               940
```

```
<210> SEQ ID NO 17
<211> LENGTH: 115
<212> TYPE: PRT
<213> ORGANISM: Homo sapiens

<400> SEQUENCE: 17

Met Pro Thr Asp His Glu Glu Pro Cys Gly Pro Ser His Lys Ser Phe
1               5                   10                  15

Cys Leu Asn Gly Gly Leu Cys Tyr Val Ile Pro Thr Ile Pro Ser Pro
            20                  25                  30

Phe Cys Arg Cys Val Glu Asn Tyr Thr Gly Ala Arg Cys Glu Glu Val
        35                  40                  45

Phe Leu Pro Gly Ser Ser Ile Gln Thr Lys Ser Asn Leu Phe Glu Ala
    50                  55                  60

Phe Val Ala Leu Ala Val Leu Val Thr Leu Ile Ile Gly Ala Phe Tyr
65                  70                  75                  80

Phe Leu Cys Arg Lys Gly His Phe Gln Arg Ala Ser Ser Val Gln Tyr
                85                  90                  95

Asp Ile Asn Leu Val Glu Thr Ser Ser Thr Ser Ala His His Ser His
            100                 105                 110

Glu Gln His
        115
```

```
<210> SEQ ID NO 18
<211> LENGTH: 348
<212> TYPE: DNA
<213> ORGANISM: Homo sapiens

<400> SEQUENCE: 18
atgccaacag atcacgaaga gccctgtggt cccagtcaca gtcgttttg cctgaatggg      60 gggctttgtt atgtgatacc tactattccc agcccatttt gtaggtgcgt tgaaaactat    120
acaggagctc gttgtgaaga ggttttctc ccaggctcca gcatccaaac taaaagtaac     180
ctgtttgaag cttttgtggc attggcggtc ctagtaacac ttatcattgg agccttctac    240
ttcctttgca ggaaaggcca ctttcagaga gccagttcag tccagtatga tatcaacctg    300
gtagagacga gcagtaccag tgcccaccac agtcatgaac aacactga                 348
```

```
<210> SEQ ID NO 19
<211> LENGTH: 35
<212> TYPE: PRT
<213> ORGANISM: Homo sapiens

<400> SEQUENCE: 19

Met Pro Thr Asp His Glu Glu Pro Cys Gly Pro Ser His Lys Ser Phe
1               5                   10                  15

Cys Leu Asn Gly Gly Leu Cys Tyr Val Ile Pro Thr Ile Pro Ser Pro
```

```
                    20                  25                  30

Phe Cys Gly
        35

<210> SEQ ID NO 20
<211> LENGTH: 138
<212> TYPE: DNA
<213> ORGANISM: Homo sapiens

<400> SEQUENCE: 20
atgccaacag atcacgaaga gccctgtggt cccagtcaca agtcgttttg cctgaatggg      60
gggctttgtt atgtgatacc tactattccc agcccatttt gtggttaatg aggaactgat     120
taatgaggga accaatag                                                    138

<210> SEQ ID NO 21
<211> LENGTH: 56
<212> TYPE: PRT
<213> ORGANISM: Homo sapiens

<400> SEQUENCE: 21

Met Pro Thr Asp His Glu Glu Pro Cys Gly Leu Ser His Lys Ser Phe
1               5                   10                  15

Cys Leu Asn Gly Gly Leu Cys Tyr Val Ile Pro Thr Ile Pro Ser Pro
                20                  25                  30

Phe Cys Ser Leu His Glu Asn Glu Asn Asp Asn Asn Glu Asp Leu Tyr
            35                  40                  45

Asp Asp Leu Leu Pro Leu Asn Glu
    50                  55

<210> SEQ ID NO 22
<211> LENGTH: 174
<212> TYPE: DNA
<213> ORGANISM: Homo sapiens

<400> SEQUENCE: 22
atgccaacag atcacgaaga gccctgtggt ctcagtcaca agtcgttttg cctgaatggg      60
gggctttgtt atgtgatacc tactattccc agcccatttt gtagtctaca cgaaaatgaa     120
aacgacaaca atgaagacct ttatgatgat ctacttccac ttaatgaata gtaa            174

<210> SEQ ID NO 23
<211> LENGTH: 90
<212> TYPE: PRT
<213> ORGANISM: Homo sapiens

<400> SEQUENCE: 23

Met Pro Thr Asp His Glu Glu Pro Cys Gly Pro Ser His Lys Ser Phe
1               5                   10                  15

Cys Leu Asn Gly Gly Leu Cys Tyr Val Ile Pro Thr Ile Pro Ser Pro
                20                  25                  30

Phe Cys Arg Cys Val Glu Asn Tyr Thr Gly Ala Arg Cys Glu Glu Val
            35                  40                  45

Phe Leu Pro Gly Ser Ser Ile Gln Thr Lys Ser Asn Leu Phe Glu Ala
    50                  55                  60

Phe Val Ala Leu Ala Val Leu Val Thr Leu Ile Ile Gly Ala Phe Tyr
65                  70                  75                  80

Phe Leu Cys Arg Cys Gly Asn Thr Cys Met
                85                  90
```

<210> SEQ ID NO 24
<211> LENGTH: 273
<212> TYPE: DNA
<213> ORGANISM: Homo sapiens

<400> SEQUENCE: 24

```
atgccaacag atcacgaaga gccctgtggt cccagtcaca agtcgttttg cctgaatggg    60
gggctttgtt atgtgatacc tactattccc agcccatttt gtaggtgcgt tgaaaactat   120
acaggagctc gttgtgaaga ggttttttctc ccaggctcca gcatccaaac taaaagtaac   180
ctgtttgaag cttttgtggc attggcggtc ctagtaacac ttatcattgg agccttctac   240
ttcctttgca ggtgtggtaa cacatgcatg tag                                 273
```

<210> SEQ ID NO 25
<211> LENGTH: 73
<212> TYPE: PRT
<213> ORGANISM: Homo sapiens

<400> SEQUENCE: 25

```
Met Leu Gly Leu Val Leu Ala Leu Leu Ser Ser Ser Ala Glu Glu
1               5                   10                  15

Tyr Val Gly Leu Ser Ala Asn Gln Cys Ala Val Pro Ala Lys Asp Arg
                20                  25                  30

Val Asp Cys Gly Tyr Pro His Val Thr Pro Lys Glu Cys Asn Asn Arg
            35                  40                  45

Gly Cys Cys Phe Asp Ser Arg Ile Pro Gly Val Pro Trp Cys Phe Lys
        50                  55                  60

Pro Leu Gln Glu Ala Glu Cys Thr Phe
65                  70
```

<210> SEQ ID NO 26
<211> LENGTH: 222
<212> TYPE: DNA
<213> ORGANISM: Homo sapiens

<400> SEQUENCE: 26

```
atgctggggc tggtcctggc cttgctgtcc tccagctctg ctgaggagta cgtgggcctg    60
tctgcaaaacc agtgtgccgt gccagccaag acagggtgg actgcggcta ccccatgtc   120
accccaagg agtgcaacaa ccggggctgc tgctttgact ccaggatccc tggagtgcct   180
tggtgtttca gcccctgca ggaagcagaa tgcaccttct ga                       222
```

<210> SEQ ID NO 27
<211> LENGTH: 181
<212> TYPE: PRT
<213> ORGANISM: Homo sapiens

<400> SEQUENCE: 27

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80
```

```
Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
            165                 170                 175

Pro Ser Tyr Ala Ser
            180
```